(12) United States Patent
Gill et al.

(10) Patent No.: US 11,484,189 B2
(45) Date of Patent: Nov. 1, 2022

(54) PORTABLE IMAGING SYSTEM EMPLOYING A MINIATURE ENDOSCOPE

(75) Inventors: Thomas J. Gill, Weston, MA (US); James E. McDonald, Monson, MA (US)

(73) Assignee: VisionScope Technologies LLC, Littleton, MA (US)

( * ) Notice: Subject to any disclaimer, the term of this patent is extended or adjusted under 35 U.S.C. 154(b) by 0 days.

(21) Appl. No.: 12/439,116

(22) PCT Filed: Aug. 30, 2007

(86) PCT No.: PCT/US2007/019032
§ 371 (c)(1),
(2), (4) Date: Feb. 26, 2009

(87) PCT Pub. No.: WO2008/027448
PCT Pub. Date: Mar. 6, 2008

(65) Prior Publication Data
US 2009/0253967 A1  Oct. 8, 2009

Related U.S. Application Data

(63) Continuation-in-part of application No. 11/788,747, filed on Apr. 20, 2007, now Pat. No. 10,595,710, (Continued)

(51) Int. Cl.
*A61B 1/00* (2006.01)
*A61B 1/07* (2006.01)
(Continued)

(52) U.S. Cl.
CPC ...... *A61B 1/00142* (2013.01); *A61B 1/00059* (2013.01); *A61B 1/00135* (2013.01);
(Continued)

(58) Field of Classification Search
CPC ............ A61B 1/00142; A61B 1/00059; A61B 1/00135; A61B 1/00165; A61B 1/0607;
(Continued)

(56) References Cited

U.S. PATENT DOCUMENTS 3,261,349 A   7/1966   Wallace
3,902,880 A   9/1975   Strack
(Continued)

FOREIGN PATENT DOCUMENTS

DE   88 14 573.5   1/1990
DE   93 18 620.7   11/1993
(Continued)

OTHER PUBLICATIONS

Rol, P. et al., "Optical Properties of miniaturized Endoscopes for Ophthalmic Use," Optical Engineering, Jul. 1995/vol. 34 No. 7.
(Continued)

*Primary Examiner* — Ralph A Lewis
*Assistant Examiner* — Mirayda A Aponte
(74) *Attorney, Agent, or Firm* — McCarter & English, LLP

(57) ABSTRACT

A cart or man-portable system and method for performing endoscopic procedures is provided. A portable display device, such as a laptop computer, is coupled to a handle comprising a miniature camera and fiber optic illumination subsystem. A sterile disposable portion is fitted over the illumination subsystem and inserted into a target area on a patient. Images of the target area are conveyed from the camera to the display device while an endoscopic procedure is performed, thus facilitating real-time diagnosis during the procedure.

38 Claims, 37 Drawing Sheets

Related U.S. Application Data which is a continuation-in-part of application No. 11/512,715, filed on Aug. 30, 2006, now abandoned.

(51) Int. Cl.
  *A61B 1/06* (2006.01)
  *G02B 3/00* (2006.01)
  *A61B 1/04* (2006.01)

(52) U.S. Cl.
  CPC ........ *A61B 1/00165* (2013.01); *A61B 1/0607* (2013.01); *A61B 1/07* (2013.01); *A61B 1/00016* (2013.01); *A61B 1/043* (2013.01); *G02B 3/0087* (2013.01)

(58) Field of Classification Search
  CPC . A61B 1/00016; A61B 1/043; A61B 1/00125; A61B 1/07; A61B 1/00002; A61B 1/00131; A61B 1/00163; A61B 1/06; A61B 1/00011; A61B 1/04; A61C 1/07; A61C 1/00016; G02B 3/0087
  USPC ............... 600/112, 114, 121–125, 182, 249; 385/115–119; 362/572–575; 606/15, 16
  See application file for complete search history.

(56) References Cited

U.S. PATENT DOCUMENTS

| | | | |
|---|---|---|---|
| 3,941,121 | A | 3/1976 | Olinger et al. |
| 4,164,364 | A * | 8/1979 | Witte ............................. 385/31 |
| 4,254,762 | A | 3/1981 | Yoon |
| 4,493,537 | A | 1/1985 | Nakahashi |
| 4,535,773 | A | 8/1985 | Yoon |
| 4,593,937 | A | 6/1986 | Schawann et al. |
| 4,593,973 | A | 6/1986 | Yoshida et al. |
| 4,607,622 | A | 8/1986 | Fritch et al. |
| 4,610,242 | A | 9/1986 | Santangelo |
| D286,566 | S | 11/1986 | Vukovic |
| 4,641,912 | A | 2/1987 | Goldenberg |
| 4,755,029 | A | 7/1988 | Okabe |
| 4,772,093 | A | 9/1988 | Abele et al. |
| 4,784,144 | A * | 11/1988 | Ono .................... A61B 1/00165 385/117 |
| 4,790,295 | A * | 12/1988 | Tashiro .............. A61B 1/00096 600/176 |
| 4,802,461 | A | 2/1989 | Cho |
| 4,854,302 | A | 8/1989 | Allred, III |
| 4,878,485 | A | 11/1989 | Adair |
| 4,904,246 | A | 2/1990 | Atkinson |
| 4,921,326 | A | 5/1990 | Wild et al. |
| 4,947,245 | A | 8/1990 | Ogawa et al. |
| 4,979,498 | A | 12/1990 | Oneda et al. |
| 5,074,642 | A | 12/1991 | Hicks |
| 5,116,353 | A | 5/1992 | Green |
| 5,121,740 | A | 6/1992 | Uram |
| 5,156,142 | A | 10/1992 | Anapliotis et al. |
| 5,159,919 | A | 11/1992 | Chikama |
| 5,168,863 | A | 12/1992 | Kurtzer |
| 5,172,685 | A | 12/1992 | Nudelman |
| 5,184,602 | A | 2/1993 | Anapliotis et al. |
| 5,207,213 | A | 5/1993 | Auhll et al. |
| 5,237,984 | A | 8/1993 | Williams, III et al. |
| 5,269,772 | A | 12/1993 | Wilk |
| 5,274,500 | A | 12/1993 | Dunn |
| 5,290,279 | A | 3/1994 | Bonati et al. |
| 5,311,858 | A * | 5/1994 | Adair .................... A61B 17/221 600/106 |
| 5,311,859 | A | 5/1994 | Monroe et al. |
| 5,323,766 | A | 6/1994 | Uram |
| 5,323,767 | A | 6/1994 | Lafferty et al. |
| 5,329,936 | A | 7/1994 | Lafferty et al. |
| 5,337,734 | A | 8/1994 | Saab |
| 5,341,240 | A | 8/1994 | Broome |
| 5,347,990 | A | 9/1994 | Ebling et al. |
| 5,369,525 | A | 11/1994 | Bala et al. |
| 5,377,668 | A | 1/1995 | Ehmsen et al. |
| 5,402,768 | A | 4/1995 | Adair |
| 5,406,938 | A | 4/1995 | Mersch et al. |
| 5,408,992 | A | 4/1995 | Hamlin et al. |
| 5,413,092 | A | 5/1995 | Williams, III et al. |
| 5,458,132 | A | 10/1995 | Yabe et al. |
| 5,476,090 | A | 12/1995 | Kishi |
| 5,483,951 | A | 1/1996 | Frassica et al. |
| 5,489,256 | A | 2/1996 | Adair |
| 5,496,259 | A | 3/1996 | Perkins |
| 5,518,502 | A | 5/1996 | Kaplan et al. |
| 5,538,497 | A | 7/1996 | Hori |
| 5,569,161 | A | 10/1996 | Ebling et al. |
| 5,573,493 | A | 11/1996 | Sauer et al. |
| 5,573,496 | A | 11/1996 | Sauer et al. |
| 5,575,757 | A | 11/1996 | Kenedy |
| 5,582,190 | A | 12/1996 | Slavin et al. |
| 5,587,839 | A | 12/1996 | Miyano et al. |
| 5,591,160 | A | 1/1997 | Reynard |
| 5,591,192 | A | 1/1997 | Privitera et al. |
| 5,599,278 | A | 2/1997 | Hibbard |
| 5,617,498 | A | 4/1997 | Cawood |
| 5,630,784 | A | 5/1997 | Siegmund et al. |
| 5,630,788 | A | 5/1997 | Forkner et al. |
| 5,685,822 | A | 11/1997 | Harhen |
| 5,690,605 | A | 11/1997 | Hamlin et al. |
| 5,700,236 | A * | 12/1997 | Sauer .................. A61B 1/00101 600/121 |
| 5,702,348 | A | 12/1997 | Harhen |
| 5,704,892 | A | 1/1998 | Adair |
| 5,735,792 | A | 4/1998 | Vanden Hoek et al. |
| 5,751,341 | A | 5/1998 | Chaleki et al. |
| 5,776,049 | A | 7/1998 | Takahashi |
| 5,788,628 | A | 8/1998 | Matsuno et al. |
| 5,817,015 | A | 10/1998 | Adair |
| 5,827,177 | A | 10/1998 | Oneda et al. |
| 5,873,814 | A | 2/1999 | Adair |
| 5,876,329 | A | 3/1999 | Harhen |
| 5,879,287 | A | 3/1999 | Yoshihashi |
| 5,879,289 | A | 3/1999 | Yarush et al. |
| 5,882,295 | A | 3/1999 | Kope |
| 5,892,630 | A | 4/1999 | Broome |
| 5,919,130 | A | 7/1999 | Monroe et al. |
| 5,921,917 | A | 7/1999 | Barthel et al. |
| 5,928,137 | A | 7/1999 | Green |
| 5,941,817 | A | 8/1999 | Crawford |
| 5,947,958 | A | 9/1999 | Woodward et al. |
| 5,947,985 | A | 9/1999 | Imran |
| 5,960,145 | A * | 9/1999 | Sanchez ........................ 385/116 |
| 5,961,445 | A | 10/1999 | Chikama |
| 5,984,861 | A * | 11/1999 | Crowley ............. A61B 5/0071 600/175 |
| 6,001,084 | A | 12/1999 | Riek et al. |
| 6,013,025 | A | 1/2000 | Bonne et al. |
| 6,059,720 | A | 5/2000 | Furusawa et al. |
| 6,086,542 | A | 7/2000 | Glowa et al. |
| 6,086,554 | A | 7/2000 | Humphreys, Jr. et al. |
| 6,124,883 | A | 9/2000 | Suzuki et al. |
| 6,152,872 | A | 11/2000 | Peck et al. |
| 6,179,776 | B1 | 1/2001 | Adams et al. |
| 6,190,353 | B1 | 2/2001 | Makower et al. |
| 6,201,915 | B1 | 3/2001 | Rizkin et al. |
| 6,226,432 | B1 * | 5/2001 | Gonda ............... G02B 23/2476 385/115 |
| 6,275,255 | B1 | 8/2001 | Adair et al. |
| 6,293,910 | B1 | 9/2001 | Yamakita et al. |
| 6,306,083 | B1 | 10/2001 | Bonne et al. |
| 6,310,642 | B1 | 10/2001 | Adair et al. |
| 6,322,498 | B1 | 11/2001 | Gravenstein et al. |
| 6,350,231 | B1 | 2/2002 | Ailinger et al. |
| 6,387,044 | B1 | 5/2002 | Tachibana et al. |
| 6,393,431 | B1 | 5/2002 | Salvati et al. |
| 6,398,776 | B1 | 6/2002 | Sekino et al. |
| 6,411,835 | B1 | 6/2002 | Modell et al. |
| 6,419,654 | B1 | 7/2002 | Kadan |
| 6,432,047 | B1 | 8/2002 | Gust et al. |
| 6,478,730 | B1 | 11/2002 | Bala et al. |
| 6,487,440 | B2 | 11/2002 | Deckert et al. |

(56) References Cited

U.S. PATENT DOCUMENTS

| | | |
|---|---|---|
| 6,503,196 B1 | 1/2003 | Kehr et al. |
| 6,527,704 B1 | 3/2003 | Chang et al. |
| 6,530,881 B1 | 3/2003 | Ailinger et al. |
| 6,549,794 B1 | 4/2003 | Nadeau, Jr. et al. |
| 6,554,765 B1 | 4/2003 | Yarush et al. |
| 6,561,973 B1 | 5/2003 | Bala |
| 6,589,162 B2 | 7/2003 | Nakashima et al. |
| 6,599,238 B2 | 7/2003 | Ooshima et al. |
| 6,612,981 B2 | 9/2003 | Onishi et al. |
| 6,659,940 B2 | 12/2003 | Adler |
| 6,695,772 B1 | 2/2004 | Bon et al. |
| 6,712,757 B2 | 3/2004 | Becker et al. |
| 6,730,019 B2 | 5/2004 | Irion |
| 6,733,187 B2 | 5/2004 | Page et al. |
| 6,740,030 B2 | 5/2004 | Martone et al. |
| 6,748,730 B2 | 6/2004 | Breneur et al. |
| 6,761,684 B1 | 7/2004 | Speier |
| 6,761,685 B2 | 7/2004 | Adams et al. |
| 6,790,176 B2* | 9/2004 | Ouchi .................. A61B 1/042 385/117 |
| 6,808,505 B2 | 10/2004 | Kadan |
| 6,826,422 B1 | 11/2004 | Modell et al. |
| 6,863,651 B2 | 3/2005 | Remijian et al. |
| 6,936,004 B2 | 8/2005 | Utsui |
| 6,955,644 B2 | 10/2005 | Forkey et al. |
| 7,219,222 B1* | 5/2007 | Durbin .................. G06F 21/305 705/51 |
| 7,242,301 B2* | 7/2007 | August ............. G06K 7/10178 340/539.1 |
| 7,510,524 B2 | 3/2009 | Vayser et al. |
| 7,517,321 B2* | 4/2009 | McCullough et al. ...... 600/566 |
| 7,708,689 B2 | 5/2010 | Deppmeier et al. |
| 7,811,228 B2 | 10/2010 | Adams |
| 7,860,555 B2 | 12/2010 | Saadat |
| 7,901,351 B2 | 3/2011 | Prescott |
| 7,901,353 B2 | 3/2011 | Vayser et al. |
| 7,942,814 B2 | 5/2011 | Remijian et al. |
| 8,038,602 B2 | 10/2011 | Gill et al. |
| 8,317,689 B1 | 11/2012 | Remijian et al. |
| 8,659,646 B2 | 2/2014 | Adler et al. |
| 8,858,425 B2 | 10/2014 | Farr et al. |
| 8,870,749 B2 | 10/2014 | Fouts et al. |
| 9,131,832 B2 | 9/2015 | Fouts et al. |
| 9,462,234 B2 | 10/2016 | Blanquart et al. |
| 9,757,507 B2 | 9/2017 | Holoien et al. |
| 9,913,570 B2 | 3/2018 | Kucharski et al. |
| 10,143,358 B2 | 12/2018 | Alexander et al. |
| 10,405,886 B2 | 9/2019 | Washburn, II et al. |
| 10,582,837 B2 | 3/2020 | Hebert |
| 10,945,589 B2 | 3/2021 | Alexander et al. |
| 2001/0000040 A1 | 3/2001 | Adams et al. |
| 2002/0013513 A1 | 1/2002 | Bala |
| 2002/0022763 A1 | 2/2002 | Sano et al. |
| 2002/0022764 A1* | 2/2002 | Smith ................ A61B 17/3417 600/114 |
| 2002/0045811 A1 | 4/2002 | Kittrell et al. |
| 2002/0087047 A1 | 7/2002 | Remijian et al. |
| 2003/0028078 A1 | 2/2003 | Glukhovsky |
| 2003/0083552 A1* | 5/2003 | Remijian ............ A61B 1/00135 600/182 |
| 2003/0088798 A1* | 5/2003 | Ono ................... G06F 1/266 713/310 |
| 2003/0138753 A1* | 7/2003 | Galarza ............... A61C 19/004 433/29 |
| 2003/0163030 A1 | 8/2003 | Arriaga |
| 2003/0167000 A1 | 9/2003 | Mullick et al. |
| 2004/0085441 A1 | 5/2004 | Onishi et al. |
| 2004/0186346 A1 | 9/2004 | Smith et al. |
| 2004/0210107 A1 | 10/2004 | Tani et al. |
| 2004/0246744 A1 | 12/2004 | Krupa et al. |
| 2005/0043690 A1 | 2/2005 | Todd |
| 2005/0099824 A1 | 5/2005 | Dowling et al. |
| 2005/0215859 A1 | 9/2005 | Chin et al. |
| 2005/0234298 A1 | 10/2005 | Kucklick et al. |
| 2005/0267330 A1 | 12/2005 | Deppmeier et al. |
| 2005/0272975 A1 | 12/2005 | McWeeney et al. |
| 2005/0283048 A1 | 12/2005 | Gill et al. |
| 2006/0069314 A1 | 3/2006 | Farr |
| 2006/0088798 A1* | 4/2006 | Feinbloom ............ A61C 19/003 433/29 |
| 2006/0173242 A1 | 8/2006 | Navok et al. |
| 2006/0206007 A1 | 9/2006 | Bala |
| 2006/0206178 A1 | 9/2006 | Kim |
| 2007/0021713 A1 | 1/2007 | Kumar et al. |
| 2007/0167681 A1 | 7/2007 | Gill et al. |
| 2007/0182812 A1 | 8/2007 | Ritchey |
| 2007/0198357 A1* | 8/2007 | Ravazzolo .......... G06F 19/3437 705/23 |
| 2007/0249904 A1 | 10/2007 | Amano et al. |
| 2008/0045800 A2 | 2/2008 | Farr |
| 2008/0058842 A1 | 3/2008 | Emanuel |
| 2008/0064925 A1 | 3/2008 | Gill et al. |
| 2008/0183028 A1 | 7/2008 | Guillen Garcia et al. |
| 2008/0255519 A1 | 10/2008 | Piskun et al. |
| 2009/0082630 A1 | 3/2009 | Tulley |
| 2010/0022824 A1 | 1/2010 | Cybulski et al. |
| 2010/0121139 A1 | 5/2010 | OuYang et al. |
| 2010/0121142 A1 | 5/2010 | OuYang et al. |
| 2010/0121155 A1 | 5/2010 | OuYang et al. |
| 2010/0217080 A1 | 8/2010 | Cheung et al. |
| 2010/0284580 A1 | 11/2010 | OuYang et al. |
| 2010/0286477 A1 | 11/2010 | OuYang et al. |
| 2010/0292684 A1 | 11/2010 | Cybulski et al. |
| 2011/0060183 A1 | 3/2011 | Castro et al. |
| 2011/0230723 A1 | 9/2011 | Castro et al. |
| 2011/0301578 A1 | 12/2011 | Muniz-Medina et al. |
| 2012/0071721 A1 | 3/2012 | Remijian et al. |
| 2012/0095458 A1 | 4/2012 | Cybulski et al. |
| 2012/0116362 A1 | 5/2012 | Kieturakis |
| 2012/0184814 A1 | 7/2012 | Ebata et al. |
| 2012/0209074 A1 | 8/2012 | Titus |
| 2013/0046142 A1 | 2/2013 | Remijian et al. |
| 2013/0197545 A1 | 8/2013 | Garcia et al. |
| 2013/0201356 A1 | 8/2013 | Kennedy et al. |
| 2013/0204085 A1 | 8/2013 | Alexander et al. |
| 2013/0296648 A1 | 11/2013 | OuYang et al. |
| 2013/0303846 A1 | 11/2013 | Cybulski et al. |
| 2014/0249405 A1 | 9/2014 | Wimer |
| 2015/0196193 A1 | 7/2015 | Kienzle et al. |
| 2016/0066770 A1 | 3/2016 | Barbato et al. |
| 2017/0280988 A1 | 10/2017 | Barbato et al. |
| 2018/0220878 A1 | 8/2018 | Remijian et al. |
| 2019/0038232 A1 | 2/2019 | Mirza et al. |
| 2019/0261836 A1 | 8/2019 | Ouyang et al. |
| 2020/0187752 A1 | 6/2020 | Williams |
| 2021/0007585 A1 | 1/2021 | Gill, IV et al. |

FOREIGN PATENT DOCUMENTS

| | | |
|---|---|---|
| DE | 102015000251 A1 | 7/2016 |
| EP | 0 072 205 | 2/1983 |
| EP | 0 316 244 | 8/1988 |
| EP | 0280397 A2 | 8/1988 |
| EP | 0 461 669 | 12/1991 |
| EP | 0549097 | 6/1993 |
| EP | 0 586 162 | 3/1994 |
| EP | 0 647 425 | 4/1995 |
| EP | 0672379 A1 | 9/1995 |
| GB | 1078036 A | 8/1967 |
| GB | 2 339 922 | 2/2000 |
| JP | 59-002005 | 1/1984 |
| JP | 01-204642 | 8/1989 |
| JP | H04-037812 A | 2/1992 |
| JP | 04-177310 | 6/1992 |
| JP | 05-253167 | 10/1993 |
| JP | 05-317241 | 12/1993 |
| JP | 06-202007 | 7/1994 |
| JP | 06-209904 | 8/1994 |
| JP | 06-250104 | 9/1994 |
| JP | 07-013087 | 1/1995 |
| JP | H08-502197 A | 3/1996 |
| JP | 08-110486 | 4/1996 |
| JP | 09-178446 | 7/1997 |

(56) References Cited

FOREIGN PATENT DOCUMENTS

| | | |
|---|---|---|
| JP | 11-56774 A | 3/1999 |
| JP | 2000-000203 | 1/2000 |
| JP | 00-097846 | 4/2000 |
| JP | 01/264644 | 9/2001 |
| JP | 2001-251612 A | 9/2001 |
| JP | 2001-257913 A | 9/2001 |
| JP | 2002-102142 A | 4/2002 |
| JP | 2002-355262 A | 12/2002 |
| JP | 2003-088499 A | 3/2003 |
| JP | 2003-116783 A | 4/2003 |
| JP | 2004-305429 A | 11/2004 |
| JP | 2004-358107 A | 12/2004 |
| JP | 2008-514304 A | 5/2008 |
| WO | WO 92/22238 | 12/1992 |
| WO | WO 94/08505 | 4/1994 |
| WO | WO 94/14367 | 7/1994 |
| WO | WO 96/39916 | 12/1996 |
| WO | WO 97/05473 | 2/1997 |
| WO | WO 97/09937 | 3/1997 |
| WO | WO 98/20787 | 5/1998 |
| WO | WO 98/35607 | 8/1998 |
| WO | WO 99/35960 | 7/1999 |
| WO | WO 00/03272 | 1/2000 |
| WO | WO 00/13568 | 3/2000 |
| WO | WO 01/19235 | 3/2001 |
| WO | WO 01/22866 | 4/2001 |
| WO | 2001/091653 A2 | 12/2001 |
| WO | 2002/76290 A1 | 10/2002 |
| WO | 2003/34905 A2 | 5/2003 |
| WO | WO 03/034905 | 5/2003 |
| WO | WO 2005/112736 | 12/2005 |
| WO | 2006/037034 A2 | 4/2006 |
| WO | 2006/96797 A2 | 9/2006 |
| WO | 2006/108143 A2 | 10/2006 |
| WO | 2008/27448 A2 | 3/2008 |
| WO | 2008/087243 A1 | 7/2008 |
| WO | 2010/098807 A1 | 9/2010 |
| WO | 2014/073950 A1 | 5/2014 |
| WO | 2015/112824 A1 | 7/2015 |
| WO | 2016/005718 A1 | 1/2016 |

OTHER PUBLICATIONS

InnerVue Diagnostic Scope System—www.innervuescope.com.
International Search Report for Application No. PCT/US2009/069936, dated Apr. 6, 2010. 4 pages.
Japanese Office Action for Application No. 2011-551053, dated Feb. 19, 2014. 4 pages.
Japanese Office Action for Application No. 2011-551053, dated Jan. 15, 2013. 8 pages.
Poehling, Instrumentation for small joints: the arthroscope. Arthroscopy. 1988;4(1):45-6.
Vangsness et al., A disposable fiberoptic arthroscope: a cadaver study. Foot Ankle Int. Sep. 1994;15(9):502-4.
U.S. Appl. No. 11/788,747, filed Apr. 20, 2007, U.S. Pat. No. 10,595,710, Issued.

* cited by examiner

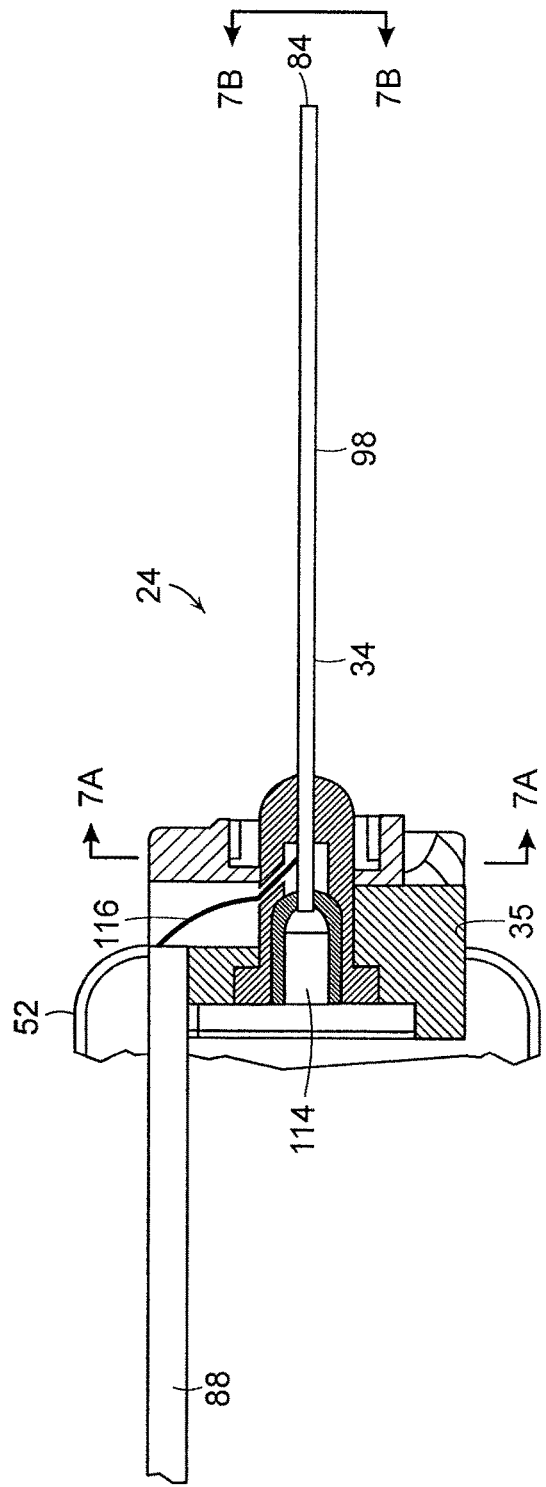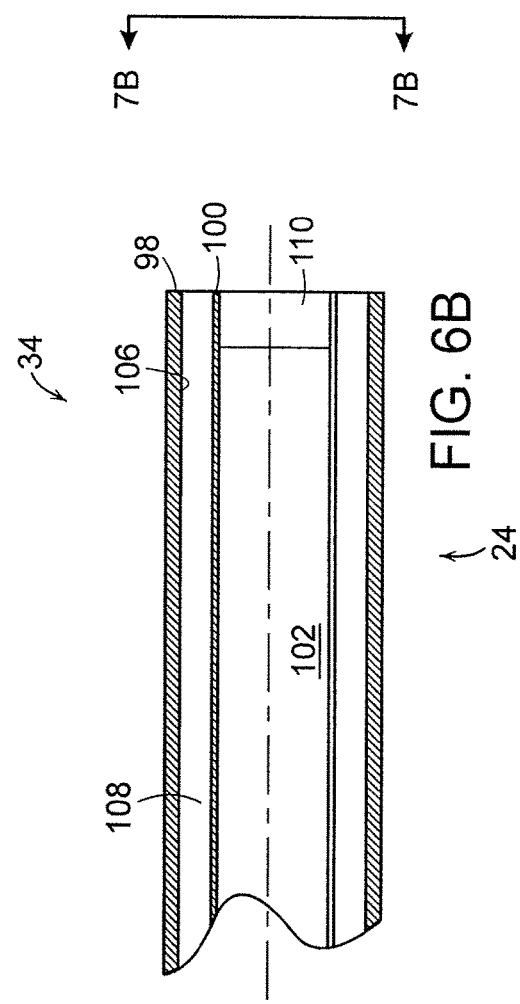

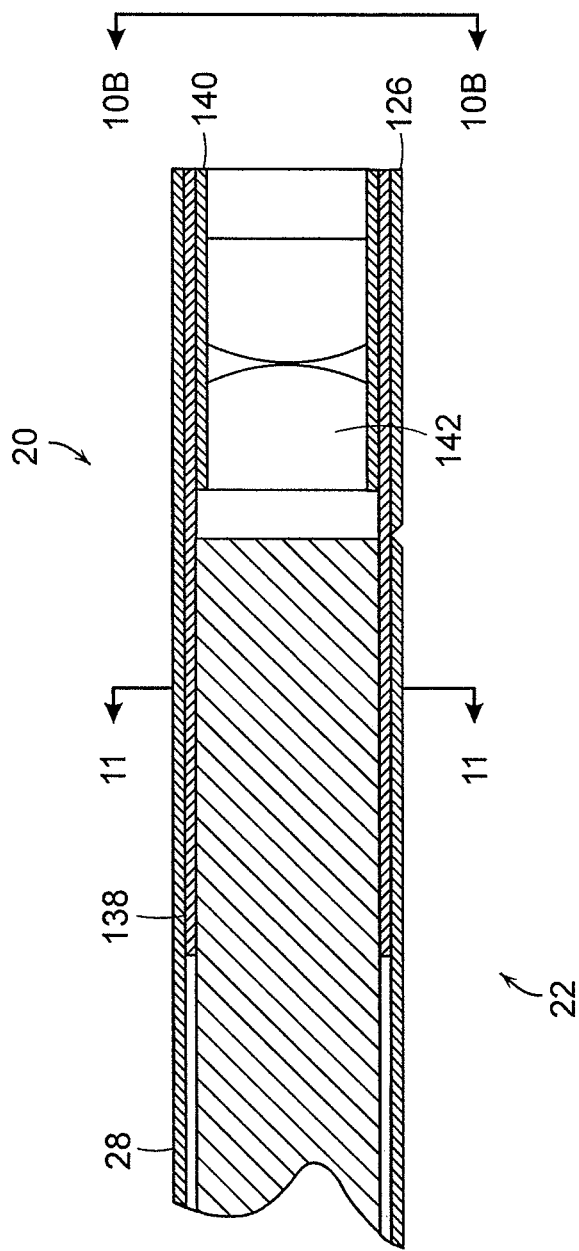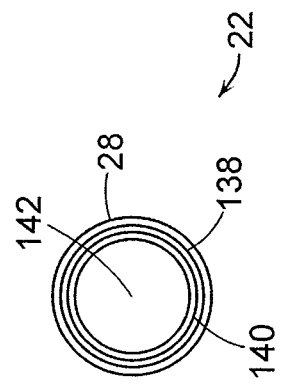
FIG. 10A
FIG. 10B

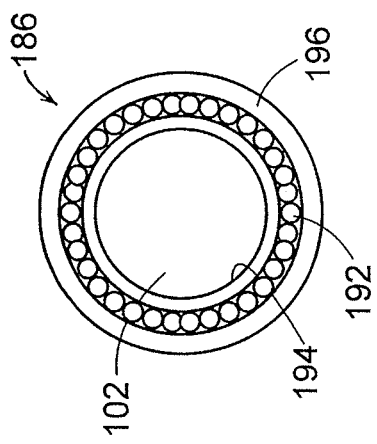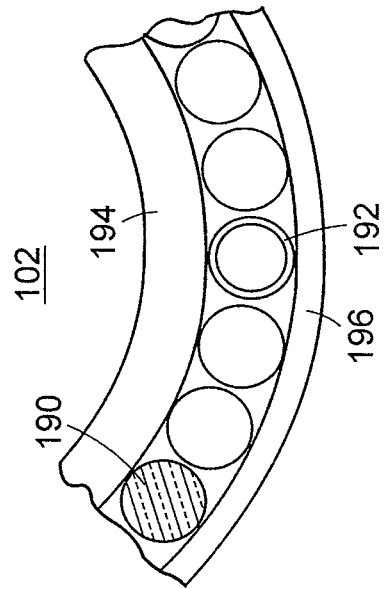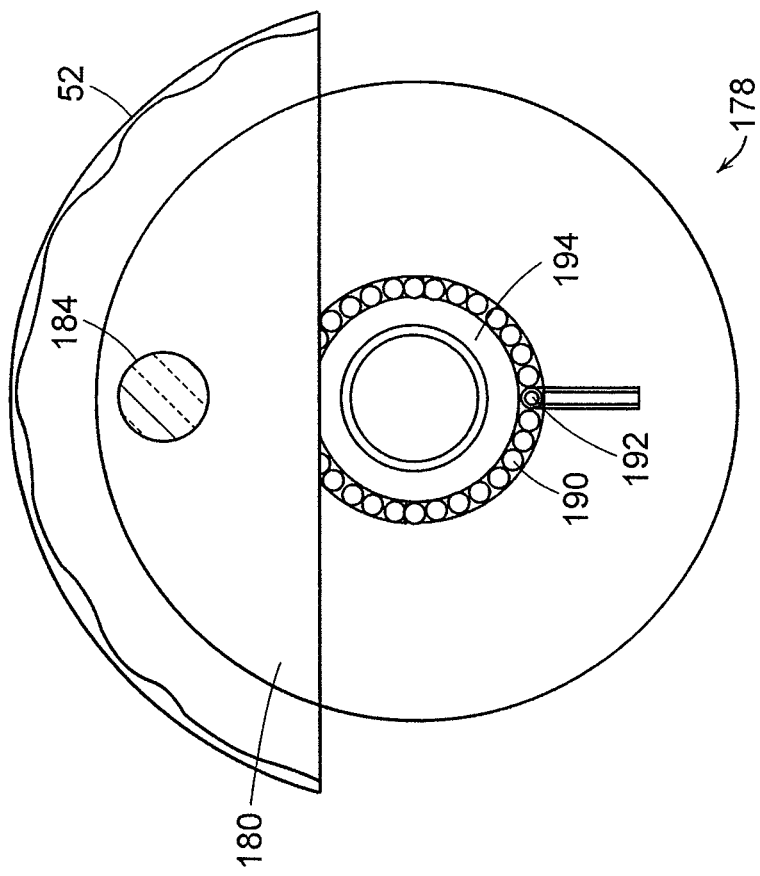

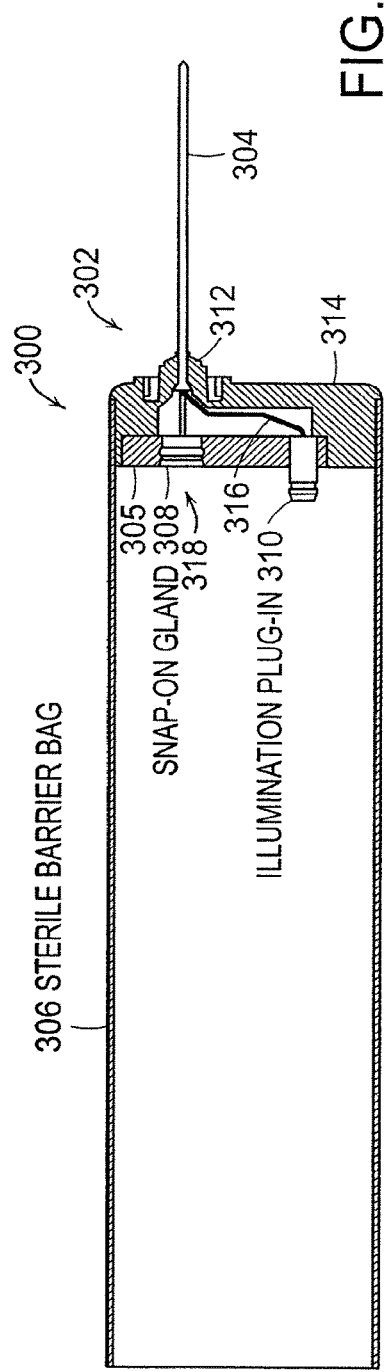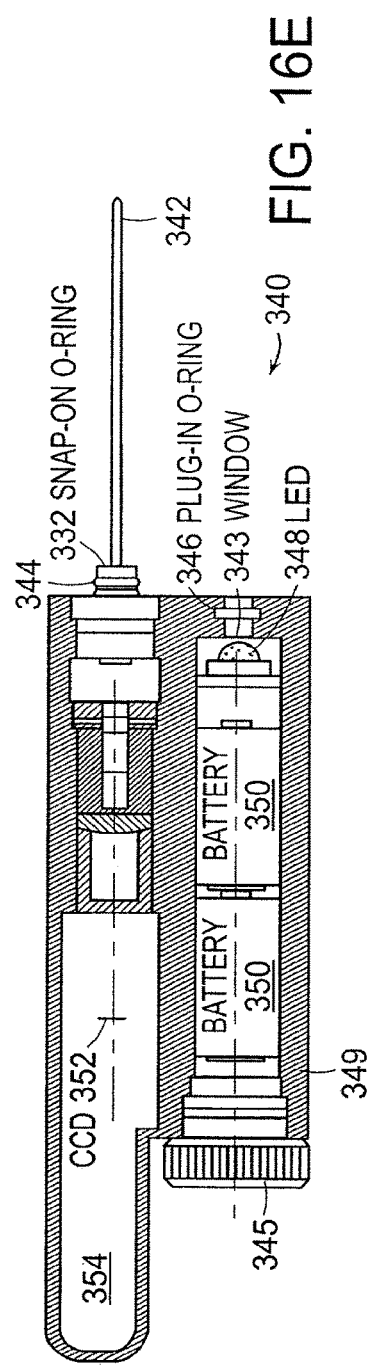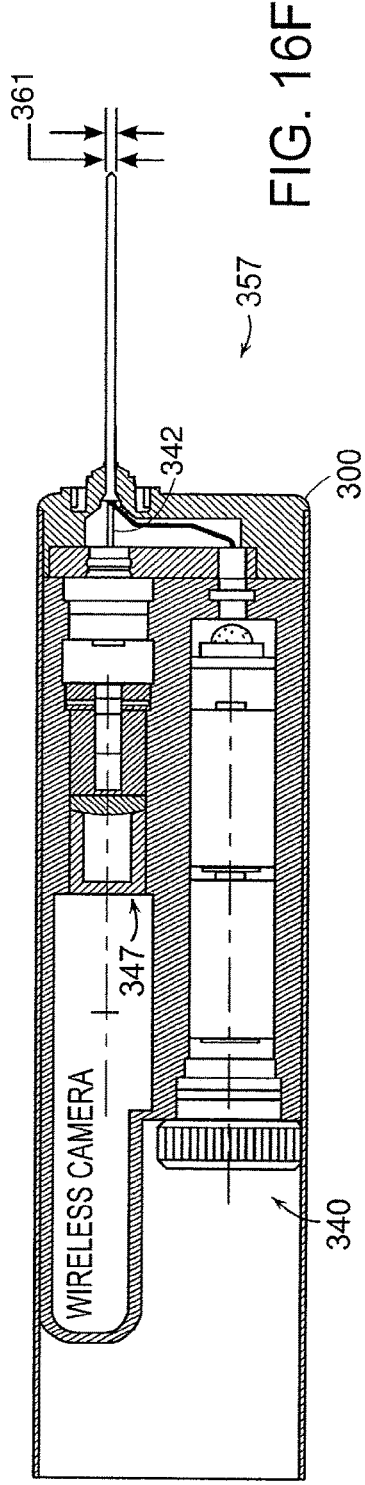

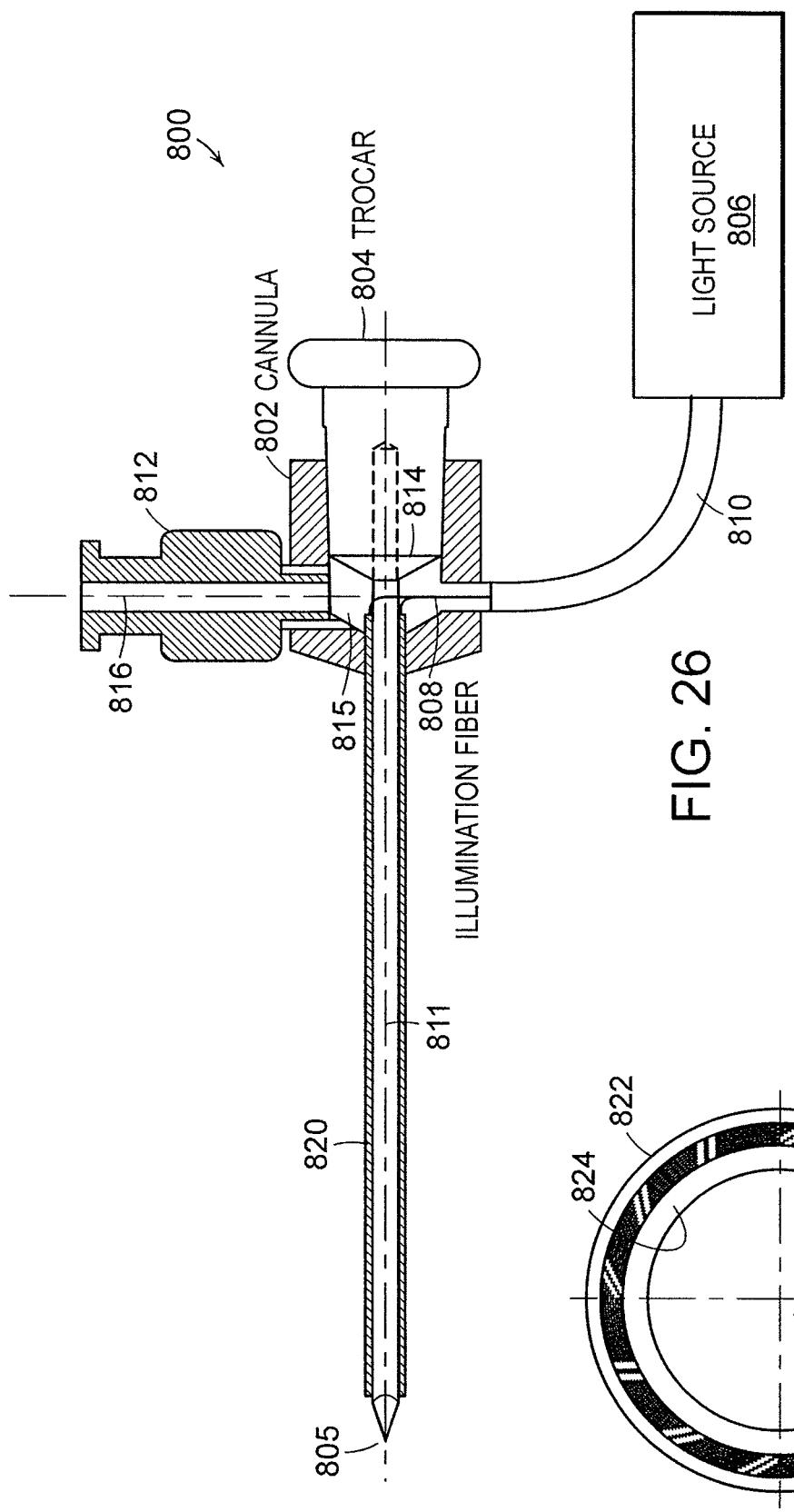

480 ↘

```
┌─────────────────────────────────────────────┐
│ Providing a packaged disposable kit having an│
│ identification element such as a machine readable code│
│                     482                      │
└─────────────────────────────────────────────┘
                       ↓
┌─────────────────────────────────────────────┐
│ Recording use of the disposable kit with the │
│ identification element and the system computer│
│                     484                      │
└─────────────────────────────────────────────┘
                       ↓
┌─────────────────────────────────────────────┐
│    Enabling use of the endoscope system with the│
│           recorded disposable kit            │
│                     486                      │
└─────────────────────────────────────────────┘
                       ↓
┌─────────────────────────────────────────────┐
│   Removing disposable components from the    │
│ package and using these with the imaging system│
│         to obtain images of a patient        │
│                     488                      │
└─────────────────────────────────────────────┘
                       ↓
┌─────────────────────────────────────────────┐
│ Removing the disposable components from the imaging│
│ system, disabling further use of the disposable with the│
│ computer system and disposing of the used components│
│                     490                      │
└─────────────────────────────────────────────┘
```

FIG. 28

PORTABLE IMAGING SYSTEM EMPLOYING A MINIATURE ENDOSCOPE

CROSS REFERENCE TO RELATED APPLICATIONS

The present application is a 35 U.S.C. § 371 national stage filing of International Application No. PCT/US2007/019032, filed on Aug. 30, 2007, which is a continuation-in-part of U.S. patent application Ser. No. 11/788,747 filed on Apr. 20, 2007, which is a continuation-in-part of co-pending U.S. patent application Ser. No. 11/512,715 filed on Aug. 30, 2006. The entire contents of the above applications are incorporated herein by reference.

BACKGROUND OF THE INVENTION

Endoscopes enable visual examination of structure inside cavities. In the field of medicine, the use of endoscopes permits inspection of organs for the purposes of diagnosis, viewing of a surgical site, sampling tissue, or facilitating the safe manipulation of other surgical instruments.

Laparoscopes, for example, are used particularly for examining organs in the abdominal area. Laparoscopes typically include a light pipe for illuminating the region to be viewed, at least one lens assembly for focusing and relaying the image of the illuminated object, and a housing for the entire assembly which is structured to minimize tissue damage during the surgical procedure. The light pipe can include a fiber optic element for illuminating the site. The laparoscope housing includes a distal section that can be inserted within a body cavity and a proximal section which can include a handle that a user grips to position the distal end near the surgical site.

Existing endoscopes can include an imaging device such as a charged coupled device (CCD). This device can capture an image of an object being viewed and convey it to a display device, such as a monitor. There is a continuing need to improve on the operational features and manufacturability of endoscope systems that improve imaging capability and reduce the risk to the patient.

SUMMARY OF THE INVENTION

The present invention relates to a small diameter imaging probe or endoscope having improved durability, resolution, and field of view. In a preferred embodiment of the invention, the distal end of the probe including a disposable sheath, can be inserted into the tissue under examination. The probe is less than 3 millimeters in diameter, and preferably less than 2 millimeters in diameter, to reduce trauma at the point of insertion and thereby provide access to sites that are otherwise unavailable for endoscopic procedures.

In a preferred embodiment, the endoscope has a fiber optic waveguide that transmits an image from a distal end to a proximal end. A lens system is positioned at the distal end of the fiber optic waveguide. An imaging device is optically coupled to the proximal end of fiber optic waveguide. A sheath extends about the fiber optic waveguide, the sheath including illumination fibers. Although a preferred embodiment utilizes a probe and sheath assembly having an outer diameter of 2 mm or less, certain applications will accommodate a larger diameter instrument having a larger number of imaging fibers to provide a higher resolution image. These applications can utilize outer diameters in a range of 2-4 mm.

In one embodiment, the lens system having a first lens element, a second lens element and an aperture stop. The lens system couples light from any given position on the object to a plurality of optical fibers such that the numerical aperture of light varies as a function of the angle relative to the longitudinal axis of the lens system. This provides more efficient coupling to the fiber apertures. This is accomplished using a non-telecentric lens system.

A preferred embodiment of the lens system includes a pair of lenses and an aperture stop. The lenses are shaped to improve light collection around the periphery of the distal lens. This provides a clearer image across the entire field of view of the device. The aperture stop is positioned to provide efficient coupling to the array of fibers.

The imaging device can be a charged coupled device (CCD), a CMOS imaging device or other solid state imaging sensor having a two dimensional array of pixel elements. The imaging sensor is mounted on a circuit board in a handle assembly. The sensor can capture an image as an object being viewed and an image processing circuit mounted onto the circuit board transfers the image data over a video cable to a computer for storage, processing and/or display.

The miniature endoscope system can be used for orthopedic, rhematologic, general laparoscopic, gynecological or ear, nose and throat procedures small and large joints, cardiac, oncology, lung, breast, brain, GI and veterinary applications for example. Although many applications require a small diameter to reduce trauma, certain applications can accommodate larger diameters. The probe can include an open channel in either the sheath or the imaging probe to provide for the insertion of other operative elements to flush the site with fluid, direct light or other energy source onto a treatment site, or to remove a tissue sample.

The sheath assembly can include a concentric array of illumination fibers extending to a connector on a sheath hub assembly. Alternatively, the illumination fibers can couple to a fiber connector in the probe assembly that is coupled directly via fiber optic cable extending from the handle to a light source housing. The housing can include a video disk recorder that writes the video onto disk. For certain applications, an illumination bundle can be positioned within the probe such that the sheath is thinner or can accommodate a larger working channel.

The present system, has four preferred applications for orthopedic use: in-office diagnostics, operating room surgical resections/procedures, in office post-operative evaluation, and therapeutic usage for the delivery of medications into joints, while confirming their correct location under direct visualization.

In addition to its use in the office, the system can be used in the operating room instead of a standard arthroscope. By eliminating the need to use arthroscopic irrigation fluid for distension of tissue or a large-bore camera, the amount of pain and swelling following an arthroscopic procedure will be substantially reduced if not eliminated. The patient can return to the office or playing field the next day.

The system is used for the postoperative assessment of the healing process for tissue and bond graft procedures, which are not currently possible using conventional MRI techniques. Examples include: assessment of articular cartilage resurfacing procedures, meniscal repairs, labral repairs, rotator cuff repairs, fracture reductions of joint surfaces, ligament integrity, and other usages.

The system includes a computer (or other viewing system), camera, light source and reusable handle that does not require reprocessing between procedures and a sterile barrier and lens components that is single patient use and disposable. The system eliminates the space requirements, cost of reprocessing equipment, manpower and costs associated with the time sensitive endoscope re-sterilization. In a preferred embodiment, the handle, sheath assembly and controls system is portable with a total weight of ten pounds or less.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 6A is a sectional view of the disposable sheath/illuminator unit;

FIG. 6B is an enlarged sectional view of the distal end to the disposable sheath;

FIG. 10A is an enlarged view of the distal end of the imaging unit as indicated by the portion defined 10A in FIG. 9;

FIG. 10B is a front view of the distal end of the imaging unit taken along the line 10B-10B of FIG. 10A;

FIG. 16A is a sectional view of the endoscope taken along line 16A-16A of FIG. 15;

FIG. 16B is a sectional view of the endoscope taken along line 16B-16B of FIG. 15;

FIG. 16C is an enlarged sectional view of the imaging unit as indicated by the portion defined by 10C in FIG. 16B;

FIGS. 16D-L illustrate preferred embodiments of the invention;

FIG. 26 illustrates a cross-sectional view of an illumination cannula in accordance with another preferred embodiment of the invention;

FIG. 27 illustrates a cross-sectional view of the cannula of FIG. 26;

FIG. 28 illustrates a method of using a labeled disposable kit in accordance with a preferred embodiment of the invention.

DETAILED DESCRIPTION OF THE INVENTION

Figure 1:
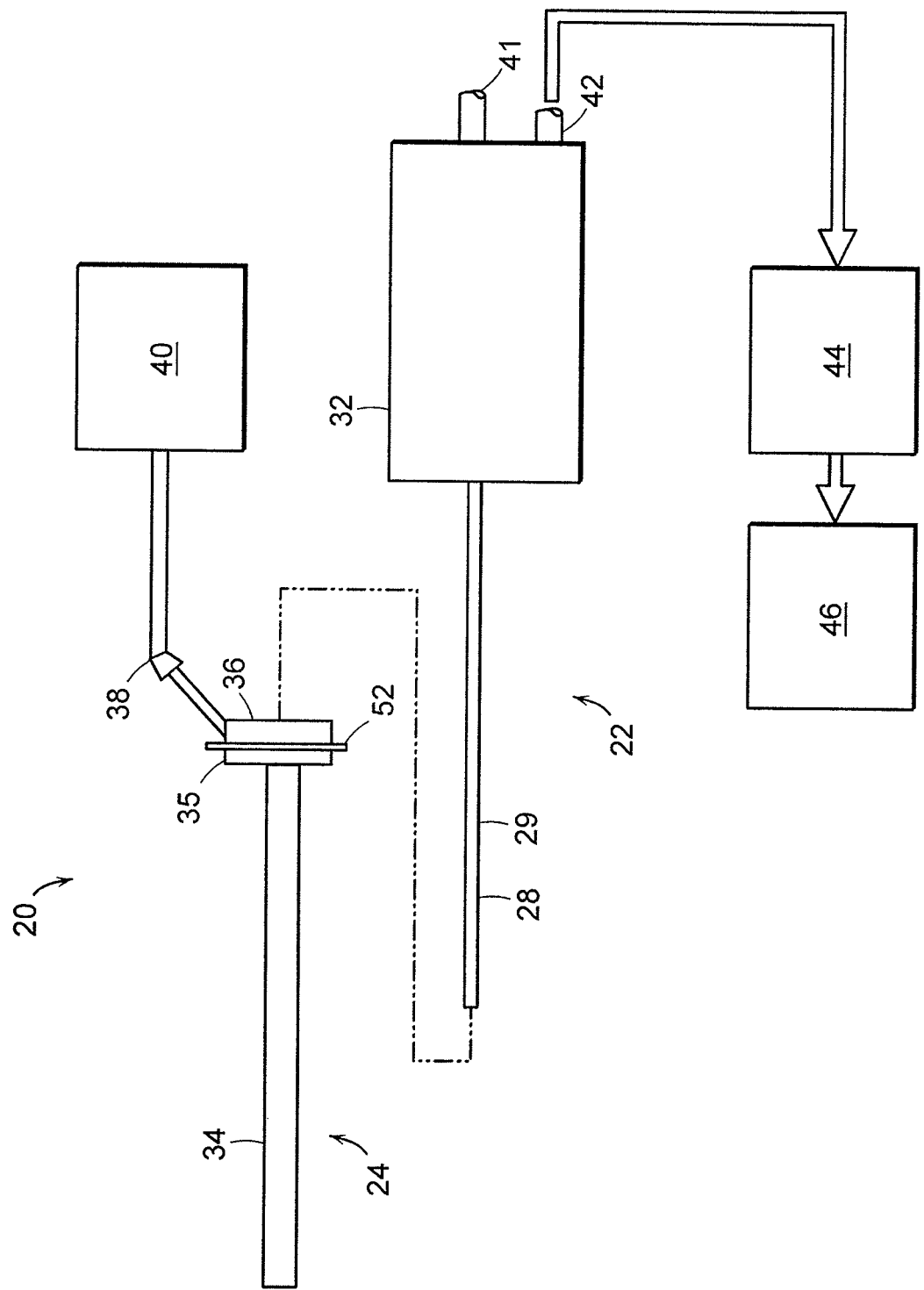
FIG. 1 illustrates a schematic illustration of a miniature endoscope system according to the invention.
Figure 9:
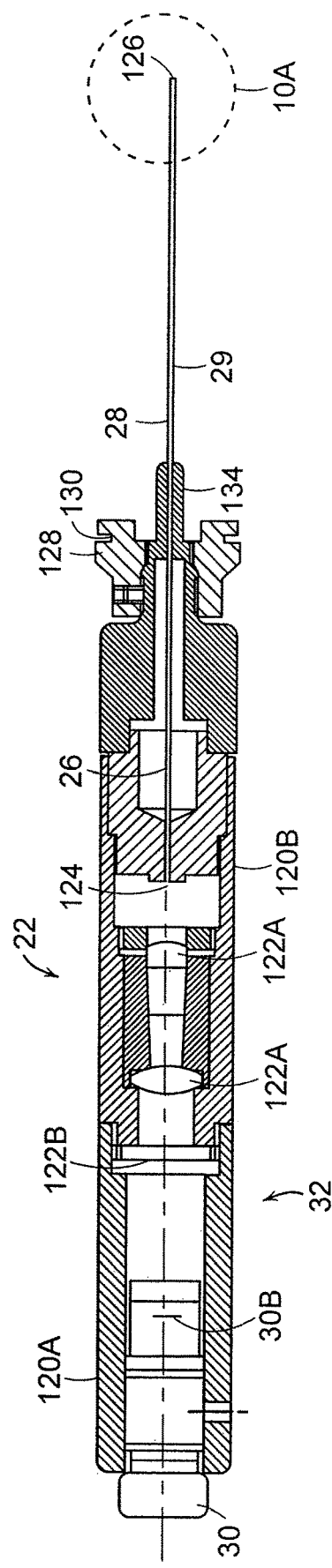
FIG. 9 is a sectional view of an imaging unit of the miniature endoscope.

An embodiment of the invention is illustrated in FIG. 1 that shows a miniature endoscope 20. The endoscope 20 has an imaging unit 22 and a sheath/illuminator unit 24. The endoscope 20 has an image transmission path such as a plurality of optical fibers 26, as best seen at fibers 146 in FIGS. 11 and 12, in an elongated tube 28 of a rod tip 29 used to view objects to be examined. The optical fibers 26 are optically coupled to an imaging device 30, such as a charged coupled device as seen in FIG. 9, or other pixilated flat panel sensor, in a handle 32. A disposable sheath 34 of the sheath/illuminator unit 24 overlies the elongated tube 28 of the rod tip 29, which contains the optical fibers 26. The proximal end of the disposable sheath 34 has a base 35 with a mounting mechanism 36 for securing the sheath to the handle 32. In one embodiment, the disposable sheath 34 of the sheath/illuminator unit 24 has a plurality of optical fibers for transmitting light to the distal end of the disposable sheath 34 and the distal probe 29. The distal end of the disposable sheath/illuminator unit 24 has a connection 38 to connect to a light source 40.

The handle 32 can house a power input 41, used to provide power to the endoscope 20. It is recognized that the light source 40 and/or power source can be mounted within the handle 32.

The handle 32 can also house an image output 42. The image output 42 provides a connection between an imaging device in the imaging unit 22 of the endoscope 20 and an electronic storage and/or display device. In one embodiment, the storage device is a computer 44, which is connected to a monitor 46. A control unit 250 is described in greater detail with respect to FIG. 19.

As explained below in greater detail the imaging unit 22 does not need to be sterilized in that the imaging unit 22 does not contact or is not in direct exposure to the body. The sheath/illuminator unit 24 has the disposable sheath 34 that is a sleeve assembly that is carried by the base 35 secured to the imaging unit 22 that overlies the elongated tube 28 to create a sterilized barrier. In addition, the sheath/illumination unit 24 has a sterilized drape 52 which is mounted to the base 35 of the sheath/illuminator unit 24 and is positioned to overlie the remaining portion of the imaging unit 22 to provide a sterile environment.

Endoscopes and endoscopes with disposable sheaths are described in PCT Application PCT/US00/25107 filed on Sep. 13, 2000 and U.S. patent application Ser. No. 09/518,954 filed on Mar. 6, 2000. The entire contents of the above applications are incorporated herein by reference in their entirety.

Prior to discussing the endoscope 20 in further detail, in order to use the endoscope 20, the endoscope 20 needs to be positioned in the body to view the desired location. One such method is to insert a cannula 60 into the body and thread the endoscope 20 through the cannula 60. One method of inserting the cannula 60 into the body and then inserting the endoscope 20 into a body using the cannula 60 is described below.

Figure 2:
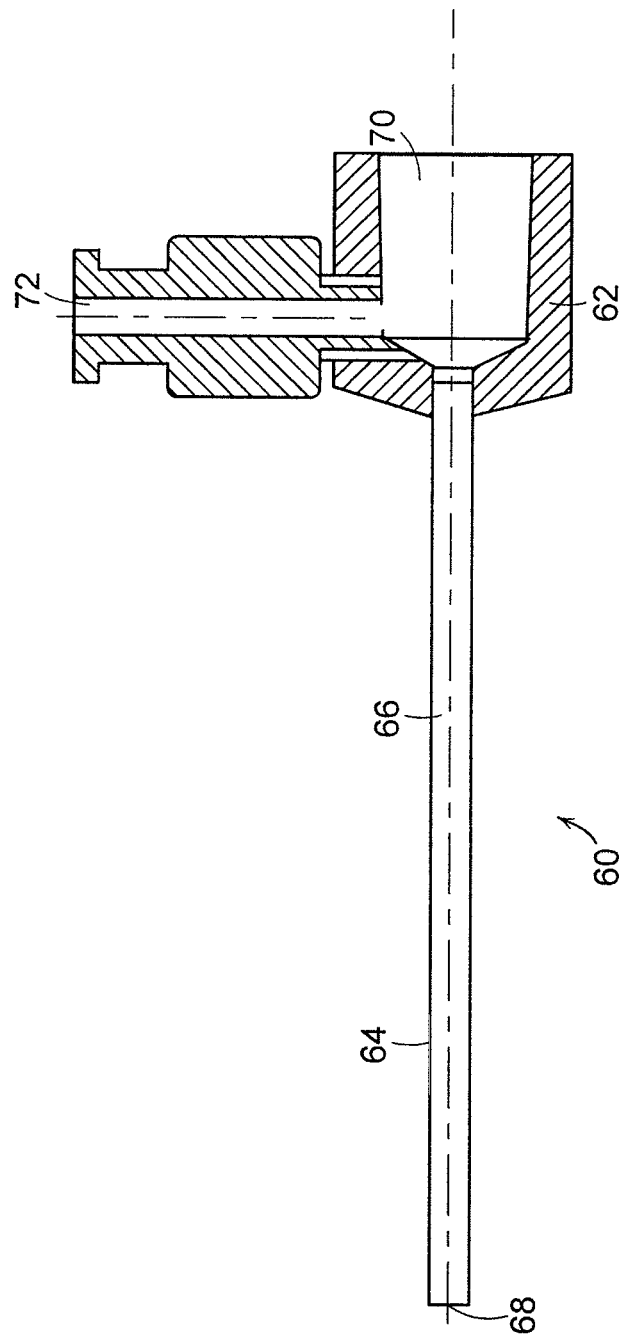
FIG. 2 is a cross-sectional view of cannula.

During an insertion procedure, a cannula 60 such as seen in FIG. 2, is first inserted into a site within a body. The cannula 60 has a base 62 and a tube 64. The tube 64 has a shaft 66 which extends from the distal end 68 to a void 70 in the base 62. In one embodiment, the tube 64 is made of a flexible material such as plastic or thin wall stainless steel. The cannula 60 has a luer 72 for insertion of medications or fluids or for attachment to a suction device.

Figure 3:
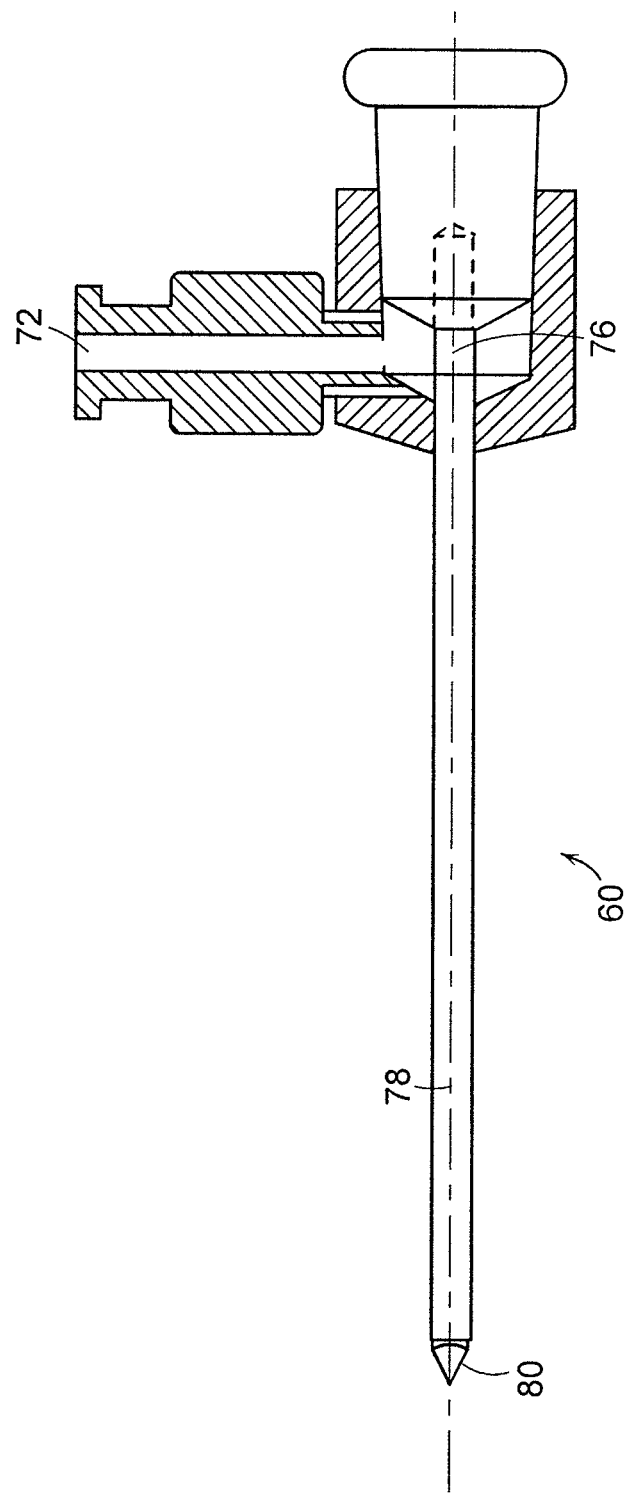
FIG. 3 is a cross-sectional view of a trocar within a cannula.

For insertion of the cannula 60 into the body, a trocar 76, as seen in FIG. 3, is inserted into cannula 60 with a rigid shaft 78 of the trocar 76 received within the shaft 66 of the cannula 60. The rigid shaft 78 of the trocar 76 extends slightly beyond the distal end of the tube 64 of the cannula 60 and has a stylet 80 to cut into the tissue at the surgical site if necessary. Once the cannula 60 is positioned at the surgical site, the trocar 76 is removed from the cannula 60 and the endoscope 20 is installed. The cannula 60 is positioned by the user's hands feeling the location.

While the cannula 60 and trocar 76 are of a relative minimal cost and can be reused after sterilization or disposed of after use, because of several components in the endoscope 20 such as components in the imaging unit 22, it is not desirous to dispose of the entire endoscope 20. The endoscope 20 uses a disposable sleeve or sheath 34 to aid in maintaining a sterile environment and reduce or eliminate the sterilization requirements prior to reuse.

Figure 4:
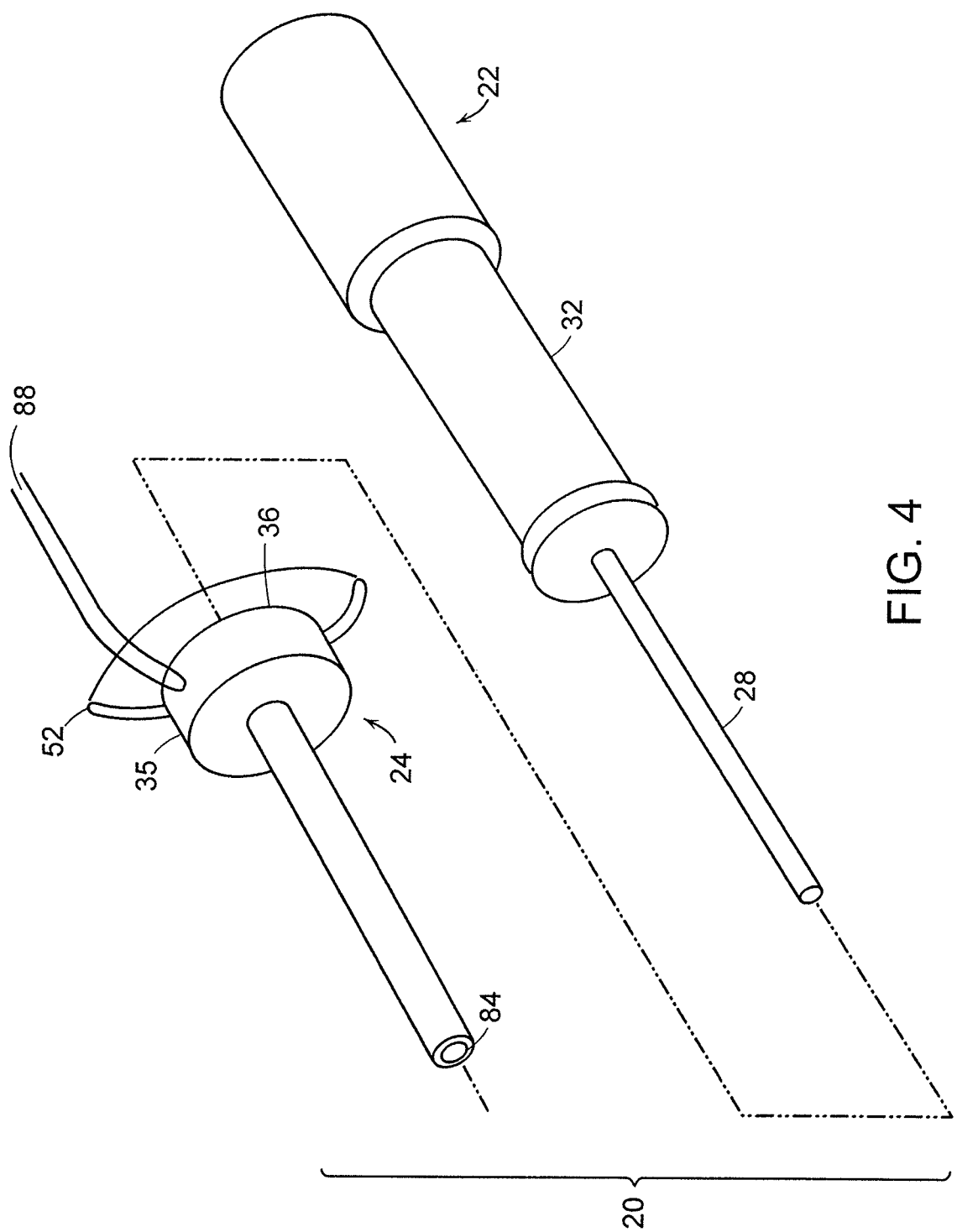
FIG. 4 is a perspective view of the miniature endoscope.

With the method of inserting the endoscope 20 into the cannula 60 to have the distal end of the endoscope 20 at the proper location, previously described, the endoscope 20 is described in further detail. Referring to FIG. 4, a perspective view of the endoscope 20 is shown. The endoscope 20 has the reusable imaging unit 22 and the disposable sheath/illuminator unit 24. The disposable sheath/illuminator unit 24 has a elongated tube for overlying and encircling the elongated tube 28 of the imaging unit 22. The elongated tube of the sheath/illuminator unit 24 has a sealed distal end 84 and several embodiments include fiber optics for transmitting the illumination from a external light source 40, such as seen in FIG. 1, to the distal end 84. At the proximal end of the sheath/illuminator unit 24 is a base 35 with a mounting mechanism 36 for securing to the imaging unit 22 of the endoscope 20. An optical pigtail 88 projects from the base 35 for connecting to the light source 40. In addition, the sheath/illuminator unit 24 has a drape 52 which is mounted to the base 35 and is extended over the handle 32 of the imaging unit 22. The handle 32 of the imaging unit 22 contains optics and the imaging device 32 to receive the image transmitted through the optical fibers 26 located in the elongated tube 28 of the imaging unit 22 as described in further detail below with respect to FIGS. 9-11.

Figure 5:
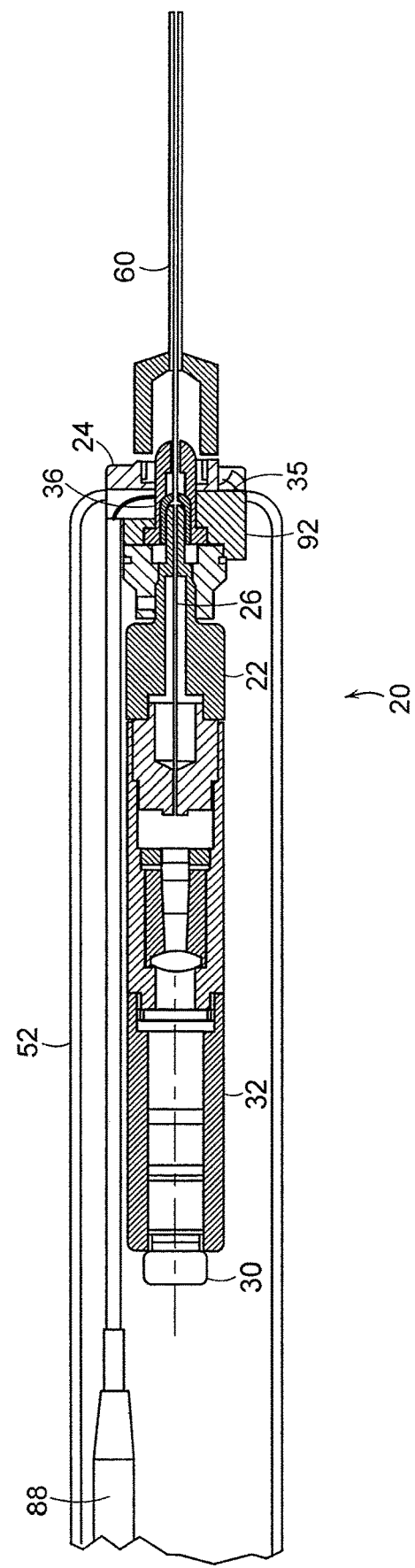
FIG. 5 is a sectional view of the miniature endoscope with a cannula overlying the disposable sheath.

FIG. 5 is a sectional view of the miniature endoscope 20 including the reusable imaging unit 22 with imaging an optical fiber 26 and the disposable sheath/illuminator unit 24. The cannula 60 is shown overlying the disposable sheath 34 of the sheath/illuminator unit 24, which overlies the probe 29 of the imaging unit 22.

As seen in FIG. 5, the reusable imaging unit 22 of the endoscope 20 is encircled by the disposable sterile sheath/illuminator unit 24. The disposable/sheath illuminator unit 24 has the disposable sheath 34 that is sealed at the distal end 84 and encircles and surrounds the elongated tube 28 carrying the optical fibers 26 of the imaging unit 22. The mounting mechanism 36 on the base 35 of the sheath/illuminator unit 24 is secured to a mounting mechanism 92 on the imaging unit 22.

The disposable sheath/illuminator unit 24 has the drape 52 which surrounds the handle of the imaging unit 22. In addition, the sheath/illuminator unit 24 has the illumination pigtail connecting to a light source 40 as seen in FIG. 1. The illumination pigtail 88 is optically coupled to the optical fibers in the sheath as explained in further detail below.

Referring to FIG. 6A, a side view of the sheath/illuminator unit 24 is shown. The sheath unit 24 has the disposable sheath 34 with an elongated outer sheath 98 which extends from the base 35 to the distal end 84. The illuminator pigtail 88 extends from the base and is optically coupled to illumination fibers 116 within the sheath 34 as seen in FIG. 7A. The drape 52 is carried by the base 35 of the sheath/illuminator unit 24 for overlying the handle 35 of the imaging unit 22 when the two units 22 and 24 are combined.

FIG. 6B is an enlarged view of the distal end 84 of the disposable sheath 34 of the sheath/illuminator unit 24. The disposable sheath 34 has the outer sheath 98 which extends from within the base 35, as seen in FIG. 6A, and serves as protective covering and a sterile barrier for the sheath unit 24. Spaced and collinear with the outer sheath 98 is an inner tube 100 of the disposable sheath 34. The inner tube 100 defines a cylindrical void on space 102 for receiving the elongated tube 28 of the probe 29 of the imaging unit 22. The inner tube 100 likewise from the distal end 84 of the disposable sheath 34 to the base 35 of the sheath/illuminator unit 22. The inner tube 100 extends further than the outer sheath 98 to create a channel 106 to receive a plurality of illumination fibers 108 as best seen in FIGS. 6A and 7A. At the distal end, of the inner tube 100 is located a window 110 which is secured to the inner tube 100 to make a sterile 84 barrier between the airspace 102 for receiving the elongated tube 28 of the image unit 22 and the outer portion of the sheath/illuminator unit 24 which is in contact with the body.

In a preferred embodiment, the outer sheath 98 of the disposable sheath 34 of the sheath/illuminator unit 24 is made of a stainless steel material and has an outer diameter of about 0.038 inches. The inner tube 100 is likewise made of a stainless steel material. The illumination fibers 108 are made of a glass or plastic fiber. Depending on the size of the device, the maximum number of illumination fibers 108 is used to fill channel 106. In one example, the disposable sheath 34 extends 2.246 inches from the base 35 of the sheath/illuminator unit 24.

Figure 7B:
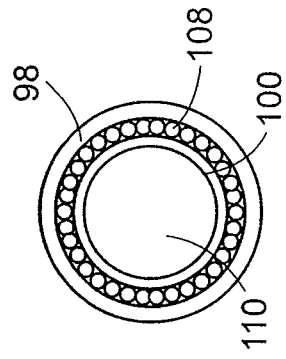
FIG. 7B is a front view of the distal end of the disposable sheath taken along the line 7B-7B of FIG. 6A and FIG. 6B.
Figure 7A:
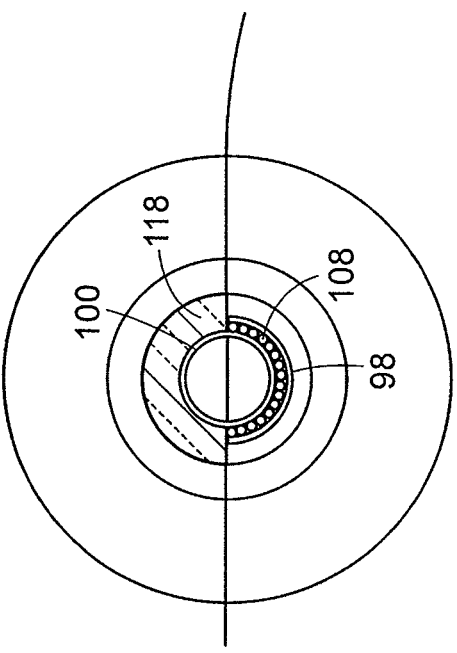
FIG. 7A is a sectional view of the proximal end of the disposable sheath/illumination unit taken along line 7A-7A of FIG. 6A.

Interposed between the outer sheath 98 and the inner tube is the plurality of illumination fibers 108 which encircle the inner tube 100 as best seen in FIGS. 7A and 7B. FIG. 7A is a sectional view through the base 35 of the disposable sheath 24. The outer sheath 98 is shown in the lower half of FIG. 7A and terminates prior to the portion sectioned in the upper half of FIG. 7A. The inner tube 100, however, which defines the airspace 102 to receive the elongated tube 28 of the imaging unit 22 extends to a receiving chamber 114 as seen in FIG. 6A and therefore is shown in both the upper and lower portions of FIG. 7A. The light is transmitted from the illumination pigtail 88 through fibers 108, as seen in FIG. 6A, to a transmission unit 118 as seen in the upper half of FIG. 7A which abuts the illumination fibers 108 located between the outer sheath 98 and the inner tube 100 of the disposable sheath 34 of the sheath/illuminator unit 24.

FIG. 7B shows the distal end 84 of the disposable sheath/illumination unit 24. The window 110 overlies and seals the airspace 102 that receives the imaging unit 22 and is encircled by the inner tube 100. Interposed between the outer sheath 98 and the inner tube 100 is the plurality of illumination fibers 108. In the embodiment shown, the distal end of the illumination fibers 108 are not protected and are exposed to the body.

Figure 8:
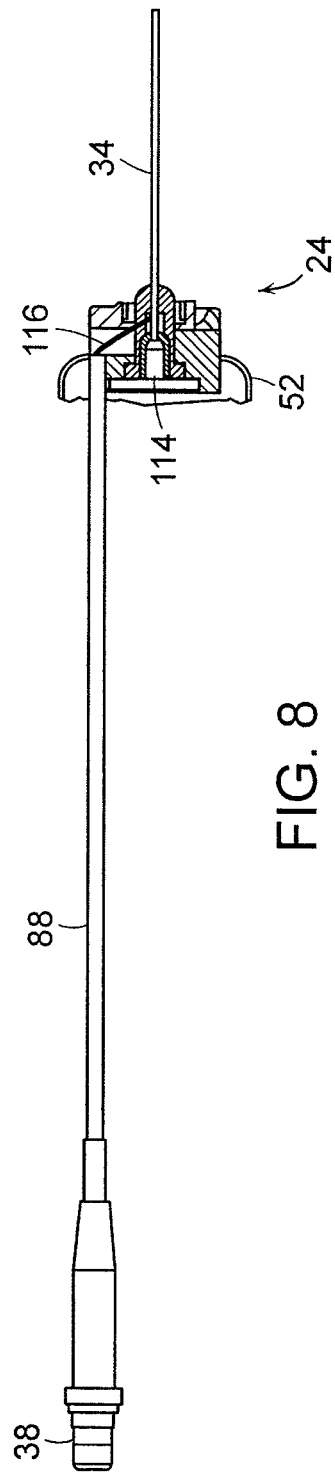
FIG. 8 is a side view of the disposable sheath/illumination unit showing the illumination pigtail.

FIG. 8 is similar to FIG. 6A in that it shows the disposable sheath/illumination unit 24. In addition, FIG. 8 shows the entire illumination pigtail which is broken away in FIG. 6A.

The illumination pigtail 88 has a connection 38 for connecting to a connector on the light source 40. The illumination pigtail 88 has a plurality of optical fibers which run from the connection 38 to the fibers 108 which transmit the light received from the light source 40 to the transmission unit 118 shown in FIG. 7A and exit at 84.

Referring to FIG. 9, a sectional view of the imaging unit of the endoscope 20 is shown. The imaging unit 22 has the probe 29 with the elongated tube 28 that extends from the handle 32. At the proximal end of the handle 32, is the imaging device. In this embodiment, a charged coupled device (CCD) 30B which converts the optical image into an electrical image is carried in the detachable housing 120A of the handle 32. Interposed between the optical fiber or fibers 26 which extend in the elongated tube 28 and the CCD 30B is a plurality of lenses 122A for projecting the image of the proximal end 124 of the optical fiber or fibers 26 to the CCD 30B. The glass window 122B is attached to housing 120B and provides a seal to the scope. It also protects the lenses from contamination.

The imaging unit 22 enlarges the image from the end of the fiber optic 26 and couples it to the charged coupled device 30B. As indicated above, the charged coupled device is connected to a electronic storage and/or display device such as a computer 44 which is connected to a monitor 46 as seen in FIG. 1.

The handle 32 of the imaging unit 22 has a mounting mechanism 128 for coupling with the mounting mechanisms 36 of the sheath illuminator unit 24. The mounting mechanism 128 has slots 130 for receiving pins located on the mounting mechanisms 36. In addition, the mounting mechanism 128 has a projection 134, from which the probe 29 projects, that is received by the receiving chamber 114 of the sheath/illuminator unit 24 as seen in FIG. 6A.

An enlarged view of the distal end of the imaging unit 22 is shown in FIG. 10A. The rod tip 29 of the imaging unit 22 has the elongated tube 28 that extends from the distal end 126 to the housing 120 of the handle 32. At the distal end 126 of the rod tip 29 there is in addition a tube 138 which extends a slight distance from the distal end 126 and just a slight distance beyond the ends of the optical or image fibers 26. The tube 138 is commonly referred to as the long tube in that a shorter and smaller diameter tube 140 which is collinear with the long tube 138 is received within the long tube 138 and extends a lens system 142 at the distal end 126. The elongated or outer tube 128, long tube 138 and small tube 140 are mounted so that their distal ends are flush and are secured by an adhesive such as a medical grade epoxy. At the end of the elongated tube 28 of the imaging unit 22 is the lens system 142 that is described in further detail below. The elongated tube 28 of the imaging unit 22 is received within the disposable sheath/illumination unit 24 and therefore does not need to be sterilized prior to the first use.

FIG. 10B is an end-view of the distal end 126 of the imaging unit 22. The lens system 142, the small tube 140, the long tube 138 and the outer or elongated tube 28 are shown and are all collinear.

Figure 11:
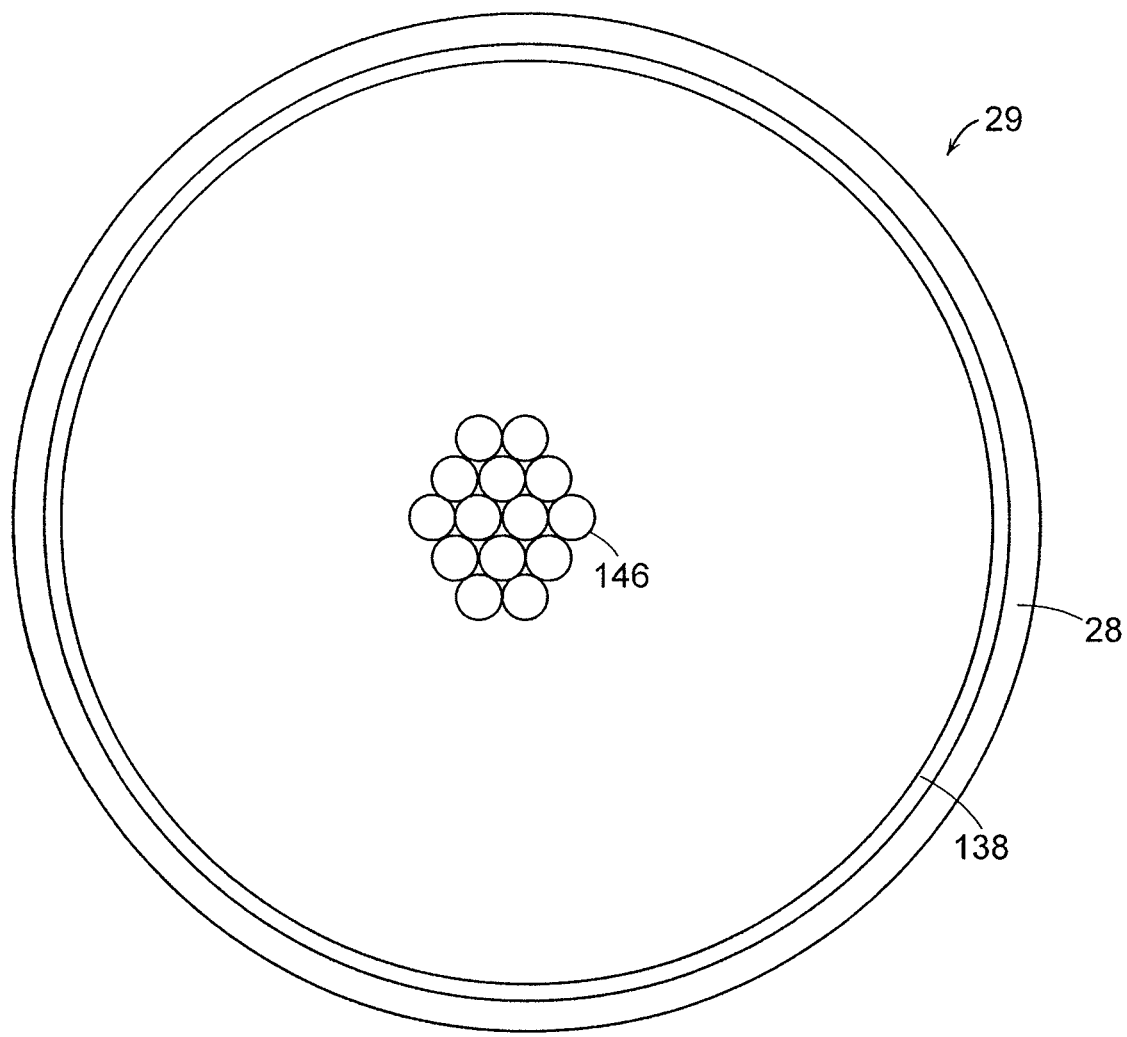
FIG. 11 is a schematic of an enlarged partial sectional view of the imaging unit taken along the line 11-11 of FIG. 10A.

Referring to FIG. 11, a sectional view of the imaging unit 22 of the endoscope 20 is shown. The probe 29 of the imaging unit 22 has a plurality of fibers 146 for transmitting the image from the distal end 126 of the rod tip 29 to the handle 32. Encircling the fiber 146 at the distal end of the rod tip 29 is the long tube 138 for holding the fibers 146 of the image fibers 26 in position. The outer or elongated tube 28 encircles the long tube 138 and protects the fibers 146 of the image fibers 26 from their beginning near the distal end 126 of the rod tip 29 to the other end within the handle 32. There are typically thousands of fibers 146 as shown in FIG. 11 that are fused together. The loading of the image into them is done by the distal end lens system 142 which as described below arranges the light levels of the image in a relationship to the location of the image fiber bundle 26.

In addition, the fibers are arranged in a disorder pack method. This disorder pack method limits transmission of images/light from one lens 142 to another as the image fiber bundle 26 extends from near the distal end 126 of the imaging unit 22 towards the proximal end of the fibers located within the handle 32. The disorder packing of fibers is achieved by varying the doping of the fibers, which is the subject area to be examined hereinafter.

Figure 12:
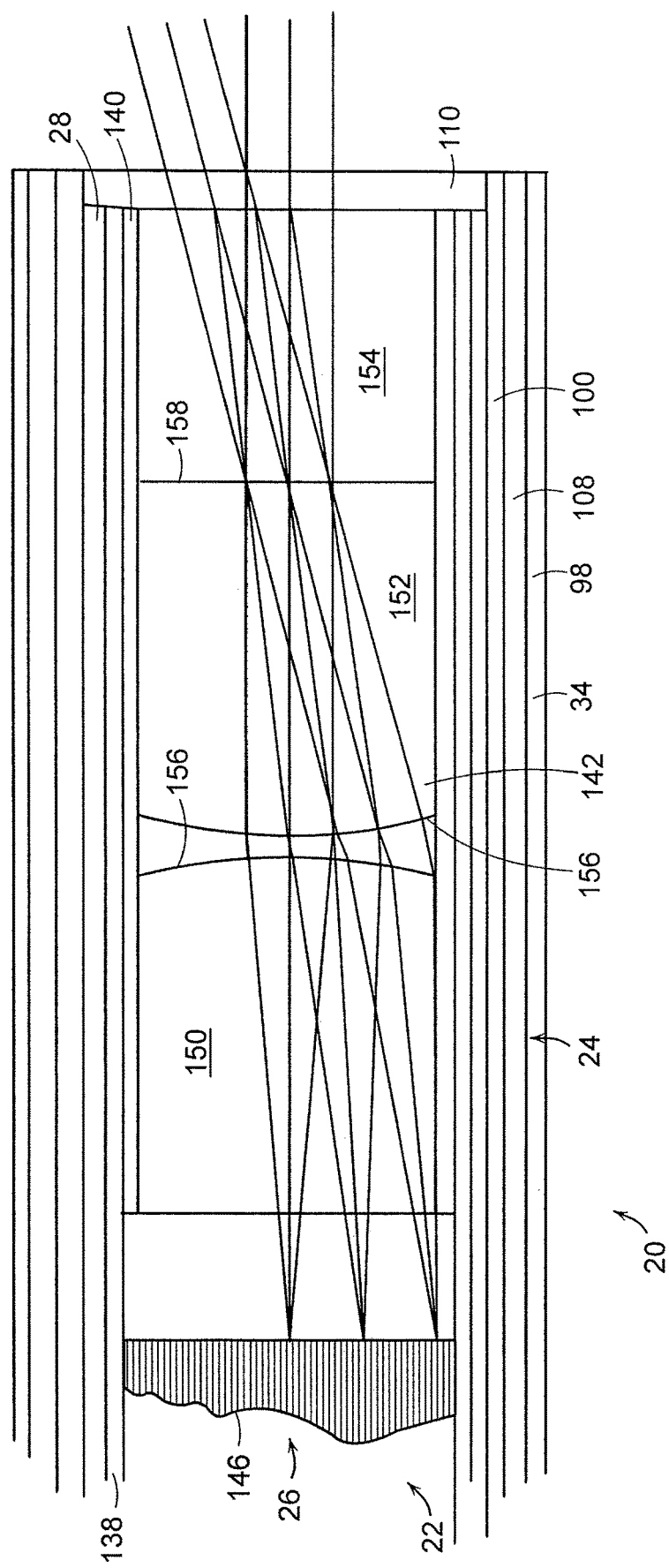
FIG. 12 is an enlarged view of the distal lens system.

Referring to FIG. 12, a sectional view of the distal end of the rod tip 29 of the imaging unit 22 within the disposable sheath 34 of the sheath/illuminating unit 24 is shown. The disposable sheath 34 has the outer sheath 98 collinear with the inner tube 100. Interposed between the outer sheath 98 and the inner tube 100 is the plurality of illumination fibers 108 as best seen in FIG. 7B for illumination. At the distal end of the disposable sheath is the window that is secured, such as by cementing, to create a boundary to the air space or inner channel 102 that receives the rod tip 29 of the imaging unit 22. The imaging unit 22 has the elongated or outer tube 28 that extends from the distal end 126 to within the handle 32 as shown in FIG. 9. Located in the distal end 126 of the rod tip 29 are two additional tubes or sleeves, the shorter inner sleeve, referred to as the small tube 140, that retains and holds the lens elements of the distal lens system 142. A larger longer sleeve, referred to as the long tube 138, encircles the tube 140 and the beginning of the fibers 146 of the image fibers 26.

The distal lens system 142 as shown in FIG. 12 is an achromatic lens system having a pair of lenses 150 and 152 and an aperture stop 154. The lenses 150 and 152 each have a convex surface 156 that face each other. The second lens 152, closer to the distal end 126, has a planar surface 158 which abuts the optical aperture stop 154. The aperture stop 154 and the lenses 150 and 152 are designed so that the sine of the maximum ray angle approaches the fibers at N.A. (numerical aperture).

The ray tracings 160 in FIG. 12 illustrate the projection of an image off the page to the right at the proper focal length and how this image is translated through the aperture stop 154 and through the lenses 152 and 150 to the plurality of fibers 146 in the image fibers 26. The lens system is non-telecentric.

Figure 13:
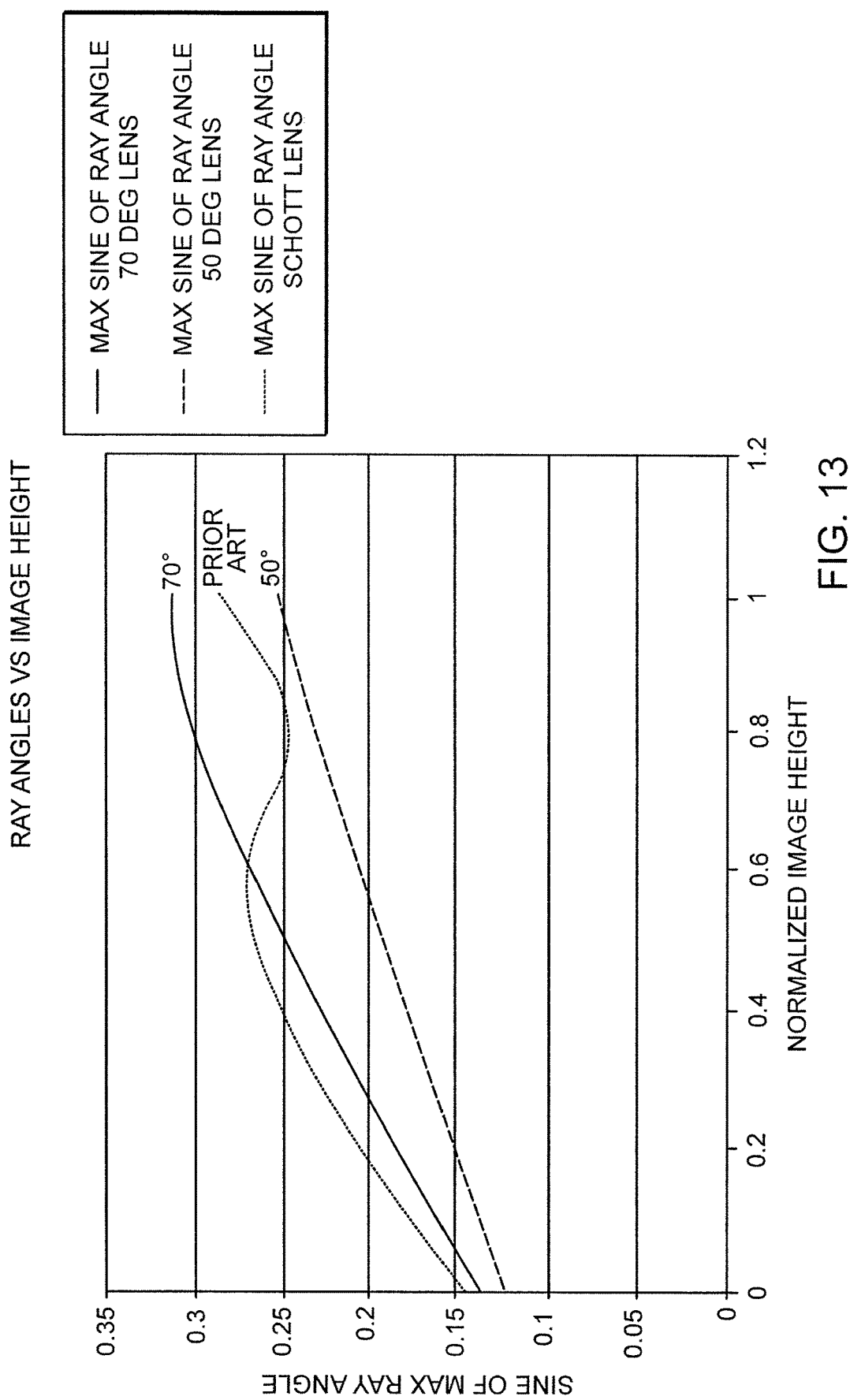
FIG. 13 is a graph of the sine of the maximum ray angle versus normalized image height for different lens systems for the distal end of the endoscope.

Referring to FIG. 13 a graph of the sign of the maximum ray angle versus the normalized image height for three different lens systems including a prior art lens system is shown. As discussed below, the field of view is dependent upon the lens configuration. The graph in FIG. 13 shows a line for the maximum sign of a ray angle for a 50 degree lens system and a second line for a maximum sign of ray angle of a 70 degree lens system. In the 70 degree system, the maximum sign is approximately 0.32. Therefore, the N.A. (numerical aperture) of the fiber is approximately the same. In contrast, the 50 degree field of view system has a sign of a maximum ray angle of approximately 0.25. Therefore, the fibers have this numerical aperture. The system can provide a field of view at any selected level from 30-80 degrees, for example.

In one embodiment, the endoscope 20 has 10,000 fiber elements. In this embodiment, each fiber element 146 has a diameter of 4.4 microns. The overall diameter of the fiber 26 is 0.46. The elongated or outer tube 28 of the imaging unit is made from stainless steel. It is recognized, that the scope can be formed in many sizes, the following table is merely an illustration of various intervening size scopes.

The grin lens 168 in general does not provide preferred image quality as that of the acromat lens system 142 described above in that the image becomes less clear (i.e., blurry and distorted) towards the edge of the image. In addition, the color correction, changes in intensity as a function of wavelength, is not as good as in the acromat lens system. However, the GRIN lens system 168 maybe desirable in situations where cost is a higher factor than the overall image quality. In addition, because of the grin lens 170 being a single element lens the depth of field may be limited. While only 2 different degrees of freedom are shown, it is recognized that lens systems with other fields of view can be made.

Figure 15:
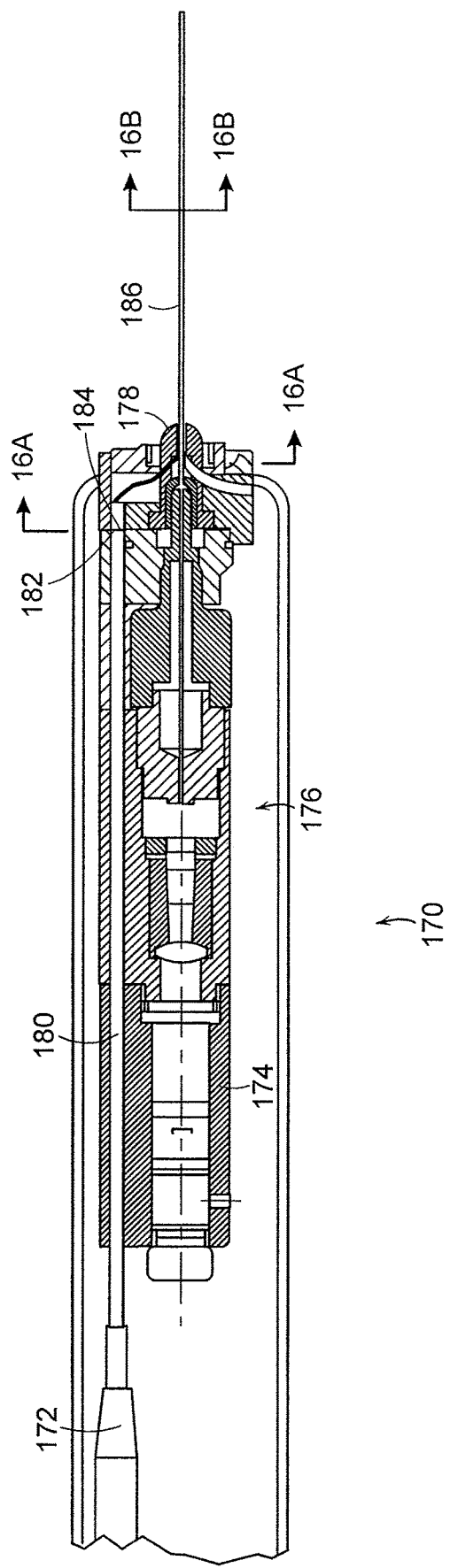
FIG. 15 is a sectional view of another embodiment of an endoscope.

FIG. 15 is a sectional view of alternative endoscope 170. In this embodiment of the endoscope 170, the illuminator pigtail 172 is a part of the handle 174 of the imaging unit 176 and is therefore not part of a disposable sheath/illuminator unit 178. An optical fiber bundle 180 is used for transmitting the illumination light from the pigtail 172 to a handle interface 182 in the handle 184 where the light is transferred to a light interface 184 on the sheath/illuminator unit 178 to transmit light from the handle 184 to the disposable sheath 186.

FIG. 16A is a sectional view showing the interface. FIG. 16A is a sectional view of the base 188 of the disposable/sheath illuminator unit 178. The upper portion of FIG. 16A shows the drape 52 spaced from the base 188. The base 188 has a light interface 184 that receives light from the handle interface 182 carried on the handle 174.

In addition in the embodiment of the endoscope 170 shown in FIGS. 16A-16C, the sheath/illuminator unit 178

|  | 3k | 10k | 30k | 50k | 100k |
|---|---|---|---|---|---|
| Sheath/ Illumination unit outer diameter | 1-4 mm | | | → | |
| Imaging Unit rod tip outer diameter | 0.5-3.5 mm | | | → | |
| No. of fiber elements | 3,000 | 10,000 | 30,000 | 50,000 | 100,000 |
| Fiber image diameter | | 0.46 mm | 0.75 mm | | |
| Fiber pixel size (individual fiber) | 4.4 microns | 4.4 microns | 4.4 microns | | |
| Lens Type | Achromatic or Selfoc Grin | Achromatic or Selfoc Grin | Achromatic | Achromatic | Achromatic |
| Depth of Field (DOF) | | 3 mm-20 mm | | → | |
| Field of View (FOV) | Dependent on Lens 50°-70° | | → | | |

Figure 14:
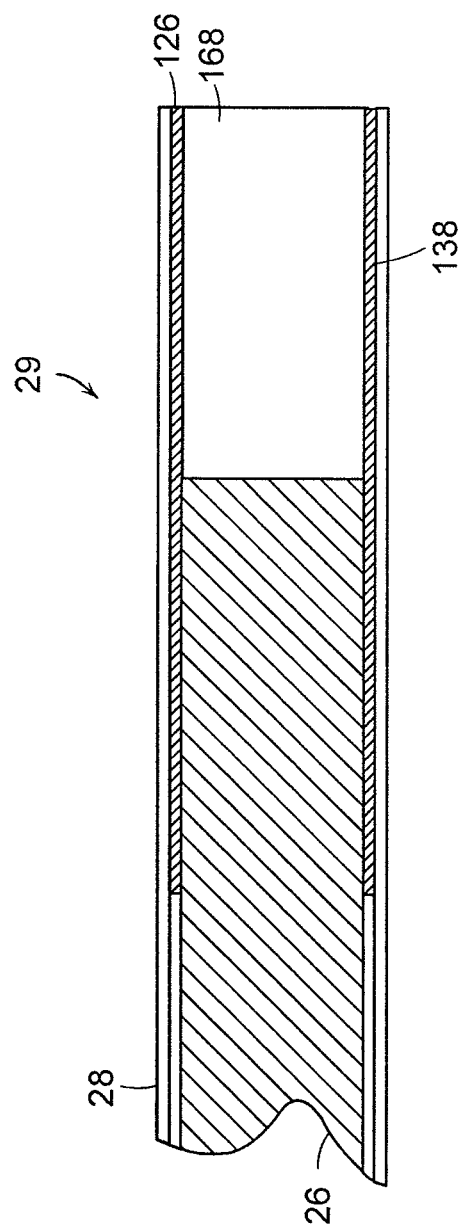
FIG. 14 is an enlarged view of another embodiment of a distal lens system.

As can be seen from table above, an alternative to an acromat lens described above with respect to FIGS. 12 and 13 is a selfoc grin lens. FIG. 14 shows an alternative embodiment of the rod tip 29 of the imaging unit 22 of the endoscope 20 with a grin lens 168. The grin lens 168 as shown in FIG. 14 is a single element gradient index lens. The rod tip 29 of the image unit 22 as shown in FIG. 14 has an elongated or outer tube 28 that extends from the distal end 126 to the handle 32. In addition, similar to that of FIG. 10A, a tube 138 extends a slight distance from the distal end 126. This tube 138 is commonly referred to as the long tube, it extends just slightly beyond the ends of the optical image fibers 26. In contrast to the embodiment shown in FIG. 10A in that the lens 170 is a single lens there is no need for a small tube 140 for retaining the elements of a lens system.

has one of the illumination fibers 190 replaced by a tube or channel 192. The tube 192 which is seen in FIGS. 15 and 16A-16C is capable of receiving a laser fiber. The user passes a laser fiber though the tube 192 from the proximal end of the illumination unit 178 in the base 188 as seen in FIG. 15, to the distal end of the illumination unit so that the user while viewing the image through the imaging fibers and CCD can complete a process using the laser fiber.

The lower half of FIG. 16A shows a cross-sectional view through the base 188 of the sheath/illuminator unit 178 in which the tube 192 extending through the base into the annular ring containing the illumination fibers 190. Similar to that shown in FIG. 7A, FIG. 16A shows an inner tube 194 around which the illumination fibers 190 are located. The inner tube 194 defines an airspace through which the probe 29 of the imaging unit 176 of the endoscope 170 passes.

FIG. 16B is a sectional view of the disposable sheath 186 showing an outer tube 196 of the disposable sheath 186 circling the illumination fibers 190 and the tube 192. The inner tube 194 surrounds the airspace 102 which receives the probe 29 of the imaging unit 176. FIG. 16C is an enlarged view showing the tube 192 with its opening to receive the laser fiber in the annular ray containing the illumination fibers 190 between the inner tube 194 and outer sheath 196. While FIGS. 15-16C do not show a cannula 60, it is recognized in most uses of the endoscope 20 or 170, a cannula 60 can be used for extra protection of the endoscope 20 or 170.

Illustrated in FIG. 16 D-L is a disposable sheath and imaging assembly for a preferred embodiment of small diameter endoscope. FIG. 16D shows the disposable sheath 300 including the tubular portion 304 for insertion into the body, a base or hub assembly 302, which includes a sheath housing element 314 that is attached to the proximal end of tubular portion 304, a cannula connector 312 that snaps onto a proximal connector of the cannula described above. The sterile barrier 306 is attached to element 314 at the distal end of the barrier. The base 302 further includes a connector assembly 305 that is attached to housing element 314. The connector assembly can include an optical coupler 310 that optically connects the illumination fiber bundle 316 to a light source when the imaging device assembly 340, shown in FIG. 16E, is inserted into the sheath to provide the assembled endoscope 357 that is ready for use, as shown in FIG. 16F. The optical coupler 310 is thus positioned within the sterile barrier 306. The assembly 340 includes a first connector 346 that connects to the optical coupler 310 that can plug into the connector 346. Additionally, a second connector 344 on assembly 340 serves to mechanically attach the assembly 340 to a coupling element 308 positioned within connector assembly 305. Thus, to assemble the device for use as shown in FIG. 16F, the user grasps the handle portion 349 of element 340 and inserts the distal tip of tubular sheath 342 through the aperture 318 in the connector assembly at coupling element 308, and through a proximal opening 311 in the proximal end of tubular sheath 304. The first connector 346 and second connector 344 engage the optical coupler 310 and coupling element 308, respectively, substantially simultaneously.

Figure 16H:
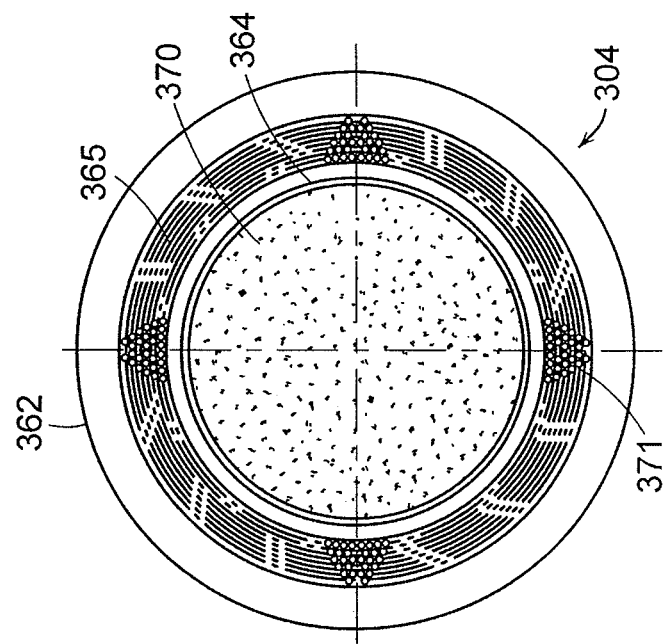
Figure 16G:
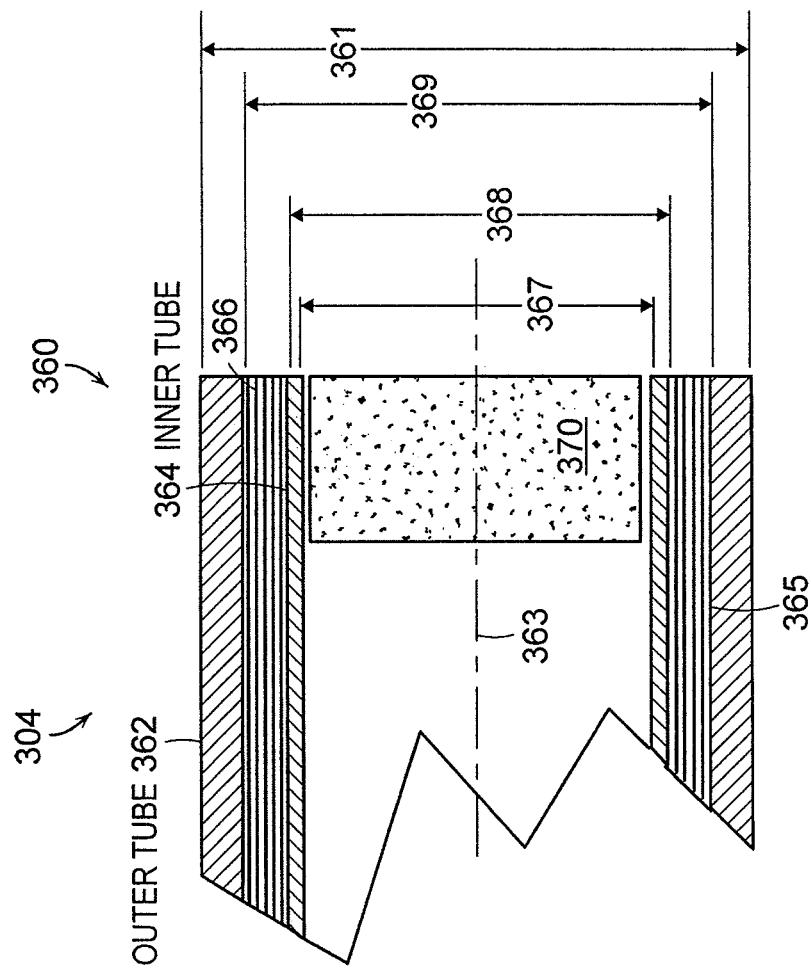
Figure 16I:
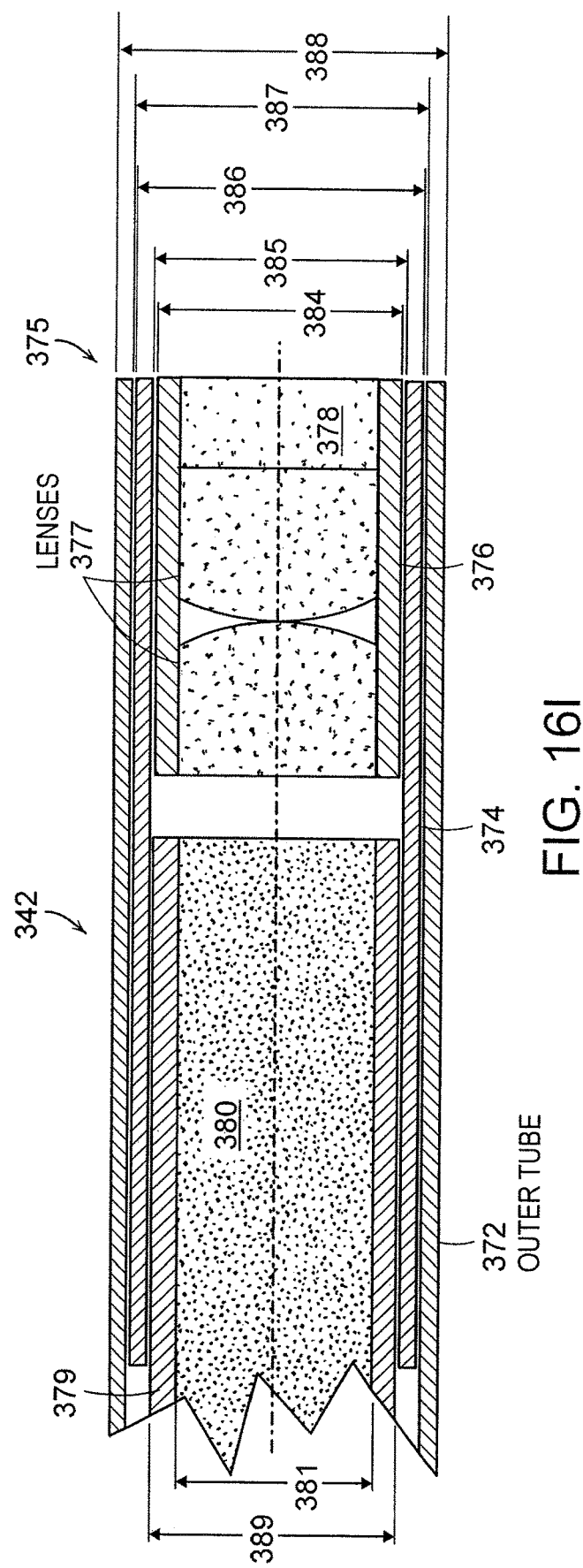
Figure 16J:
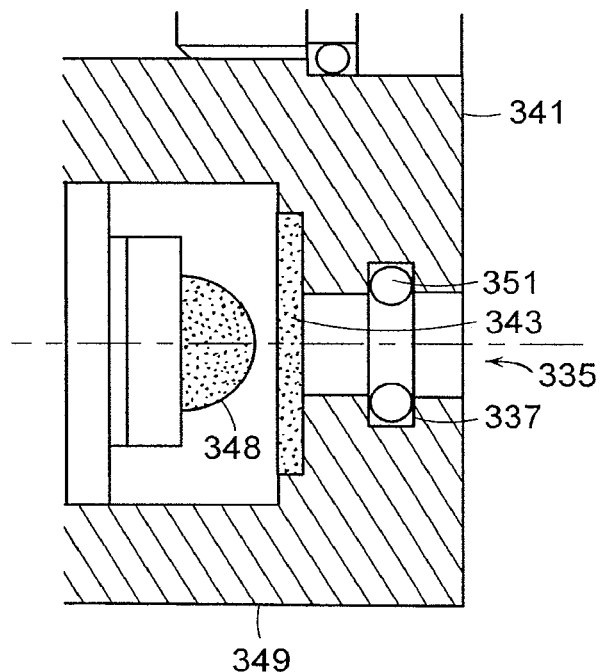
Figure 16K:
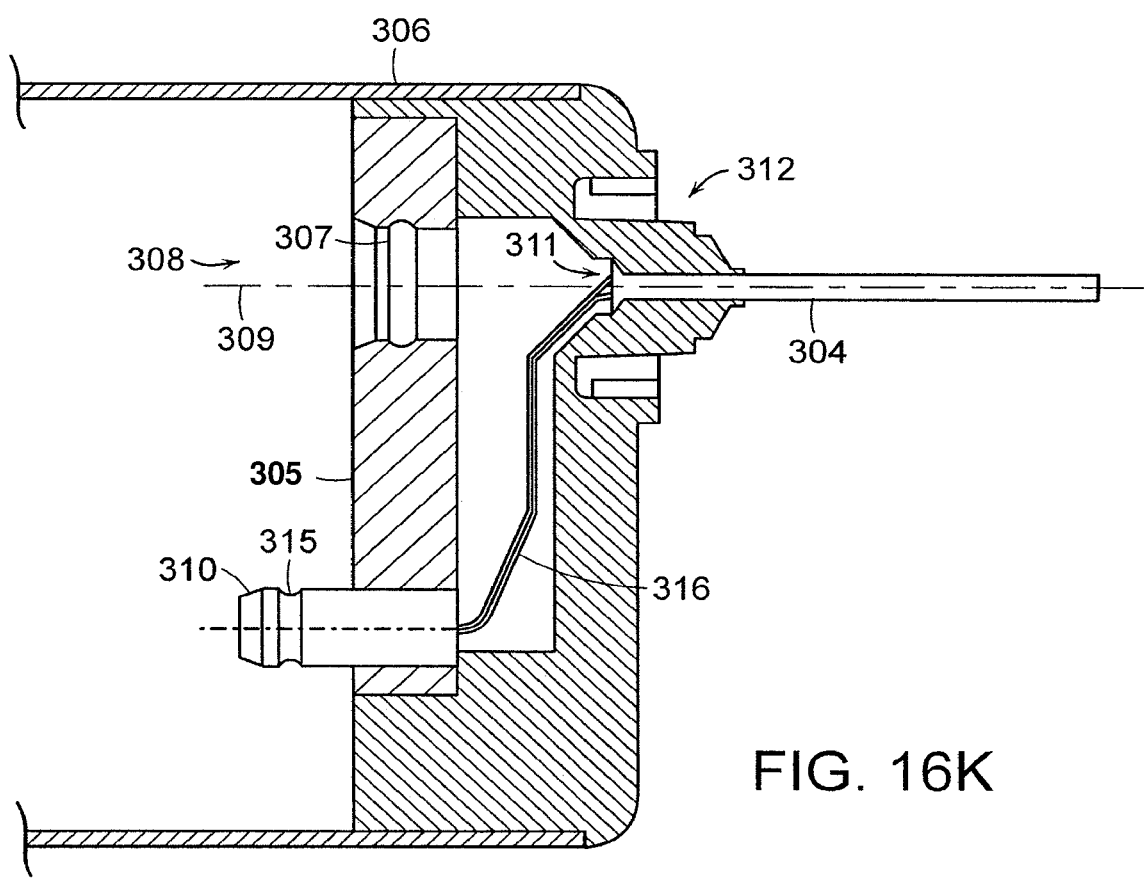
Figure 16L:
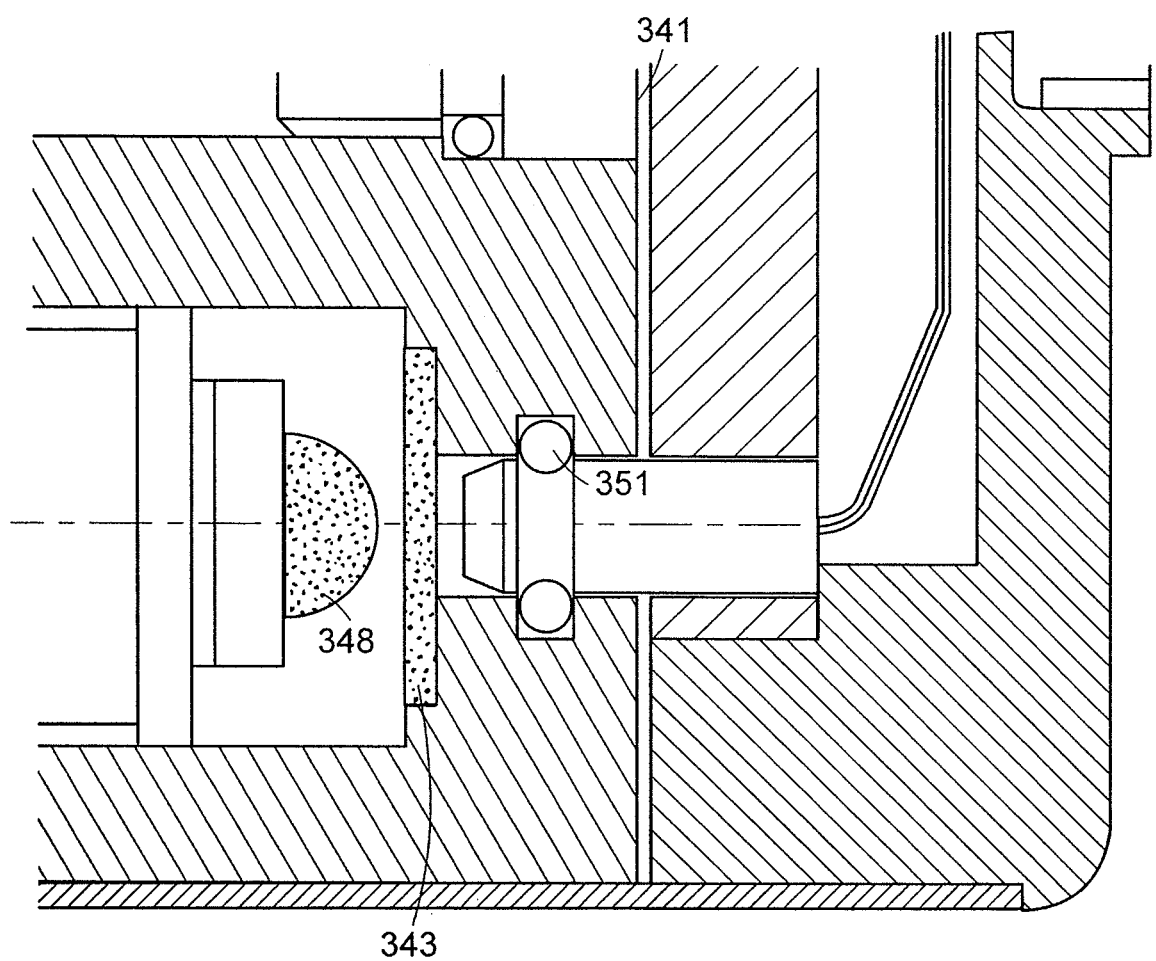

As shown in the enlarged view of FIGS. 16J-16L, the optical coupling can be inserted through an opening 335 in the distal surface 341 of handle 349. The distal surface can be generally circular or oval in shape and have a diameter of 2-8 cm to easily fit within the hand of a user. The coupling can use an o-ring 351 that fits within an o-ring groove 337 on the inside wall of opening 335. The o-ring 351 comes to rest in the o-ring groove 315 of coupler 310 to provide an optical coupler seal as shown in FIG. 16K. The proximal face of coupler 310 can comprise the polished proximal end of optical fiber bundle 316 which receives light through sealed window 343 from light source 348 which can be an LED or laser diode. Examples of white light LEDs suitable for imaging for many applications of the present invention are available from the American Opto Plus LED Corp., Pomona, Calif. Two or more different light sources having white, broadband or monochromatic emission spectra can be coupled to different optical fibers of bundle 316 so that the user can selectively illuminate a region of interest with different wavelengths or bands of light for imaging and/or spectroscopic analysis. The light source 348 can be powered by batteries 350 which can be inserted into the handle 349 by removing cap 345. Imaging device 352 can be a CCD or CMOS imaging sensor within electronics module 354 which can include processing, control and wired or wireless connection as described elsewhere herein.

The optical relay described previously is located in optical housing 347 to couple light from the imaging channel to camera 352. The o-ring 332 on connector 344 fits within groove 307 after the tube 342 is inserted along axis 309 through openings 318 and 311 to provide an optical relay seal. Thus, coupler 310 provides a first fluid tight seal to the handle and coupling element 308 provides a second fluid tight seal to the handle.

The distal end 360 of tubular sheath 304 is shown in enlarged partial cross-sectional and end views of FIGS. 16G and 16H, respectively. The sheath can include an outer tube 362, inner tube 364 co-axially mounted thereto about longitudinal axis 363, optical fibers 365 that fit within the cylindrical cavity between the outer and inner tubes. The fibers 365 have a packing factor of at least 80%, and preferably over 85%, in order to provide good coupling and distribution of light from the light source 348 across a large field of view. An adhesive 366 is used to bond the distal ends of the fibers together and to the inner and outer tubes. During manufacture, the adhesive can be applied to the portion of the fibers extending out of cylindrical cavity between the inner and outer tubes, then the fibers are gently pulled in the proximal direction so that the adhesive covered walls of the fibers are pulled between the inner and outer tubes for at least 2 mm. The distal ends of the fibers are cut and polished to provide a single optical illumination surface.

It is desirable in a small diameter endoscope to provide a large field of view with sufficient illumination distributed evenly across the field of view to provide a diagnostically useful image at a given depth of field. Thus the ratio of area occupied by the distal illumination area $I_A$, formed by the area occupied by the distal ends of the illumination fibers 365, to the area of the window 370, or light collection area $C_A$, through which the image is collected becomes an important metric in defining the imaging characteristics of small diameter endoscopes of less than 3 mm in diameter. Generally, the smaller the device, the more critical this ratio becomes. By using small diameter optical fibers, the packing factor of the optical fibers can be increased, thus providing more efficient use of the illumination area.

As shown in FIG. 16H, the individual fibers, shown in the quadrants 371, extend completely around the circumference, and can have from one to ten rows of fibers, for example. Optical fibers having diameters of 30 microns to 50 microns can be used, for example, to more fully use the available volume. When 30 micron optical fiber is used, between 500 and 1000 optical fibers can be used depending on the size of the cylindrical volume between the inner tube 364 and the outer tube 362. In a preferred embodiment, the outer diameter 361 of outer tube 362 is 1.7 mm and the inner diameter 369 of outer tube 362 is 1.45 mm. The inner tube 364 has an outer diameter 368 of 1.17 mm and an inner diameter 367 of 1.072 mm. In this embodiment, there are between 600 and 800 optical fibers that results in an illumination area of about 0.575 mm². The window has a diameter of about 1.07 mm and an area of about 0.9 mm². Thus, the ratio $I_A/C_A$ is about 0.64. The ratio is preferably between 0.5 and 1.0 but can be as high as 2.0 for certain applications.

Figures 1, 16P:
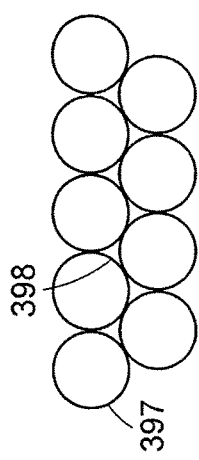
FIGS. 16M-P illustrate cross-sectional and end views of disposable components in accordance with the invention.
Figure 16P:
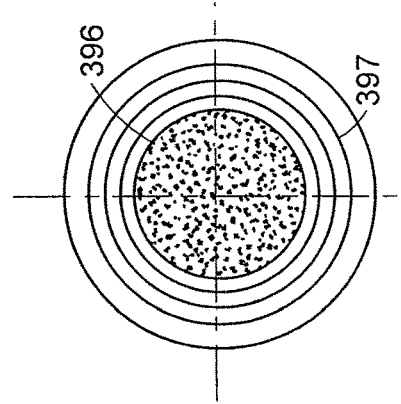
Figure 16M:
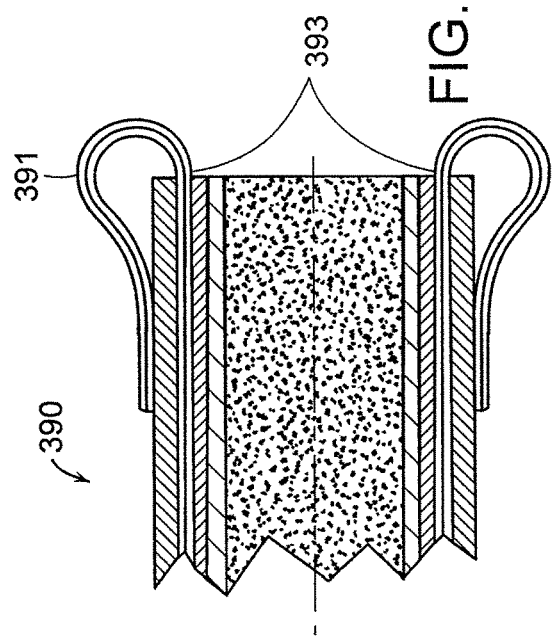

Shown in FIG. 16M is a cross sectional view of a sheath 390 during manufacture in which the ends of illumination fibers 391 are bent of splayed. After application of the adhesive to attach the fibers to the tubes of the sheath 390, the distal ends of the fibers are cut off and the surfaces 393 polished. Instead of a circular end, however, the distal end 392 of each fiber has a somewhat oval or noncircular shape 394, as seen in FIG. 16N, that alters the angle at which light exits the fiber and can increase the filed of view by 5-10 degrees.

Figure 16O:
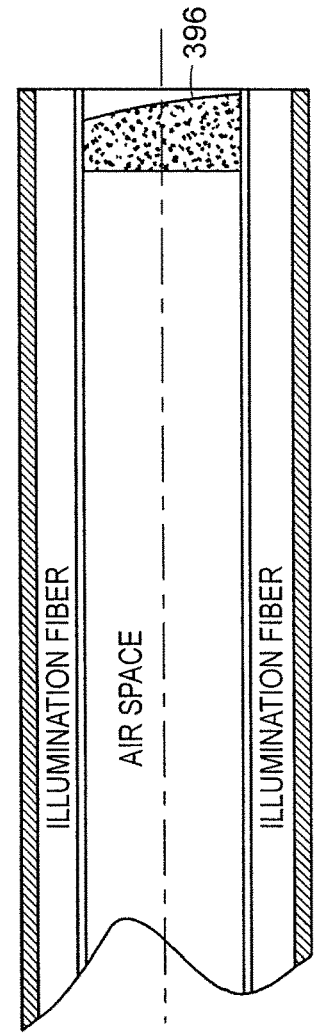
Figure 16N:
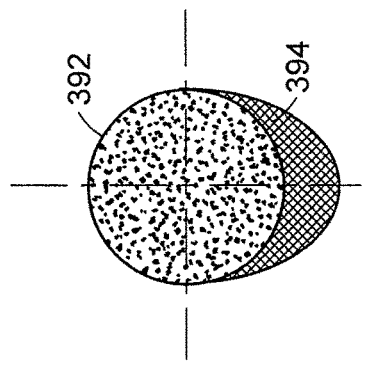

Instead of a window at the distal end of the sheath 395, a prism 396 can be added as shown in FIG. 16O. The prism 396 can shift the field of view by 1-10 degrees, for example. Alternatively, a prism with a face angled at 10-30 degrees can be inserted and attached to the inner tube of the sheath with an adhesive layer to provide side viewing at a greater oblique angle. In another embodiment, the prism can be attached to the distal end of the imaging channel and a sheath having an angled window conforming to the shape of the prism which can be used with a lens or prism mounted on the distal end of the illumination fibers, or the distal ends of the fibers can be angled within the sheath to provide the desired illumination area at the desired angle. FIG. 16P shows the prism 396 and the surrounding illumination fibers 397 which have a small diameter, preferably in a range of 30-50 microns, so as to reduce the interstitial spacing 398 between the adjacent fibers to provide the desired packing factor of at least 80%.

Figure 17A:
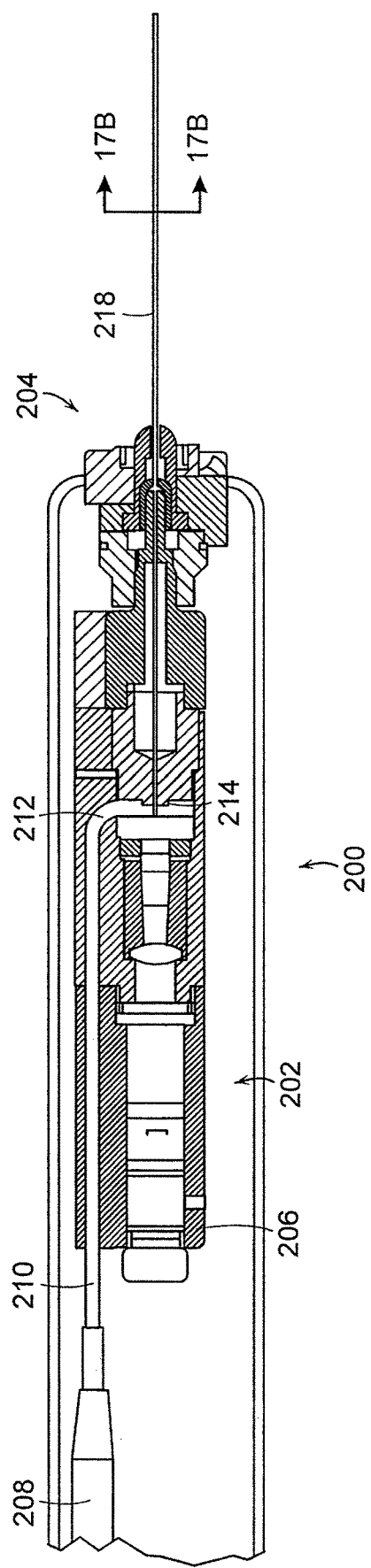
FIG. 17A is a sectional view of another embodiment of an endoscope.

Referring to FIG. 17A, a sectional view of an alternative endoscope 200 is shown. The endoscope 200 has an imaging unit 202 and a sheath unit 204. In contrast to the previous embodiments, the sheath 204 that is disposable does not include any part of the illumination unit. Referring to FIG. 17A, the illumination source 40 is connected to the handle 206 of the imaging unit 202 by an illumination pigtail 208 similar to that shown in FIG. 15. But in contrast, there is no coupling such that the light is transmitted to the disposable sheath 204. Rather, as seen in FIG. 17A, the illuminator pigtail 208 is a part of the handle 206 of the imaging unit 202. An optical fiber 210 is used for transmitting the illumination light from the pigtail 208 to an interface 212 in the handle 206. The interface 212 is located within the handle 206 and transfer the light to an annular ring 214 of a plurality of illumination fiber 216.

Figure 17B:
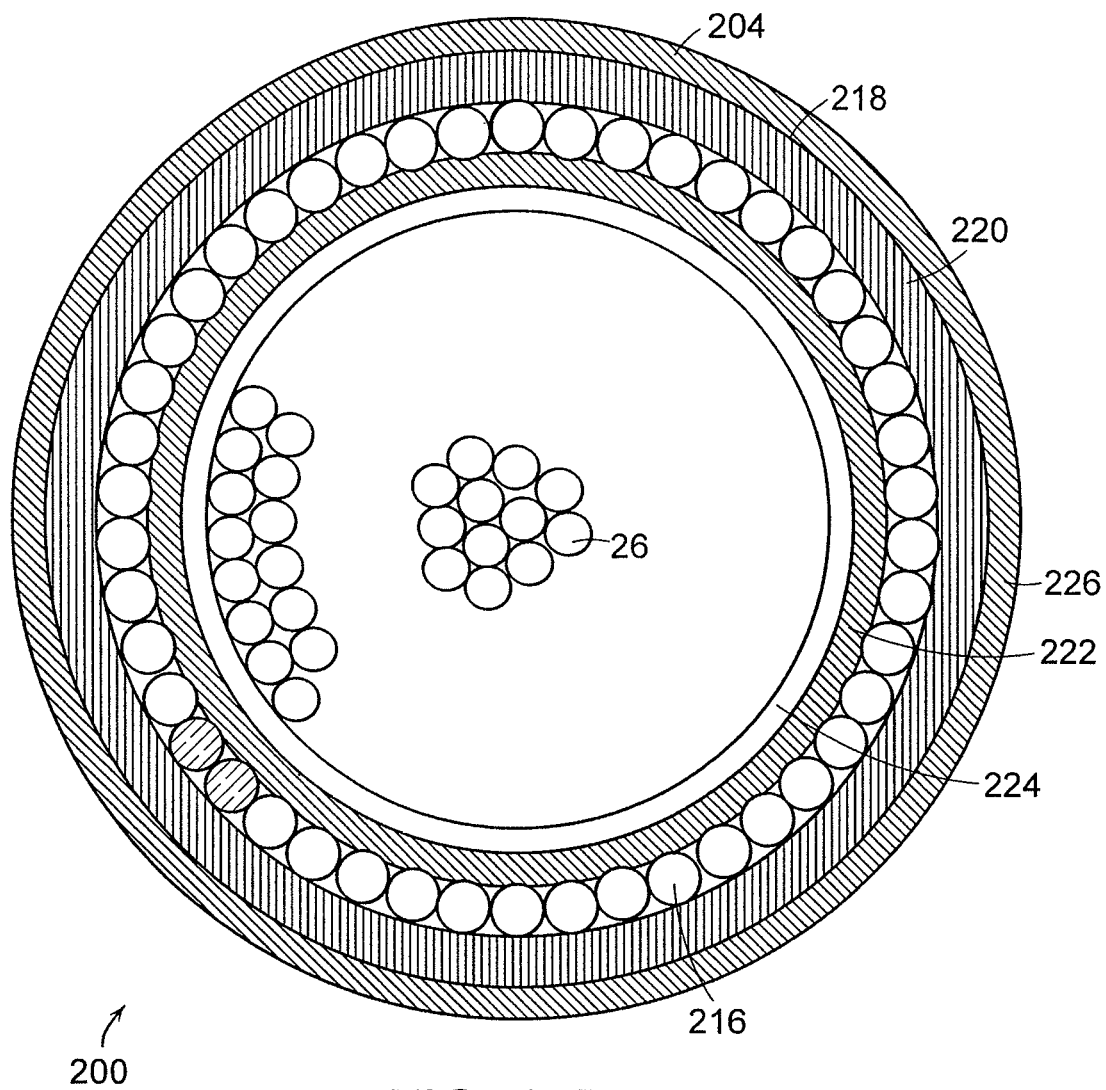
FIG. 17B is a sectional view of the endoscope taken along the line 17B-17B of FIG. 17A.

Referring to FIG. 17B, the probe 218 has an outer tube 220 and an inner tube 222. Interposed between the tubes 220 and 222 is the annular space for receiving the plurality of illumination fibers 216. Located in the inner tube 222, which is similar to the elongated tube 28 in the first embodiment, is the image fiber bundle 26. The fiber bundle 26 is spaced from the inner tube 222. A long tube 224, which extends for a slight distance from the distal end 126 to just beyond the ends of the image fiber bundle 26, is interposed between the fibers 26 and the inner tube 222.

In that the sheath is not required to carry illumination to the distal end of the rod tip 218 in the embodiment shown in FIG. 17B, the sheath 204 has a single outer layer 226. A window curved to avoid retroreflection is secured to the distal end of the single outer layer 226.

Figure 18:
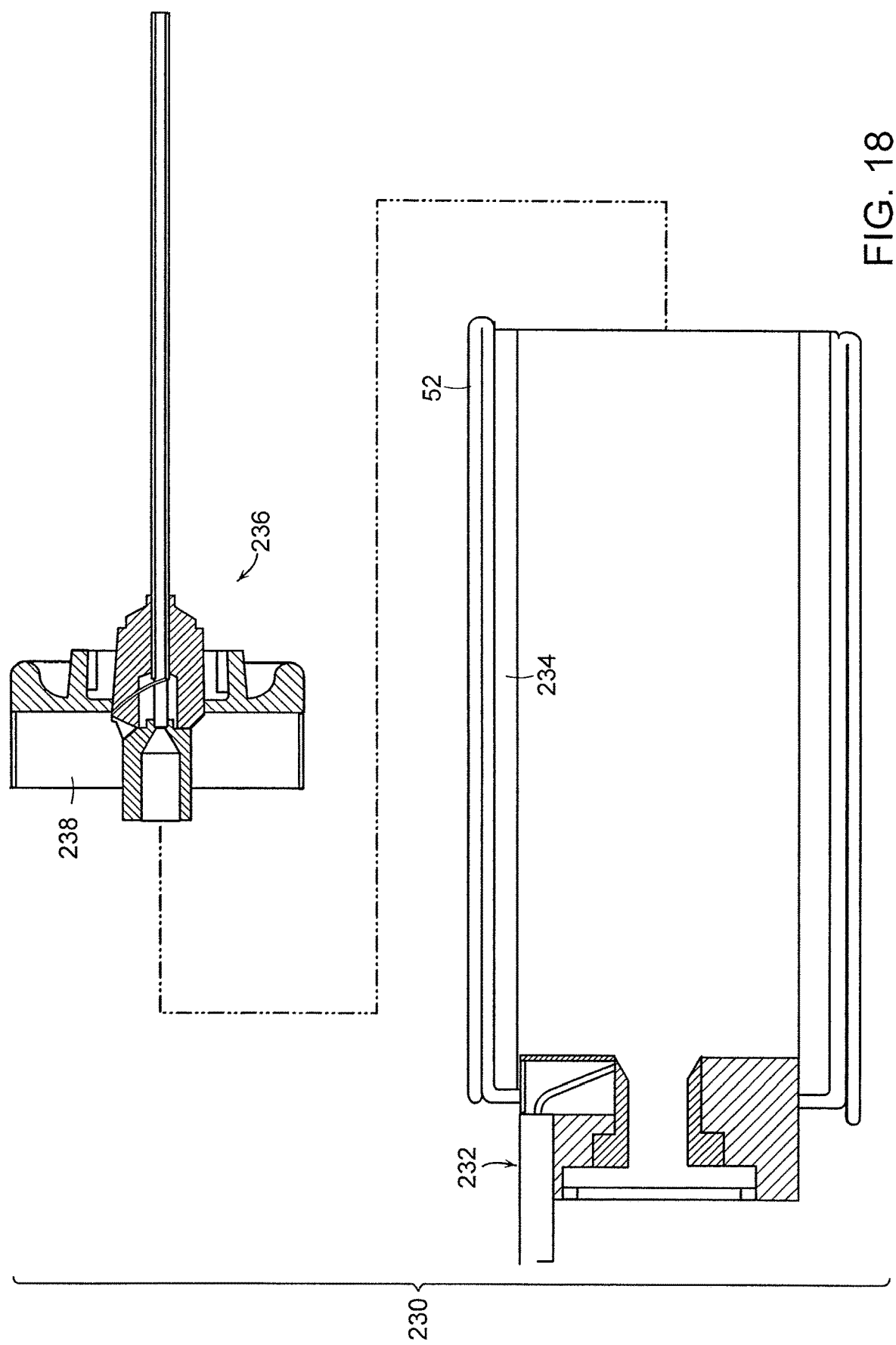
FIG. 18 is a side view of a two-part disposable sheath/illuminator unit.

Referring to FIG. 18, a two piece disposable sheath/illuminator unit 230 is shown. The endoscope has a first unit 232 of the two piece disposable sheath/illumination unit 230, a mounting and cover unit 232, that is mounted to the handle 32 of the imaging unit 22. The mounting and cover unit 232 has a drape 52 that extends over the handle 32 of the imaging unit 22 and the illumination pigtail 88 when used. The drape 52 is retained on a disposable sleeve 234 to hold the drape 52 until positioned over the handle 32. The second unit 236 of the disposable sheath/illumination unit 230, a disposable sheath 236, contains the elongated tube that covers the probe 29. This second unit 236 has a mounting mechanism 238 to secure to the first unit 232. It is therefore possible to remove the disposable sheath, the second unit, 236 and replace it with a new one while keeping the drape 52 that is mounted to the mounting and cover unit 232 over the handle.

Figure 19:
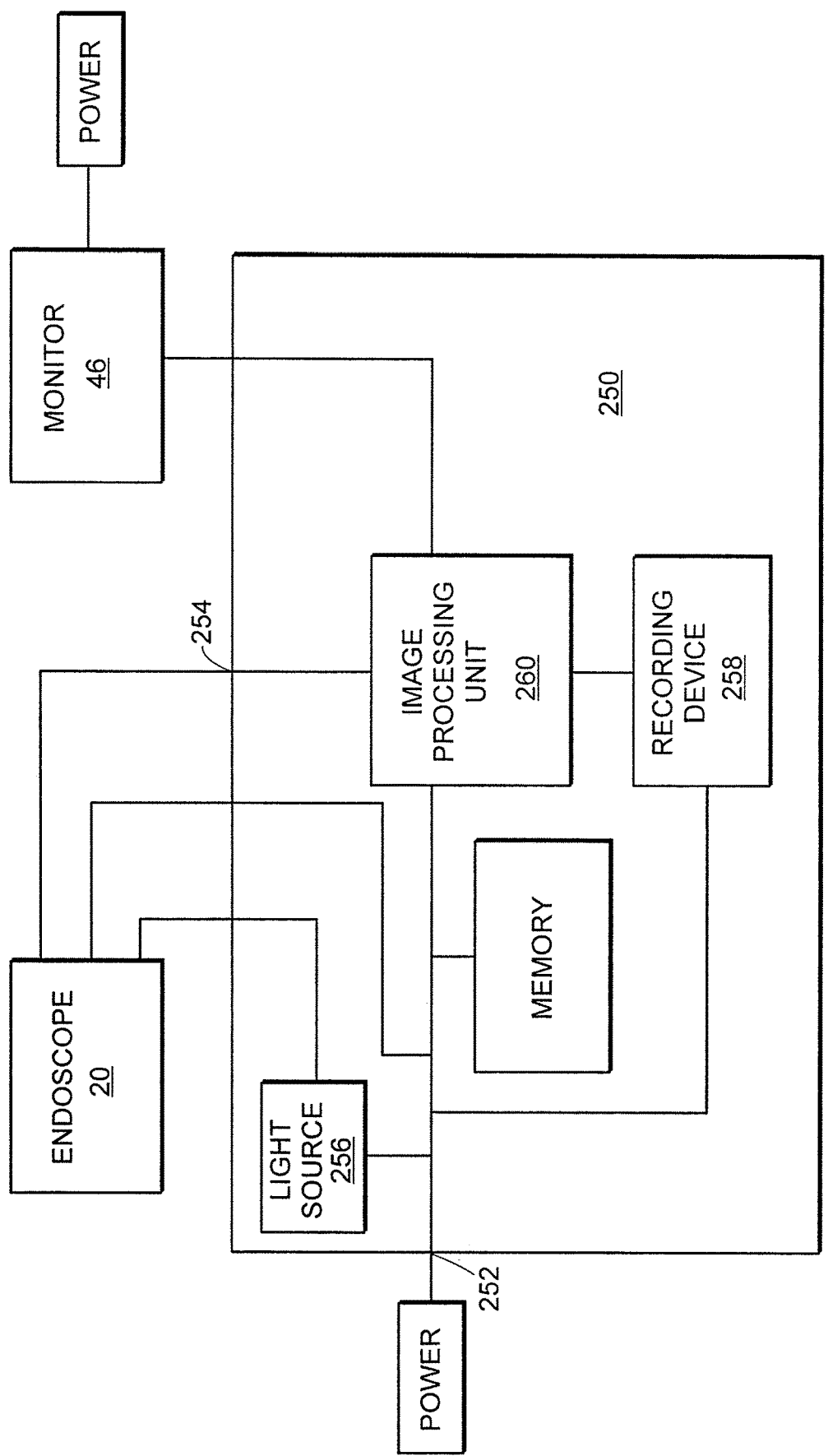
FIG. 19 is a schematic of a control unit for a preferred embodiment of the invention.

FIG. 19 is a schematic of a control unit 250 for the endoscope. This control unit 250 has a power source output 252, an input 254 for the image from the CCD and a light source 256. In addition to a processing unit 260 for processing the image data, the unit has a recording device 258 such as a CD writer to create a storable medium to retain data such as a baseline for the patient.

Figure 20:
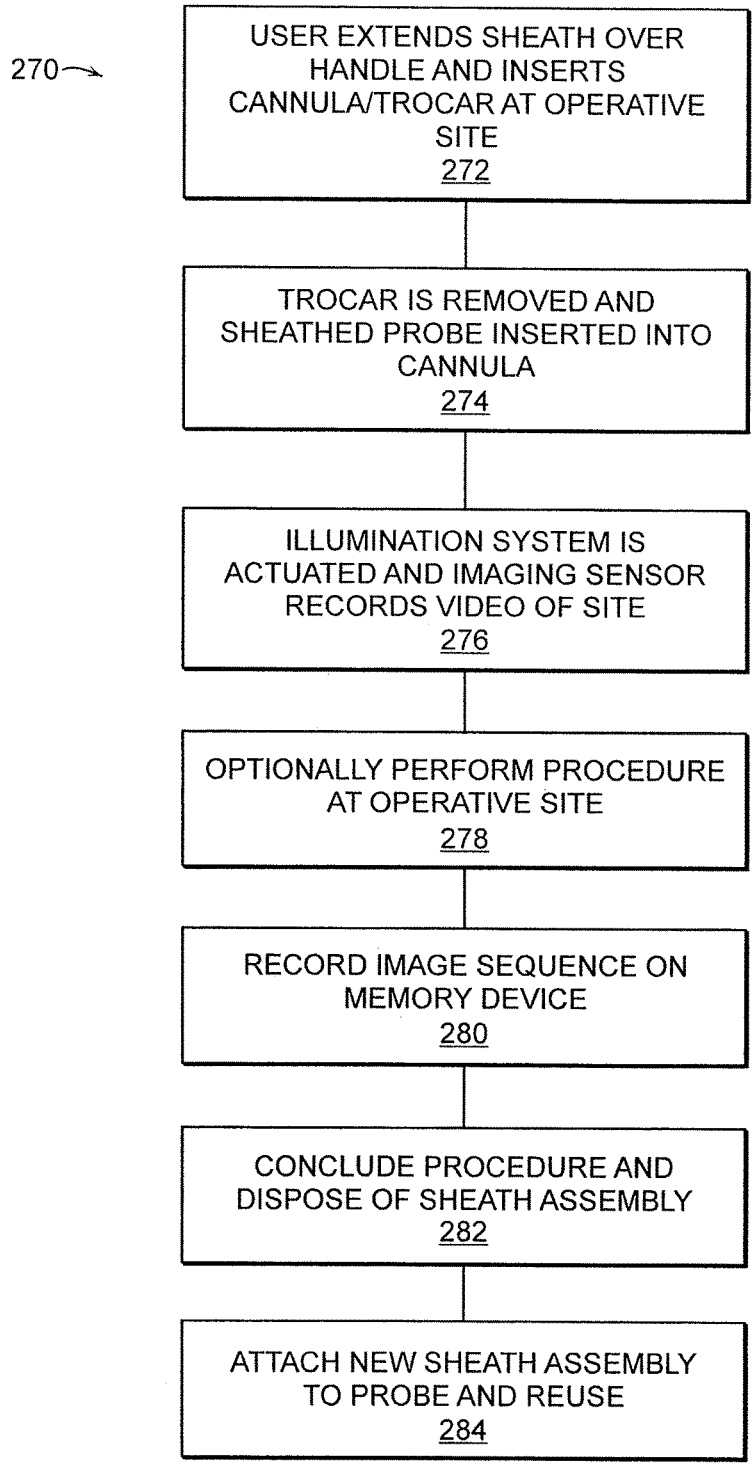
FIG. 20 illustrates a preferred method of using the invention.

The endoscope is used as shown generally in the process sequence 270 of FIG. 20. The patient comes to the user/physician's office. The physician or technician uses a double gloved technique where two sterilized gloves are placed on each of the physician's hands. The physician takes the handle/illuminator unit which is not sterilized in one hand and secure the sterilized sheath/illuminator unit with the other hand. The physician then takes the lighting cord and secures the light cord to the pigtail on the disposable sheath/illuminator unit. The power and image output are likewise connected to the control unit. With the endoscope connected to the control unit, the drape portion of the sheath assembly is extended 272 over the handle and down the cords to such a length to provide a sterile field. With this completed, the physician takes off the first pair of gloves and is ready to begin the procedure.

After medicating the site, the cannula with the trocar is inserted into the body by a standard technique of probing with the physician's hand. Once the cannula is in position, the trocar is removed 274 and the tip of the endoscope is placed into the cannula. The endoscope is secured to the cannula using a screw or other attachment mechanism. The system is actuated 276 and video recording is initiated so that the physician is able to move the cannula in and out and around to position the probe for viewing of the desired site or as a monitor. The physician can perform a procedure 278 at the site using other instruments such as a laser scalpel or cautery tool, or electrosurgical tool and/or the operative channel in the probe or sheath assembly. The entire examination or operative procedure can be recorded 280 on a video disk or other memory device. The procedure is concluded and the sheath assembly can be disposed 282 of and another sterile sheath assembly can be attached 284 to the probe for another procedure.

A preferred embodiment provides multi spectral imaging capability. This embodiment includes the use of a light source and a detector to provide images over the wavelength range of 700 nm-1200 nm. This allows the user to see through blood to observe tissue.

Another embodiment uses the ultraviolet (UV) region of the electromagnetic spectrum (10 nm-380 nm) to be able to treat tissue. Ultraviolet light in the range of 325-250 nm can pull together and cauterize. Lasers or conventional broadband light sources can be used to provide light to the illumination system. The imaging fiber bundle can also be used for illumination with a beam splitter in the handle to couple light from one or more sources individually or simultaneously to the fiber bundle.

Embodiments of the invention can be employed in office-based settings for performing diagnostic imaging of interior surfaces of a body. Office-based as used herein refers to locations other than essentially sterile environments such as, by way of example, hospital operating rooms, hospital procedure rooms, rooms proximate to sterilization means such as autoclaves, and the like. Examples of office locations are, but are not limited to, examination rooms at a physician's office, training rooms adjacent to locker rooms in sporting complexes, ambulances, residences, field hospitals, hospital corridors, examination rooms, emergency rooms, office buildings, stores, and the like.

On site sterilization of the entire miniature endoscope 20 is avoided by making all surfaces that directly contact a patient's skin in the vicinity of the insertion site disposable The disposable portions are retained in sterile packaging until they are utilized for a single procedure. The use of disposable components allows the miniature endoscope 20 to be employed following accepted standards-of-care guidelines such as those used for routine arthroantesis.

In addition, the miniature endoscope 20 operates as a fluidless system, although fluid can be used if desired. A fluidless system refers to the fact that no liquid media, irrigation or distention fluid (e.g., saline solution) has to be injected into a patient's body in the vicinity of the target area, i.e. the area that will be viewed using the invention. In other words, the miniature endoscope can simply be inserted through a patient's skin, and used to view a target area without requiring additional instruments, injection means, consumable substances and without generating excess hazardous waste, other than the disposable portion, such as would be generated if irrigation fluids were injected into and removed from the target area.

The disposable portion 20 may comprise a disposable needle covering employing a transparent window in its distal end. The transparent window prevents fluids from a patient's body from coming into contact with non-disposable portions (e.g., 32) of the system. Nondisposable portions operating in conjunction with the disposable portion 20 may include a thin shaft which slides inside the introducer and contains a fiber optic illumination system for conducting images of the target area to a miniature camera located in a handle 32. The fiber optic illumination system may comprise a protective window and high resolution fiber optics and lens transmission means for conveying images to the camera. The disposable portion may also include a slide port for introduction of surgical instruments or for evacuation of fluids by suction or for introduction of medications to the target area.

Figure 21:
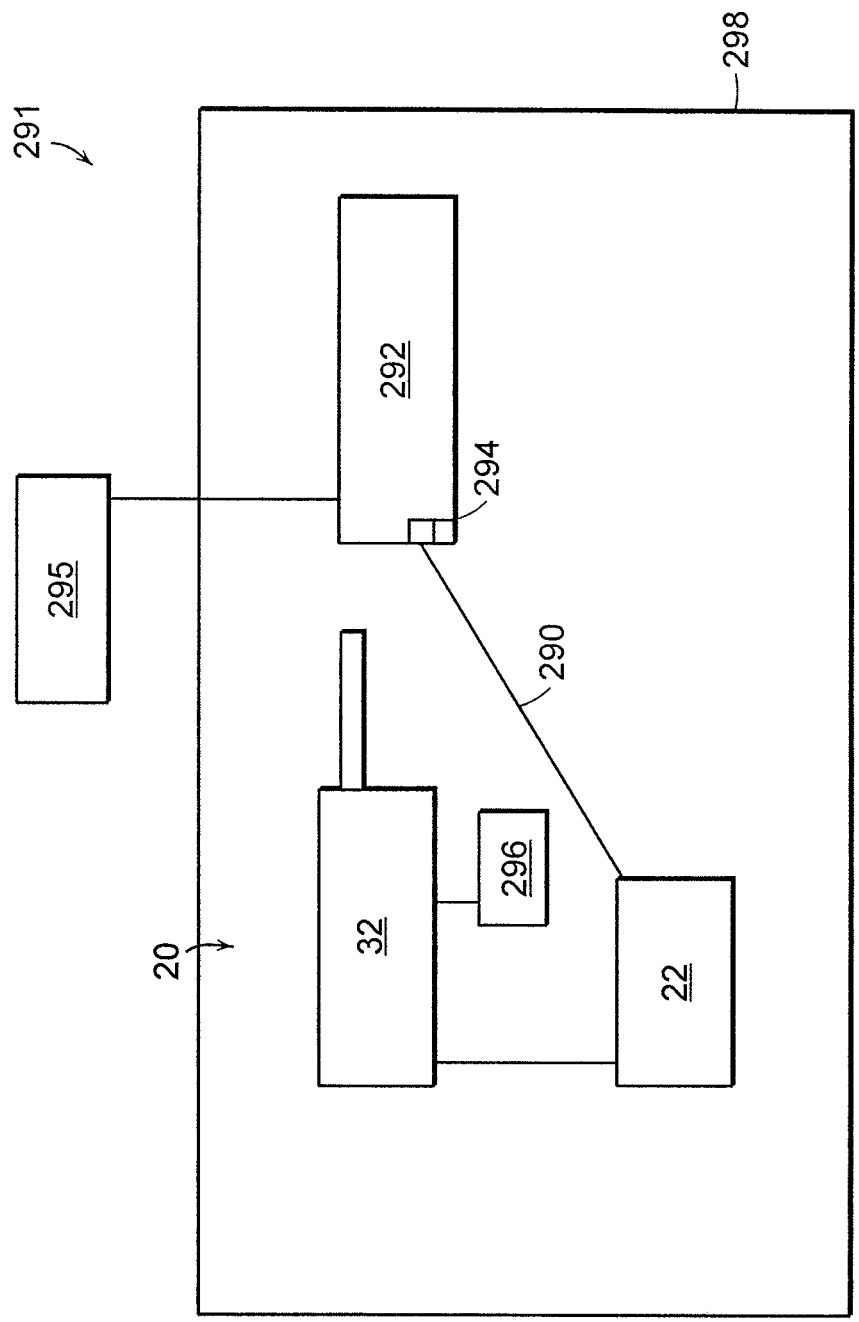
FIG. 21 illustrates a preferred embodiment of a portable endoscopic system in accordance with the invention.

In an embodiment of the invention, a highly portable miniature endoscopic imaging system is provided. The system shown in FIG. 21 is man-portable, in that it can be transported or carried by a person. FIG. 21 illustrates exemplary embodiments of a portable endoscopic system 291 comprising, among other things, miniature endoscope 20, handle 32, imaging unit 22, cable 290 and laptop 292. In FIG. 21, the endoscopic unit and imaging unit 22 are connected directly to laptop 292 by way of cable 290. For example, imaging unit 22 may output a video signal that is sent to a video in jack on laptop 292. Laptop 292 is then used to enter patient information, session details, and is used to display real-time image data as the procedure is carried out.

An embodiment of the portable endoscopic system employs a personal computer memory card international association (PCMCIA) card for facilitating coupling of image data to laptop 292. PCMCIA card may be an industry standard card as known in the art, or it may be specially adapted for use with the miniature endoscope. A specially adapted PCMCIA card may include hardware for receiving and processing video signals received from the imaging unit. The output of PCMCIA card 294 may be an industry standard data format for conveying processed image data to a display associated with the laptop.

A portable endoscopic system 291 that includes imaging unit or an interface box 32 and an interface box cable 290 for conveying data to laptop 292. Interface box may include more sophisticated imaging, image processing, and data communication hardware and/or software than can be employed in PCMCIA card 294 or directly inside laptop 292. The interface box 296 may be configured to perform real-time image enhancement on data received through the distal end of miniature endoscope 20. Image enhancement may be used to produce images suitable for performing diagnostics while making use of less costly components in miniature endoscope 20. By way of example, a GRIN lens may be employed in miniature endoscope 20 to provide image data to the interface box. The interface box may employ image processing algorithms for enhancing the image quality produced by the edges of GRIN lenses. Interface box may then convey image data to laptop 292 in an industry standard format by way of cable. The system can also include mounting on a cart 298 for transport, as display 295 and a light source system 296. The system can include a standard lamp for visible light imaging as well as infrared or ultraviolet light sources for imaging or treatment.

A generalized architecture can be used including a central processing unit (CPU), which is typically comprised of a microprocessor associated with random access memory (RAM) and read-only memory (ROM). Often, the CPU is also provided with cache memory and programmable FlashROM. The interface between the microprocessor and the various types of CPU memory is often referred to as a local bus, but also may be a more generic or industry standard bus. CPU processes and interprets machine-readable, or function-executable, instructions associated with an operating system, user-developed applications, diagnostic tools, patient data hospital servers, health provider computers, and computers associated with remote experts. A graphical user interface (GUI) can be used for patient data entry and display as well as image viewing.

Many computing platforms are also provided with one or more storage drives, such as a hard-disk drives (HDD), floppy disk drives, compact disc drives (CD, CD-R, CD-RW, DVD, DVD-R, etc.), and proprietary disk and tape drives (e.g., Iomega Zip™ and Jaz™, etc.). Additionally, some storage drives may be accessible over a computer network such as network-based storage system. The RAM is capable of storing machine-readable instructions and information necessary to operate software applications for processing and displaying image data received from miniature endoscope.

Many computing platforms are provided with one or more communication interfaces, according to the function intended of the computing platform. For example, a personal computer, laptop, or belt-wearable computer is often provided with a high speed serial port (RS-232, RS-422, etc.), an enhanced parallel port (EPP), and one or more universal serial bus (USB) ports. The computing platform may also be provided with a local area network (LAN) interface, such as an Ethernet card, and other high-speed interfaces such as the High Performance Serial Bus IEEE-1394.

Computing platforms such as wireless telephones and wireless networked PDA's may also be provided with a radio frequency (RF) interface with antenna, as well. In some cases, the computing platform may also be provided with an infrared data arrangement (IrDA) interface.

Computing platforms are often equipped with one or more internal expansion slots, such as Industry Standard Architecture (ISA), Enhanced Industry Standard Architecture (EISA), Peripheral Component Interconnect (PCI), Personal Computer Memory Card International Association (PCMCIA), or proprietary interface slots for the addition of other hardware, such as sound cards, memory boards, and graphics accelerators.

Additionally, many units, such as laptop computers and PDA's, are provided with one or more external expansion slots allowing the user the ability to easily install and remove hardware expansion devices, such as PCMCIA cards, Smart-Media cards, and various proprietary modules such as removable hard drives, CD drives, and floppy drives.

Often, the storage drives, communication interfaces, internal expansion slots and external expansion slots are interconnected with the CPU via a standard or industry open bus architecture, such as ISA, EISA, or PCI.

A computing platform is usually provided with one or more user input devices, such as a keyboard or a keypad, and mouse or pointer device, and/or a touch-screen display. In the case of a personal computer, a full size keyboard is often provided along with a mouse or pointer device, such as a track ball or TrackPoint™. In the case of a web-enabled wireless telephone, a simple keypad may be provided with one or more function-specific keys. In the case of a PDA, a touch-screen is usually provided, often with handwriting recognition capabilities, and in the case of a laptop, a small keyboard and touch-sensitive display may be provided.

Additionally, a microphone, such as the microphone of a web-enabled wireless telephone or the microphone of a personal computer, is supplied with the computing platform. This microphone may be used for entering user choices, such as voice navigation of web sites, user menus associated with operating miniature endoscope 20, conveying data to remote locations, or auto-dialing telephone numbers. Voice recognition capabilities normally in the form of software may be employed for facilitating speech based interaction with the computer.

Many computing platforms are also equipped with a camera device, such as a still digital camera or full motion video digital camera which can be used for facilitating collaboration between the person performing the endoscopic procedure and a remote expert that may be guiding the procedure and interpreting results in essentially real-time by way of a networked display device.

One or more user output devices, such as a display, are also provided with most computing platforms. The display may take many forms, including a Cathode Ray Tube (CRT), a Thin Film Transistor (TFT) array, a simple set of light emitting diodes (LED), liquid crystal display (LCD) indicators, a heads-up (i.e. hands free) display, or a projection display.

One or more speakers and/or annunciators are often associated with computing platforms, too. The speakers may be used to reproduce audio instructions. Annuciators may take the form of simple beep emitters or buzzers, commonly found on certain devices such as PDAs and PIMs. Annunciators may be used to alert the operator of system that an error has occurred. These user input and output devices may be directly interconnected to the CPU via a proprietary bus structure and/or interfaces, or they may be interconnected through one or more industry open buses such as ISA, EISA, PCI, etc. The computing platform is also provided with one or more software and firmware programs to implement the desired functionality of the computing platforms.

A generalized organization of software and firmware on this range of computing platforms. One or more operating system (OS) native application programs may be provided on the computing platform, such as word processors, spreadsheets, contact management utilities, address book, calendar, email client, patient tracking, user menus for operating system, etc. Additionally, one or more portable or device-independent programs may be provided, which must be interpreted by an OS-native platform-specific interpreter, such as Java™ scripts and programs.

Often, computing platforms are also provided with a form of web browser or micro-browser, which may also include one or more extensions to the browser such as browser plug-ins and configured to facilitate transmission and reception of image data over network.

The computing device is often provided with an operating system, such as Microsoft Windows™, UNIX®, IBM OS/2™, or AIX®, LINUX, MAC OS™, Sun Solaris™, or other platform specific operating systems. Smaller devices such as PDA's and wireless telephones may be equipped with other forms of operating systems such as real-time operating systems (RTOS) or Palm Computing's PalmOS™.

A set of basic input and output functions (BIOS) and hardware device drivers 356 are often provided to allow the operating system and programs to interface to and control the specific hardware functions provided with the computing platform. Additionally, one or more embedded firmware programs 358 are commonly provided with many computing platforms, which are executed by onboard or "embedded" microprocessors as part of the peripheral device, such as a microcontroller or a hard drive, a communication processor, network interface card, or sound or graphics card.

Various hardware components, software and firmware programs of a wide variety of computing platforms, including but not limited to personal computers, laptops, workstations, servers, web-enabled telephones, and other like appliances can be used. It will be readily recognized by those skilled in the art that the following methods and processes may be alternatively realized as hardware functions, in part or in whole, without departing from the spirit and scope of the invention.

An exemplary system uses portable system operating in conjunction with a network. A doctor's office containing portable system, a network, a health insurance provider having data storage associated therewith, a hospital server having data storage, a remote expert computer and a network-based storage system.

The doctor's office employs a portable system for performing diagnostic evaluations of one or more patients. Image data obtained from a session may be stored on the laptop memory and conveyed to one or more remote locations by way of a network. The network may be any type of network running any kind of network protocol. By way of example, the network may be an intranet such as a local area network (LAN) operating within a corporate location or university campus, a metropolitan area network (MAN) operating within a geographic region such as a city and its surrounding suburbs, or a wide area network (WAN) such as the world wide web. In addition, the network may run any type of networking protocol such as, for example, transmission control protocol and Internet protocol (TCP/IP), asynchronous transfer mode (ATM), synchronous optical network (Sonet), frame relay, integrated services digital network (ISDN), open shortest path first (OSPF), etc. The network may employ a plurality of links for coupling network elements and locations. Links may be comprised of hardwired links and/or wireless links. Examples of hardwired links are, but are not limited to, coaxial cable, twisted pair cable, optical fibers, etc.; and examples of wireless links are, but are not limited to, radio frequency (RF) such as IEEE 802.11 based links, or free space optical links. The network may also comprise gateways and/or firewalls for providing access to the network and for providing protection against undesirable network traffic such as denial-of-service attacks as well as network traffic containing malicious code such as computer worms and viruses.

Data conveyed from the portable system to the network may be directed to a health insurance provider. The health insurance provider may archive received data on data storage by way of link for future use. The health insurance provider may employ its own experts, alone or in combination with automated analysis systems, to review data obtained during an endoscopic procedure using the invention. A portable system may also convey data to a hospital server. The hospital server may further include data storage coupled thereto by link. Hospital server may serve as a pooling resource for maintaining data associated with patients having an affiliation therewith. By way of example, if a patient required surgery based on a diagnosis obtained using portable system, the image data could be reviewed by a surgeon prior to, or during, surgery to ensure that proper and complete treatment is rendered in an efficient manner.

Data obtained using portable system may further be sent to a remote expert computer by way of network. A remote expert, using remote expert computer, may review image data post mortem or in quasi-real-time. The remote expert may provide a second opinion prior to scheduling more invasive procedures or the remote expert may provide the primary diagnosis in situations where a skilled operator is performing the procedure with miniature endoscope 20. For example, disaster relief personnel may be on scene at a remote location and performing a diagnostic procedure on a disaster victim. A remote expert may be viewing image data received over a free space satellite network in real-time to direct the on-scene personnel with respect to the diagnostic procedure. The remote expert may then direct an on-scene person to mark an insertion location on a victim/patient, to introduce the needle covering, to maneuver the endoscope 20, and then may use real-time data to recommend accurate treatment for the victim without having to be on site. Data from the portable system may further be conveyed to a network-based storage system. The network-based storage system may serve as secure and redundant storage for image data resident on laptop. In addition, the network-based storage system may serve to keep image data in a location that is more readily accessed for replay than if the data were kept solely on laptop. The system and other remote entities may be communicated with using portable system without departing from the spirit of the invention.

A preferred method for using the miniature endoscope 20 in conjunction with portable system involves performing diagnostic procedures. The system can be transported by cart into an examination room or other site where the procedure will be performed. Then a camera is coupled to the viewing system. Next, an insertion site is prepared on a patient's body. Preparation of the insertion site may include, among other things, marking the site using a medically approved writing instrument, and cleansing the area with an antiseptic solution, etc. A disposable needle covering may be coupled to the imaging and viewing system. As previously discussed herein, only disposable portions of miniature endoscope 20 contact the patient so no special sterilization processes need be applied on site. The needle covering of miniature endoscope 20 is then inserted into a target area of a patient. After the needle point is in the vicinity of the target, the imaging and viewing system may be activated. Image data is viewed and recorded using laptop during the diagnostic procedure. When the diagnosis is complete, the needle is withdrawn from the target area. After needle withdrawal, the insertion location may be dressed using sutures, liquid adhesives approved for topical wound dressing, butterfly closures, or conventional small wound dressings such as gauze or bandages.

Recorded image data can be reviewed by the diagnostician and shown to the patient in the procedure room. After review, recorded data can be archived locally on a laptop, on removable storage media, or by way of network-based storage system. In addition, image data long with alphanumeric and/or voice annotations may be sent to one or more remote locations using network. Then the portable system may be returned to its storage location, and the patient immediately discharged after the procedure, since no complex anesthesia was required.

While exemplary embodiments of the invention have been described and illustrated hereinabove, the invention is not limited thereto. Many alternative embodiments and implementations are possible in light of the disclosure without departing from the spirit of the invention. For example, the portable system may be deployed in a distributed architecture where the user is located at a first geographic location, with a patient and the miniature endoscope comprising elements 20, 21 and 22 while the laptop display is located a distance away and is coupled to the miniature endoscope by way of a wireless network. In another alternative embodiment, the invention may be deployed in a ruggedized configuration for use in battlefield triage and/or for responding to disasters in remote and rugged locations. In still other embodiments, the portable endoscopic system may be integrated into mechanized conveyances such as trains, ambulances, air planes, ships, vehicles, etc. In yet other embodiments, images generated using the portable endoscopic system may be replayed and used for training purposes. In still further embodiments, the portable endoscopic system may comprise a belt-wearable computer having a short range high bandwidth link to handle for receiving image data. In this embodiment, handle may comprise a self-contained power source such as a rechargeable battery. This embodiment may further utilize a heads-up display worn on a user's head. Such a configuration provides the user with maximum mobility and minimum weight. The belt-wearable embodiment may further communicate with network by way of a wireless link.

In yet another alternative embodiment, the laptop can be replaced with a customized processing device that can take on essentially any form factor and user interface configuration. For example, it may be desirable to have a dedicated processing module having only an on/off switch. When switched on, the customized processing device may gather image data and store it for later review or it may automatically transmit data to a remote location using a wireless RF or free space optical link.

Figure 22A:
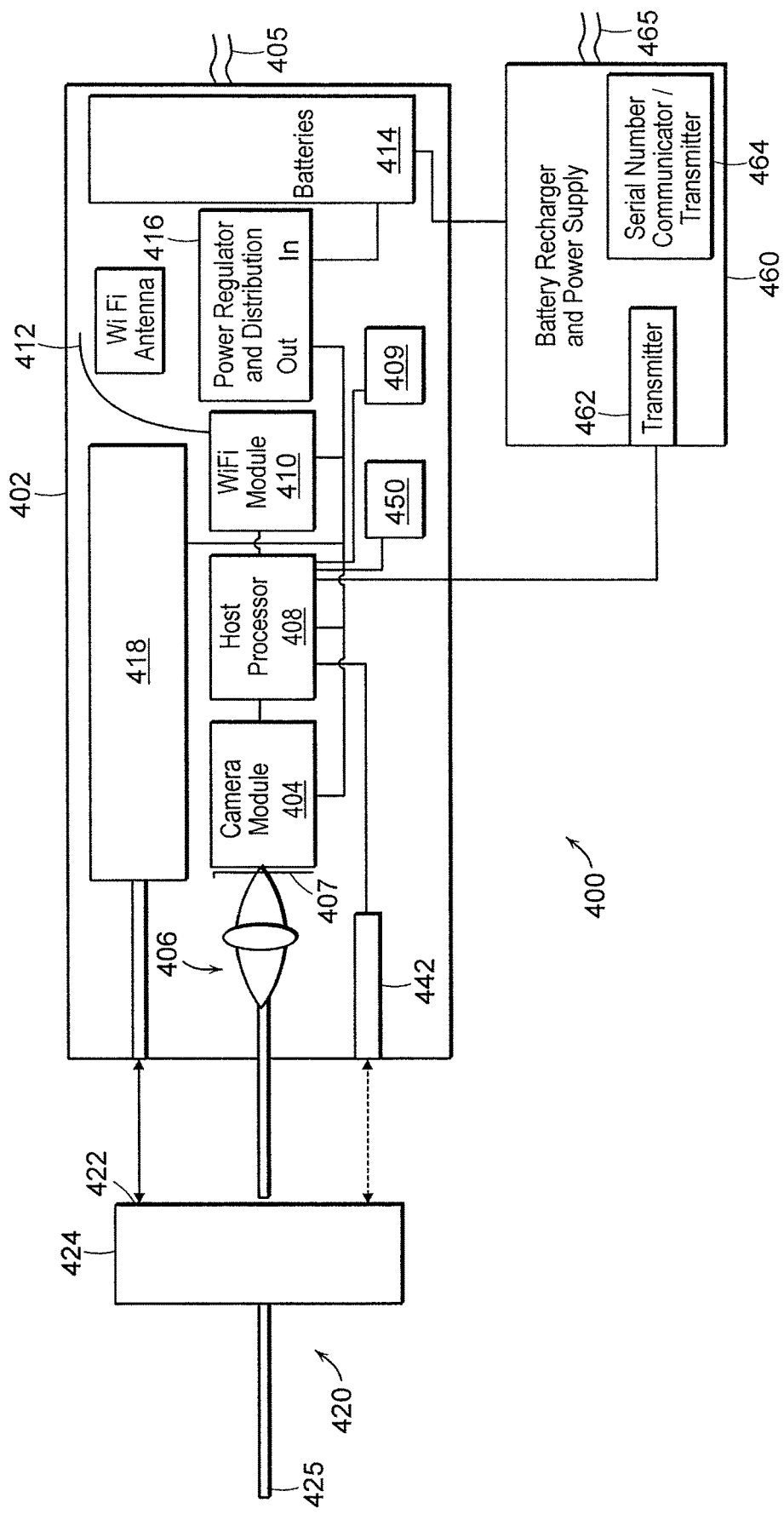
FIG. 22A illustrates a preferred embodiment of an endoscopic in accordance with the invention.

FIG. 22A illustrates another preferred embodiment of a portable endoscope 400 in accordance with the invention including a handle 402 having a camera module 404, an optical coupler 406, a processor 408, a wireless communications module 410, a wireless antenna 412, a battery 414 and a power regulator 416. Also included in the portable system is a light source 418 within handle 402. The light source 418 preferably comprises an LED assembly such as an EOS™ LED fiber optic illuminator available from Edmund Optics, Barrington, N.J. The light source can also comprise one or more laser diodes or a combination of laser diodes and LEDs, a laser or laser diode in the ultraviolet portion of the spectrum can be used to induce fluorescence in tissue for diagnostic purposes or for cautery. The handle can have a control panel 409 with buttons that the user employs to electrically operate the handle.

The camera 404 can be a CCD or CMOS imaging sensor such as the TC7040 two megapixel CMOS imaging sensor device available from TransChip Israel Research Center, Ltd. This device includes a 1600×1200 pixel color sensor array that is packaged with a clock, controller, image processor and local SRAM memory in a single chip package. The camera preferably has sensitivity in the infrared portion of the spectrum (750-1000 nm) as well as the visible. For certain applications it is preferable to use an infrared imaging sensor that can detect light in the range of 1500 nm to 1900 nm, for example, as this improves imaging of tissue through blood. An infrared light source as well as spectral or cutoff filters 407 for the detector may be needed for certain spectral imaging applications.

The disposable 420 as described previously herein has a port 422 for coupling light from the light source into the fiber optic illumination bundle within the coupler 424 of the disposable. The distal end of the sheath can have a cutting element 425 that can be recessed during insertion and imaging and mechanically actuated by wire or other means to cut a tissue sample from a region of interest within the body.

Figure 23:
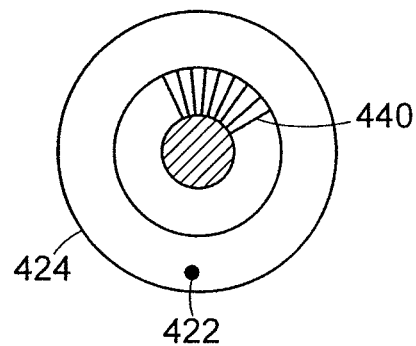
FIG. 23 is an end view of a sheath.

The handle 402 can also include a bar code reader 442 or other device that uniquely identifies the disposable component being attached thereto. The bar code 440 can be imprinted on the proximal end of the disposable coupler 424 shown in FIG. 23. This bar code can have a radial or rectangular array. A radial array can be scanned past the reader 442 while the coupler 424 rotates into the locked position with the handle 402. Alternatively some other electronic identifying and recording device such as a radio frequency identification (RFID) system can be used or a chip with a serial number can be in the disposable. This can be used for safety and record/inventory purposes. In another alternative embodiment, one or more disposable components can be inserted into a bag, container or package having a machine readable element or code as described above. This machine readable element uniquely identifies the disposable or disposable kit that is contained within the package. This kit can include the disposable sheath, the cannula and the trocar as described in connection with the various embodiments of the present invention. As described in the process sequence 480 of FIG. 28, the machine readable package or container 482 is scanned by a scanner such as a bar code sensor that is connected to the system computer which then records 484 the specific disposable package or kit and enables 486 operation of the system. After the disposable is attached and used 488 to obtain images, the disposable is detached and disposed of for safety. The system computer is programmed with a software program that requires a new package code to be scanned before enabling the system to operate further.

The wireless module provides for delivery of video from the handle to a receiver in communication with a desktop or laptop computer. A cable 405 can also optionally be connected to the handle 402 to provide a connection to the computer and associated display. A display 450 can also be integrated directly into the handle 402 for viewing by the user. The video or still images taken with the camera can also be recorded onto removable media such as a compact flash card, CD, DVD, mini DVD or SD card. Compact media can be inserted into a slot in the handle 402.

For certain applications it can be desirable to use the imaging waveguide to deliver light onto the tissue as well. A beam splitter within the handle can be used for this purpose as described previously.

Figure 22B:
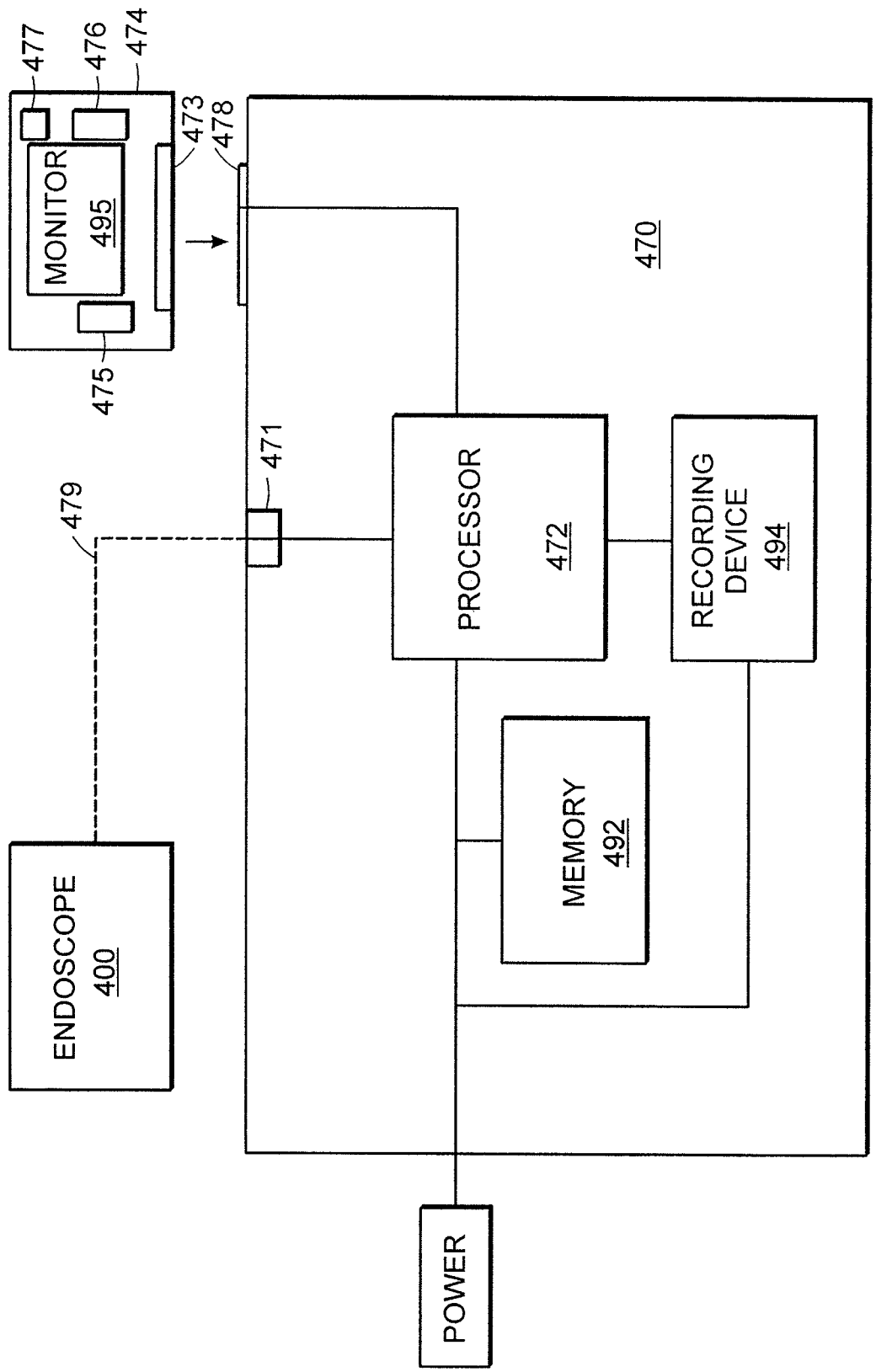
FIG. 22B illustrating a control system for another preferred embodiment of the invention.

The handle 402 can also be configured to dock with a base unit 460 that can transmit and receive images and data from the processor 408 with a transceiver 462. The base 460 can also be used as a recharger for the battery 414 and can include a communications circuit for a network or internet connection, a facsimile device or standard telephone data connection. The endoscope 400 can interface with a system 470 such as that shown in FIG. 22B. The connection 479 with the endoscope can be wired or wireless. A wireless transmitter/receiver 471 is connected to processor 472 that is programmed to provide control signals to the endoscope 400. The processor receives image data that can be stored in memory 492 or printed or electronically copies with device 494. A display device 474 such as those provided by Motion Computing, Inc., of Austin, Tex., with display 495 can be integrated with unit 470 or can be in wireless communication with unit 470 or other network using transmitter receiver 475. Device 474 can also dock with system 470 using connectors 473, 478. Device 474 can be powered by battery 476 and can also include a sensor 477 that can be used to identify a patient, a disposable sheath or other machine readable data. Sensor 477 can be a bar code reader or other identification sensor as described previously herein. The system shown in FIGS. 22A and 22B can be implemented in a portable design having a weight of 10 pounds or less.

The disposable can also include a lens at the distal end, or a prism or mirror for side-viewing applications. The disposable can have a length of between 20 mm and 2500 mm depending on the application. For small joints or bones such as the hand or foot smaller lengths in the range of 20 mm to 800 mm are used. For the knee and shoulder lengths in the range of 800 mm to 1500 mm can be used for applications such as the hip, longer lengths from 1500 mm up to 2500 mm may be used. For imaging applications such as the breast or brain, imaging in the visible portion of the spectrum can be supplemented by imaging in the near infrared or infrared portions of the spectrum. This can be used to supplement mammographic screening. Other imaging and diagnostic applications include ovarian cancer diagnostic imaging and spectral diagnosis, endometriosis, pre-natal diagnostic imaging, prolapse or fibroid imaging and treatment, and urinary tract diagnostics. The system can also be used for upper respiratory applications including the ear, nose and throat. These embodiments can employ a flexible probe in which polymeric tubes are used to house the distal imaging channel assembly and form the tubular wall of the disposable sheath. A biopsy can also be used to collect a tissue sample, if needed. Dyes or tissue autofluorescence can also be used with a narrowband light source such as a laser diode emitting at a wavelength in a range of 300 nm to 500 nm, for example. Gallium nitride diode lasers can be used for this purpose.

Figure 24A:
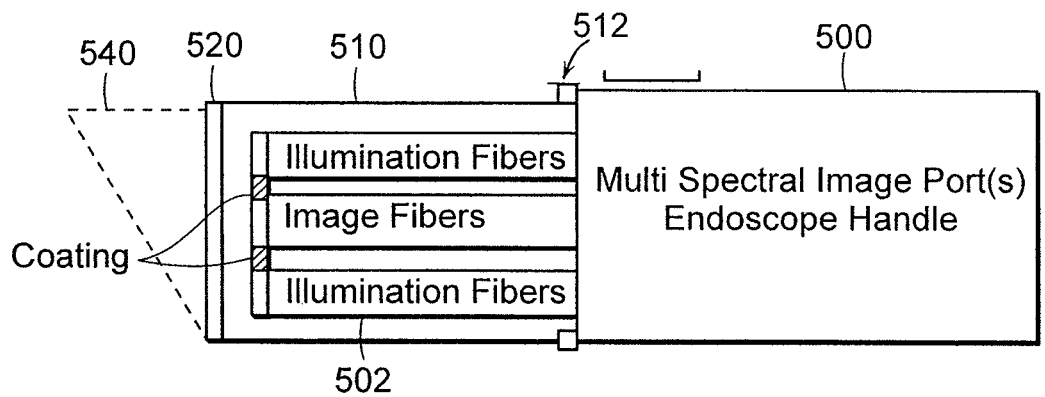
FIG. 24A is a schematic view of a preferred endoscopic device.
Figure 24B:
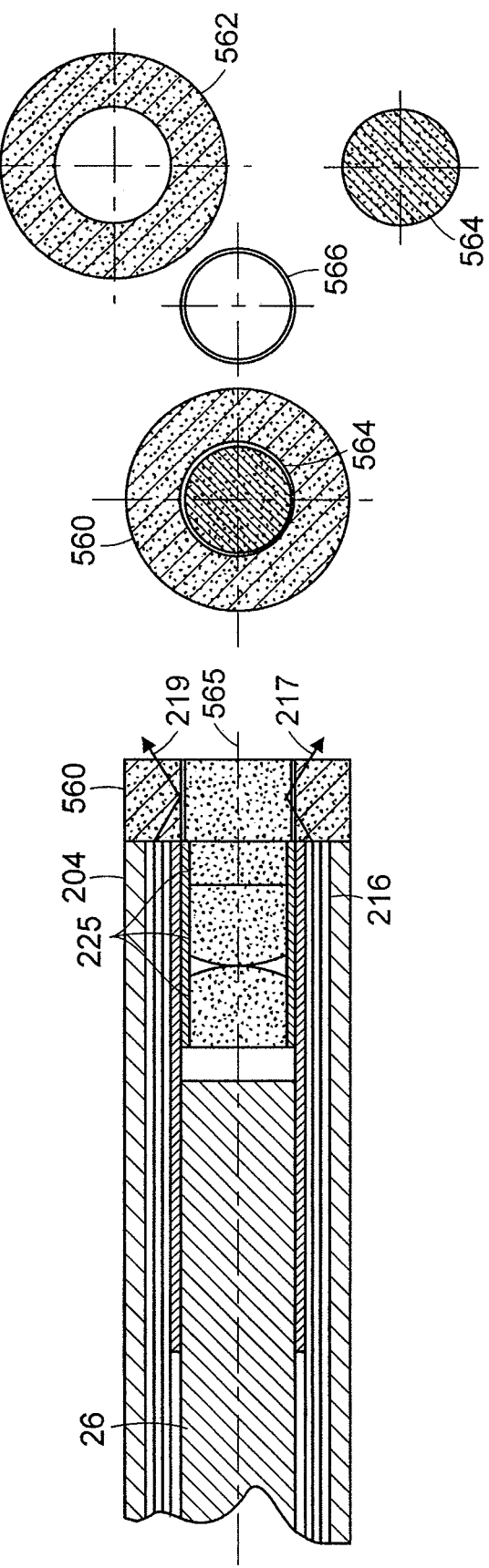
FIG. 24B is a cross-sectional view of the insertion portion of the probe.

FIG. 24A shows a preferred embodiment in which the illumination fibers 502 are rigidly attached to the handle 500. The disposable 510 is connected with connector 512 to the handle and can include a lens 520 or a mirror or prism 540 for angled or side viewing. A cross-sectional side view of such an embodiment is illustrated in FIG. 24B which is also seen in the sectional view of FIG. 17B. This embodiment employs a distal window 560 on the end of the disposable sheath 204 that has a fluid tight seal to the sheath. In this embodiment the window has an outer transparent element or illumination window 562 that transmits the illuminating light from the fibers 216 in a distal direction as shown by light rays 217, 219. The window 560 can have a separate inner element or light collection window 564 which receives light returning from the illuminated region of interest. The outer and inner window elements are optically decoupled by a light barrier 566 that can be a stainless steel spacer that is attached to both the outer and inner elements 562, 564 using an adhesive, for example. The imaging fibers 26 receive light collected through element 564 and focused by lens system 225 onto the imaging fibers generally along longitudinal axis 565.

Figure 24C:
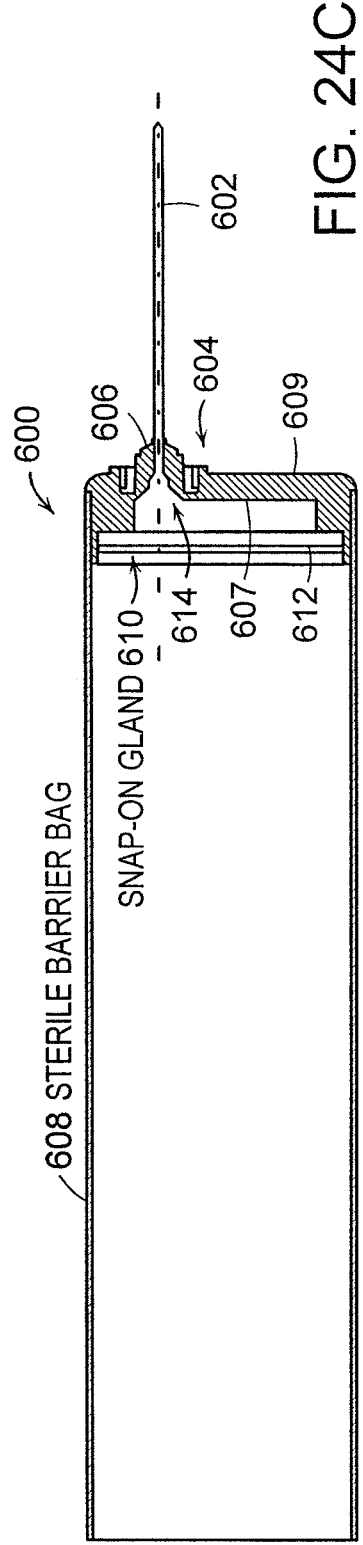
FIGS. 24C-24I illustrate preferred embodiments of the endoscope system in accordance with the invention.
Figure 24D:
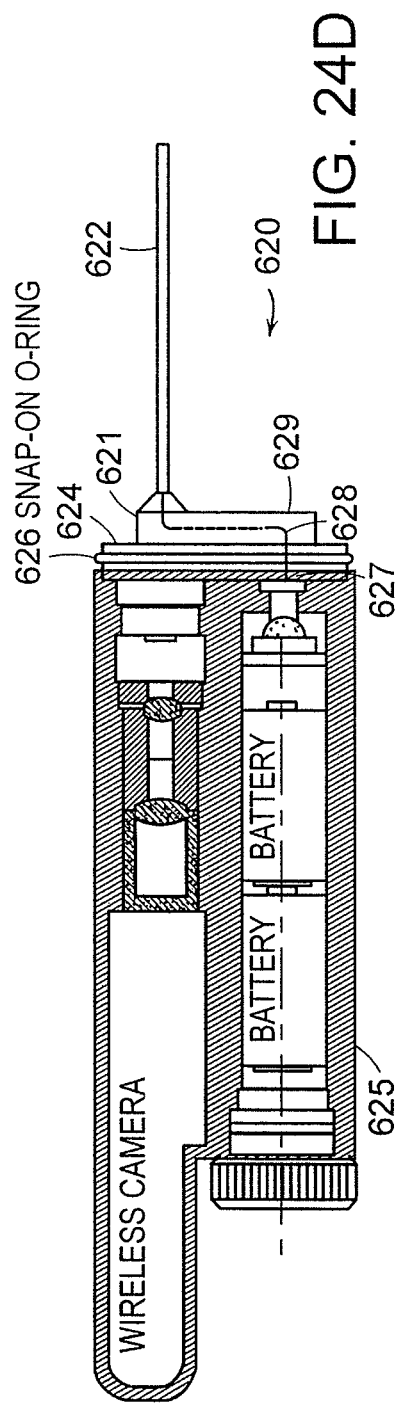
Figure 24E:
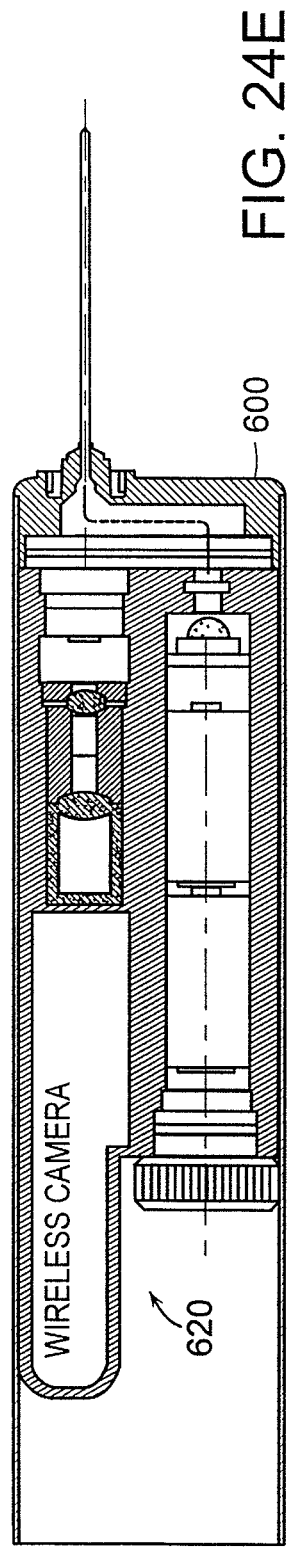

Shown in FIGS. 24C-24E are cross-sectional view of a preferred embodiment of a small diameter endoscope including a disposable sheath 600 and an imaging and illumination assembly 620. The disposable sheath 600 shown in FIG. 24C, does not incorporate the illumination channel, but rather has a thin walled tube 602 sealed at the distal end with a window assembly described herein. The tube 602 is attached at its proximal end to a hub 604 that includes a cannula connector 606 mounted on a sheath housing element 605. A sheath connector 610 is attached to the proximal side of housing element 605 and the sterile barrier 608 is attached to the outer wall of housing element 605.

The sheath connector 610 includes an o-ring groove 612 such that upon insertion of the imaging and illumination assembly 620 into the sheath 600, an o-ring 626 on a mating connector 624 will "snap" into the connector 610. During insertion, the distal end of tube 622 is inserted through the central opening in the connector 610 and into the proximal opening 614 of tube 602. The distal surface 629 of the distal hub 621 on handle 625 can butt against the proximal surface 607 of element 605. In this embodiment, as shown in FIG. 24D, the fiber optic illumination bundle 628 extends through the distal hub 621 to the optical coupler 627 that is optically coupled to the light source without the need for a window to seal the light source as in the embodiment of FIG. 16E. The embodiment of FIG. 24D can have handle components identical to those in FIG. 16E except as described above. The assembled unit shown in FIG. 24E is ready for use.

Figure 24F:
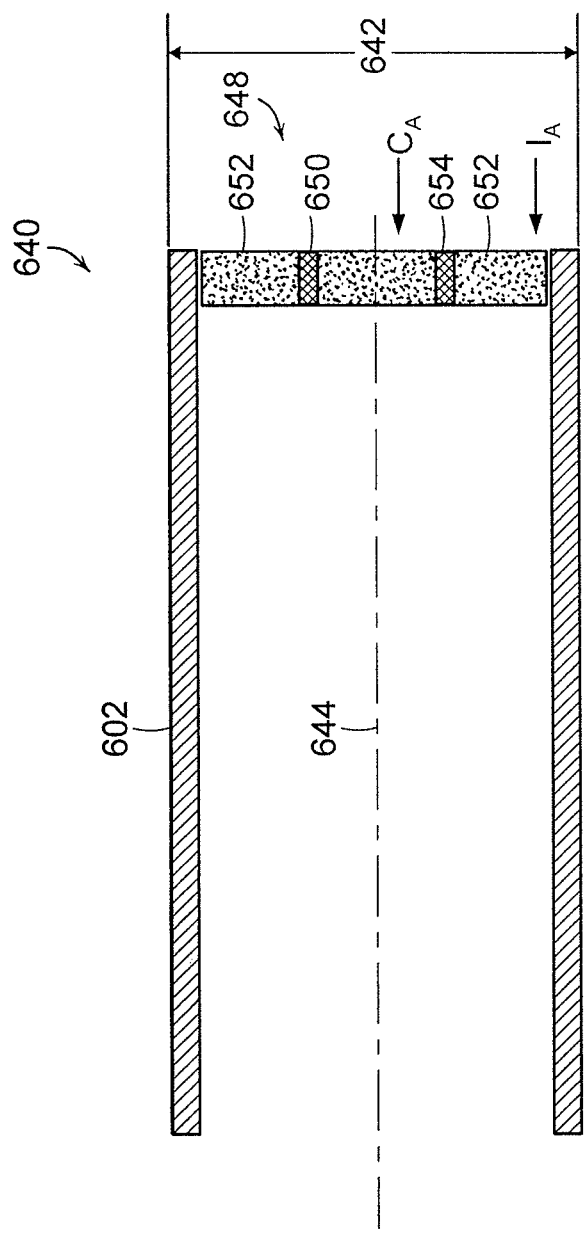

The distal end 640 of tube 602 of the sheath 600 is shown in the embodiment of FIG. 24F. The outer diameter 642 is 3 mm or less with a preferred embodiment of 2 mm or less. Particular examples of the sheath have outer diameters of 1.7 mm and 1.2 mm. Smaller diameters are important for minimizing discomfort to the patient in many applications. The distal end 640 is sealed with window assembly 648. The window assembly 648 can include a light collection window 650 with a light collection area $C_A$ and an illumination window 652 with an illumination area $I_A$ that extends circumferentially around window 650. An opaque adhesive layer or tube element 654 that is held in place with an adhesive forms a light barrier between the outer window 652 and central window 650. The window 650 is aligned along the optical axis 644 of the disposable sheath 600.

In another preferred embodiment, the window assembly 648 can be replaced by a prism assembly to provide angled viewing. Alternatively, a prism assembly can be mounted on the distal end of assembly 620 that is enclosed by a disposable sheath with a window assembly that is shaped to conform to the prism assembly to provide for angled viewing. The prism assembly can be attached to the distal end by an adhesive or a snap connector, for example.

The ratio of the light illumination area $I_A$ to the light collection area $C_A$ is an important metric in small diameter endoscopes as it represents the light distribution required to provide the needed image quality for a given application. A ratio in the range of 0.5 to 2.5 is preferred, particularly for arthroscopic applications where it is desirable to have a field of view in a range of 60 degrees to 75 degrees and a depth of field in a range of 1.5 mm to 50 mm, depending on the application. For arthroscopic applications, such as the knee, shoulder or hip, the far field of 25-50 mm is important so that the system is tuned to have a depth of field of 3 mm-50 mm. For smaller joints, such as the wrist or foot, a near field is preferred with a range of 1.5-25 mm. The aperture stop 676 can be adjusted to improve imaging for the desired depth of field. This provides a large image and field of view by reducing the volume occupied by the illumination fiber.

Figure 24H:
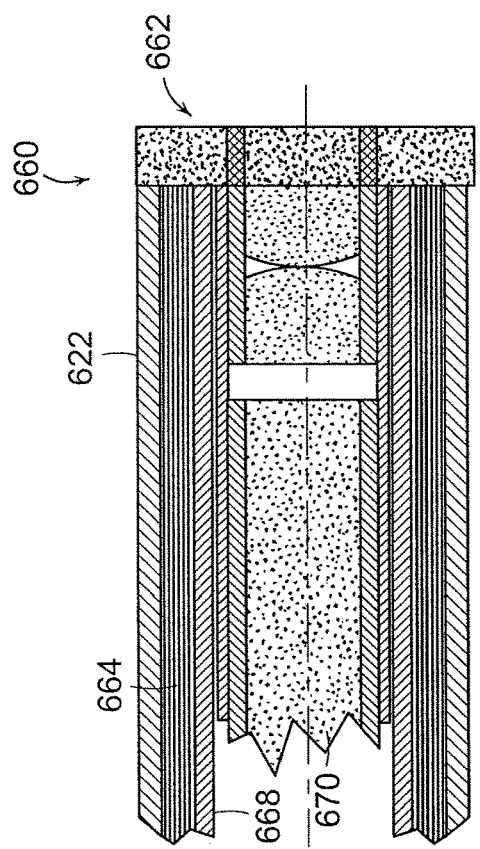
Figure 24G:
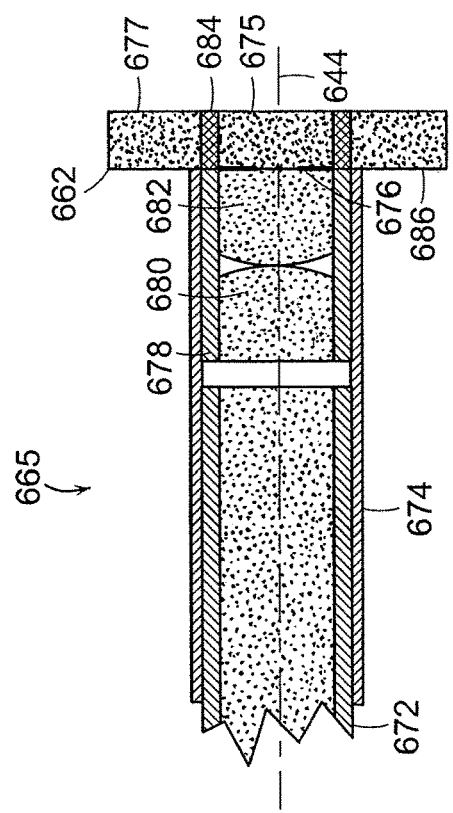

The distal end 660 of the tube 622 for the imaging and illumination assembly 620 is shown in FIGS. 24G-24H. The tube 622 has a second window assembly 662 that seals the distal end. As seen in FIG. 24G, the second window assembly 662 includes an inner window 675, an adhesive layer or tube 684 that provides an opaque light barrier between the inner window 675 and outer window 677. The proximal surface of window 675 can have an aperture stop 676 in the form of a thin film. The lens elements 680, 682 are fixed within tube 678 with an adhesive. The lens and window assembly 662 is mounted to the imaging fibers 670 within tube 672 with coupling tube 674. The assembly of FIG. 24G then slides into the inner tube 668 that holds the illumination fibers 664 along with tube 622. An adhesive layer on surface 686 can be used to secure the window assembly 662 to the distal surface of fibers 664.

Figure 24I:
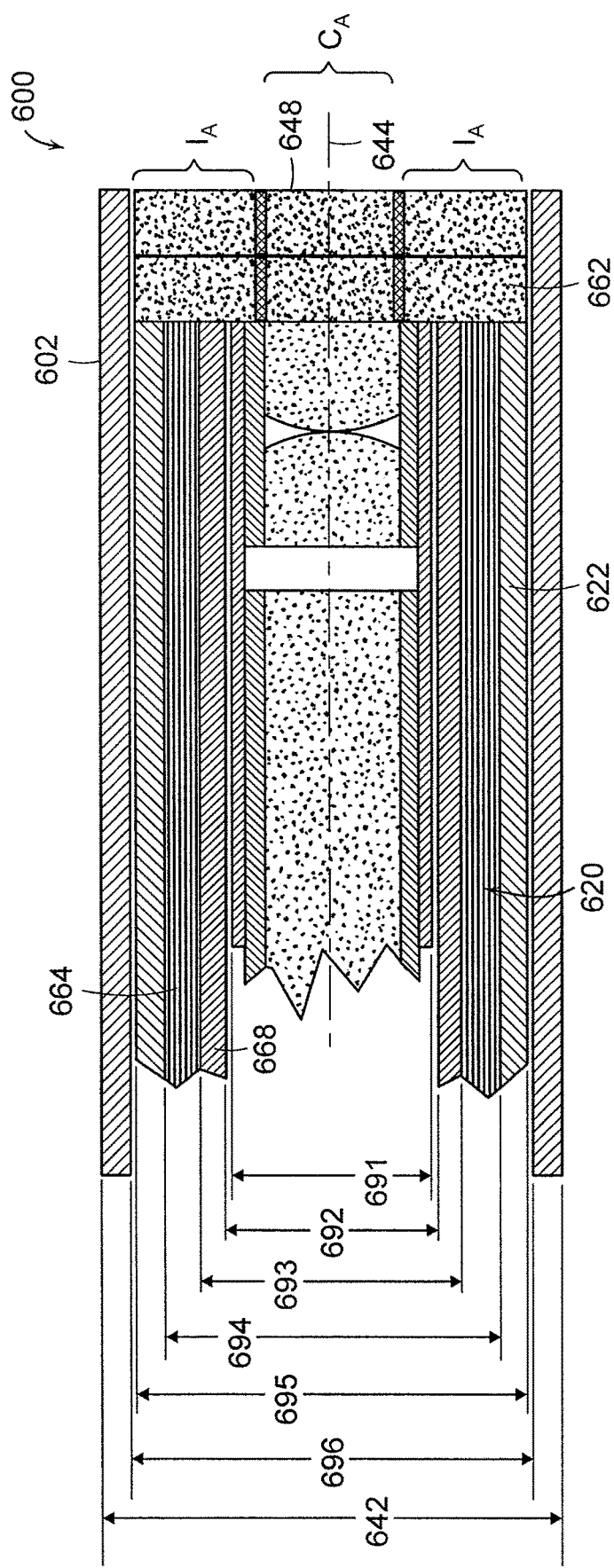

Shown in FIG. 24I is cross sectional view of the distal end of the imaging assembly 620 upon insertion into the sheath 600. The window assembly 648 is aligned with the second window assembly 662 along axis 644. The outer tube 602 has an outer diameter 642 of 3 mm or less, and preferably 2 mm or less. The inner diameter 696 of tube 602 is just large enough to accommodate the outer diameter 695 of tube 622 as it slides into place such that the distal surface of second window assembly 662 butts against the proximal surface of window assembly 648. Thus, light from the illumination fibers 664 is directed through window elements 677 and 652 and light reflected off the tissue structure to be imaged and collected through window elements 650 and 675. The illumination fibers 664 are situated between the inner diameter 694 of tube 622 and the outer diameter 693 of tube 668. The inner diameter 692 of tube 668 is just larger than the outer diameter 691 of tube 674 so that it will slide into place during manufacture as described above. A preferred embodiment has a tube 602 outer diameter 642 of 1.67 mm, tube 602 inner diameter 696 of 1.47 mm, illumination outer tube 622 diameter 695 of 1.42 mm, the tube 622 having an inner diameter 694 of 1.22 mm, an illumination inner tube 668 with outer diameter 693 of 1.07 mm and an inner diameter 692 of 0.91 mm, and finally the outer diameter 691 of tube 674 is 0.89 mm. The central window 650 has a diameter of 0.6 mm in this particular embodiment. The illumination area $I_A$ for this embodiment is about 1.09 mm² and the collection window has an area $C_A$ of about 0.442 mm², thus providing a ratio of about 2.47.

In another embodiment, during manufacture of the illumination component including outer tube 622, inner tube 668 and fibers 664, it can be advantageous to use a Teflon tube for inner tube 668 such that after the distal ends of the fibers are bound together with the adhesive, the inner Teflon tube can removed, thus creating a larger diameter cavity in which the imaging channel can be inserted. The diameter of the central window is consequently larger and the inner diameter of the illumination window is also larger, thereby reducing the illumination area. In this embodiment the ratio of the illumination area to collection area is about 1.6.

Figure 25:
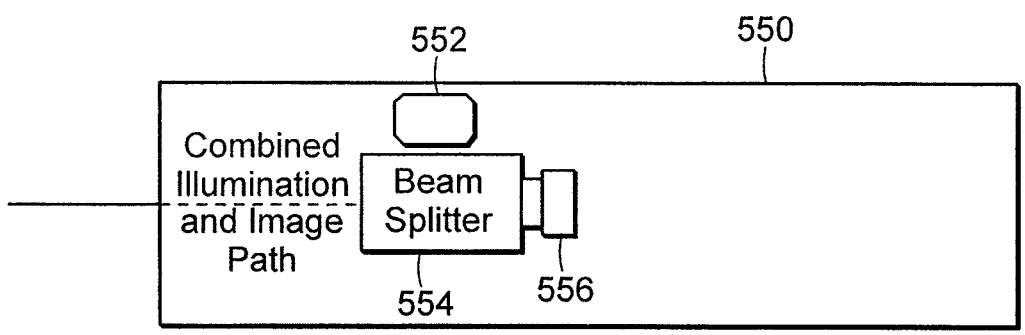
FIG. 25 is a schematic view of another preferred embodiment of an endoscopic device.

FIG. 25 illustrates an embodiment in which a beam splitter 554 in the handle 550 optically couples both the light source 552 and the imaging device 556 to a single fiber bundle. This provides for illumination and light collection through a single light channel. The light source can be LED source and/or a laser as described previously herein.

Shown in FIGS. 26 and 27 are side and end cross sectional views of a fiber optic illumination cannula 800 suitable for use in a preferred embodiment of the invention. The cannula assembly 800 includes a cannula housing 802 that is rigidly attached to a fluid connector 812 having a fluid channel 816 for introducing fluids into the cannula housing 802 which can then be delivered through channel 826 of distal probe 820 into a patient. A trocar 804 has a distal end 805 that extends distally from the end of probe 820 with a sharp point to aid in penetration of the probe into tissue of the patient. The trocar 804 can have a flange 814 that seals against the wall of the inner channel 815 such that fluid injected through channel 816 and directed through channel 826 around the trocar probe 811.

The illumination fibers 808 can be connected to a light source 806 via cable 810. As seen in FIG. 27, the distal ends of fibers 808 form an illumination surface at the distal end of the probe 820 between outer tube 822 and inner tube 824. The distal faces of the fibers can be cut at an angle to provide improved ease of insertion and which directs the light toward the central axis 828. After insertion of the cannula/trocar assembly into the patient and removal of the trocar, the imaging unit with a disposable tubular sheath with a window at the distal end can be inserted through channel 826 as generally described herein. The sheath or imaging assembly can also be fitted with a prism to provide angled viewing as described herein.

Alternatively, as in previous embodiments, the light source can be positioned within the handle and coupled directly into the illumination fibers. However, the illumination fibers will have an optical coupler at the proximal end that receives light through a sealing window in the hub of the disposable sheath from the light source in the handle. This is necessary to maintain a sterile environment of the imaging unit. The sterile barrier in this embodiment can be attached to the disposable sheath adjacent the hub with the proximal connector to the imaging unit.

Many changes in the details, materials and arrangements of parts, herein described and illustrated, can be made by those skilled in the art in light of teachings contained hereinabove. Accordingly, it will be understood that the following claims are not to be limited to the embodiments disclosed herein and can include practices other than those specifically described, and are to be interpreted as broadly as allowed under the law.

What is claimed:

1. An endoscope for imaging a joint region within a mammalian body comprising:
   an endoscope handle having a control panel to electrically actuate an imaging procedure, the endoscope handle including a light emitting diode (LED) emitter and an imaging sensor chip having an image processor, an image sensor, a clock, and a controller;
   an endoscope tube attached to the endoscope handle, the endoscope tube having an outer diameter of less than 3 mm and an annular array of illumination optical fibers within the endoscope tube, the optical fibers arranged in the annular array that surrounds an imaging channel within the endoscope tube, the illumination optical fibers being concentric about the imaging channel, a distal end of the illumination optical fibers being positioned to define a concentric illumination area;
   a light transmitting element sealed at a distal end of the endoscope tube to enclose the imaging channel, the light transmitting element defining a light collection area such that a ratio of the concentric illumination area to the light collection area is in a range of 0.5 to 2.0; and
   an optical coupler at a proximal end of the endoscope tube, the optical coupler adapted to couple the proximal end of the illumination optical fibers to the light emitting diode (LED) emitter within the endoscope handle, the optical coupler connected to the proximal end of the illumination optical fibers, the optical coupler comprising an illumination fiber bundle such that the annular array of illumination optical fibers extend to the illumination fiber bundle such that the LED emitter is aligned with the optical coupler.

2. The endoscope of claim 1 wherein the endoscope tube is configured to slide within a cannula and further comprising a cannula connector.

3. The endoscope of claim 1 wherein the outer diameter of the endoscope tube is less than 2 mm and the endoscope further comprises a plurality of imaging optical fibers coupled to the imaging sensor chip that includes a two dimensional array of pixel elements, the controller that operates in response to the control panel, and a memory for storing image data.

4. The endoscope of claim 3 wherein the endoscope tube further comprises an inner tube that has a diameter in a range of 0.6 to 1.8 mm and the array of illumination optical fibers comprises between 500 and 2000 optical fibers.

5. The endoscope of claim 1 wherein the light transmitting element comprises a window attached to an inner tube of the endo scope tube.

6. The endoscope of claim 1 further comprising a sterile barrier attached to a sheath housing element at a proximal end of the endoscope tube.

7. The endoscope of claim 1 wherein the endoscope tube comprises a tube having a cylindrical cavity containing a plurality of imaging fibers and has a length between 5 cm and 10 cm.

8. The endoscope of claim 1 wherein the array of illumination optical fibers comprises a plurality of concentric rows that are positioned within an outer tube and an inner tube.

9. The endoscope of claim 8 wherein the illumination optical fibers have a packing factor of at least 90% and are attached with an adhesive at a distal end and have a polished distal surface.

10. The endoscope of claim 1 wherein the endoscope tube is between 50 mm and 2500 mm in length.

11. The endoscope of claim 1 further comprising a fluid delivery channel for delivering medication or imaging dye to a region of interest in a body lumen or cavity.

12. The endoscope of claim 1 further comprising a first fluid seal, an o-ring groove and a second fluid seal on the optical coupler.

13. The endoscope of claim 1, wherein the light transmitting element is configured to provide angled viewing relative to a longitudinal axis of the endoscope tube.

14. The endoscope of claim 13, wherein the light transmitting element includes an angled viewing element attached to the endoscope tube for angled viewing relative to a longitudinal axis of the endoscope tube.

15. The endoscope of claim 14, wherein the angled viewing element is at least one of a lens, mirror or prism.

16. The endoscope of claim 14, wherein the angled viewing element is configured for removable association with the endoscope handle.

17. The endoscope of claim 16, wherein the angled viewing element is secured relative to the endoscope tube with an adhesive.

18. The endoscope of claim 13, wherein the light transmitting element is configured to provide for angled viewing at a predetermined angle relative to the longitudinal axis of the endoscope tube.

19. The endoscope of claim 18, wherein the angled viewing is in a range of 1-10 degrees relative to the longitudinal axis of the endoscope tube.

20. The endoscope of claim 13, wherein the light transmitting element comprises a prism having a face angled at from 10-30 degrees.

21. The endoscope of claim 13, wherein the light transmitting element is shaped to conform with an angled viewing element on a proximal end of the endoscope tube.

22. The endoscope of claim 13, wherein the illumination optical fibers are configured to provide for angled illumination relative to a longitudinal axis of the endoscope tube.

23. The endoscope of claim 22, wherein the light transmitting element is configured to provide for angled viewing at a predetermined angle relative to the longitudinal axis of the endoscope tube.

24. The endoscope of claim 23, wherein the angled viewing is in a range of 1-10 degrees relative to the longitudinal axis of the endoscope tube.

25. The endoscope of claim 22, wherein the distal ends of the illumination optical fibers are angled to provide the angled illumination relative to the longitudinal axis.

26. The endoscope of claim 1, wherein the illumination optical fibers comprise plastic fibers.

27. The endoscope of claim 1, further comprising a cannula assembly extending around the illumination optical fibers.

28. The endoscope of claim 1, wherein the illumination optical fibers have a diameter in a range of 30 microns to 50 microns.

29. An endoscope for imaging a joint region within a mammalian body comprising:
    an endoscope handle having a control panel to electrically actuate an imaging operation, the endoscope handle further including a light emitting diode (LED) emitter and an imaging sensor chip including an image processor, an image sensor, a clock, and a controller;
    an endoscope tube having an outer diameter of less than 2 mm and an annular array of illumination optical fibers within the endoscope tube, the illumination optical fibers arranged in a plurality of rows in the annular array that surrounds an imaging channel within an outer tube of the endoscope tube, the illumination optical fibers being concentric around an inner tube and having a packing factor between the inner tube and outer tube of at least 80%, a distal end of the illumination optical fibers being secured between the inner tube and the outer tube to define a concentric illumination area at a distal end of the endoscope tube;
    an optically transparent element sealed at a distal end of the outer tube to enclose the endoscope tube, the optically transparent element defining a light collection area such that a ratio of the concentric illumination area to the light collection area is in a range of 0.5 to 2.0;
    a cannula in which the endoscope tube slides; and
    an optical coupler at a proximal end of the endoscope tube, the optical coupler adapted to couple a proximal end of the illumination optical fibers to the light emitting diode (LED) emitter with an optical fiber bundle.

30. The endoscope of claim 29 wherein a connector assembly connects the endo scope tube to the endo scope handle and further comprising a cannula connector.

31. The endoscope of claim 29 wherein the inner tube surrounds the imaging channel having a plurality of imaging optical fibers that are optically coupled to the imaging sensor chip with a lens, the imaging sensor chip further comprising a single chip having the controller, a memory and a two dimensional array of pixel elements.

32. The endoscope of claim 31 wherein the inner tube has a diameter in a range of 0.6 to 1.8 mm and the array of illumination optical fibers comprises between 500 and 2000 optical fibers.

33. The endoscope of claim 29 wherein the optically transparent element comprises a window attached to the inner tube.

34. The endoscope of claim 29 further comprising a sterile barrier attached to a sheath housing element at a proximal end of the endoscope tube.

35. The endoscope of claim 29 wherein the illumination optical fibers have a packing factor of at least 90% and are attached with an adhesive at the distal end and have a polished distal surface.

36. The endoscope of claim 29 wherein the endoscope tube comprises a sheath that is between 50 mm and 2500 mm in length.

37. The endoscope of claim 29 wherein the cannula includes a fluid delivery channel for delivering medication or imaging dye to a region of interest in a body lumen or cavity.

38. An endoscope for imaging a region within a mammalian body comprising:
    an endoscope handle having a control panel to electrically actuate an imaging operation, the endoscope handle further including light emitting diode (LED) emitter and an imaging sensor chip that includes an image processor, an image sensor, a clock, a controller and a memory;
    an endoscope tube having an outer diameter of less than 3 mm and an annular array of illumination optical fibers within the endoscope tube, the illumination optical fibers arranged in the annular array that surround an imaging channel within the endoscope tube the illumination optical fibers being concentric about an inner tube such that the illumination optical fibers have a packing factor between the inner tube and an outer tube of at least 80%, the illumination optical fibers having distal ends secured to define a concentric illumination area;
    a light transmitting element sealed at a distal end of the endoscope tube to enclose the imaging channel, the light transmitting element having a light collection area such that a ratio of the concentric illumination area to the light collection area is in a range of 0.5 to 2.0;
    a cannula wherein the endoscope tube slides within the cannula;
    wherein the endoscope includes a fluid port such that a fluid can be inserted into the mammalian body; and
    an optical coupler at a proximal end of the endoscope tube, the optical coupler adapted to couple the proximal end of the endoscope tube to the light emitting diode (LED) emitter within the handle, the optical coupler connected to a proximal end of the illumination optical fibers that receives light from the LED emitter, the optical coupler connecting an illumination fiber bundle such that the annular array of illumination optical fibers extend to the illumination fiber bundle.

* * * * *